(12) United States Patent
Mayer et al.

(10) Patent No.: US 10,670,578 B2
(45) Date of Patent: *Jun. 2, 2020

(54) CONTROLLING TRANSLOCATION THROUGH NANOPORES WITH FLUID WALLS

(71) Applicant: THE REGENTS OF THE UNIVERSITY OF MICHIGAN, Ann Arbor, MI (US)

(72) Inventors: Michael Mayer, Ann Arbor, MI (US); Erik Yusko, Ann Arbor, MI (US); Jerry Yang, La Jolla, CA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/377,970

(22) Filed: Apr. 8, 2019

(65) Prior Publication Data

US 2019/0234930 A1 Aug. 1, 2019

Related U.S. Application Data

(63) Continuation of application No. 15/157,591, filed on May 18, 2016, now Pat. No. 10,254,271, which is a
(Continued)

(51) Int. Cl.
*G01N 33/487* (2006.01)
*G01N 27/26* (2006.01)
(Continued)

(52) U.S. Cl.
CPC ........ *G01N 33/48721* (2013.01); *B82Y 30/00* (2013.01); *C12Q 1/6869* (2013.01); *G01N 15/1209* (2013.01); *G01N 2015/0038* (2013.01)

(58) Field of Classification Search
CPC ........ G01N 27/3278; G01N 33/48721; G01N 15/1209; G01N 2015/0038; C12Q 2565/631; C12Q 1/6869; B82Y 30/00
See application file for complete search history.

(56) References Cited

U.S. PATENT DOCUMENTS

2,656,508 A 10/1953 Coulter
7,521,225 B2 4/2009 Smirnov
(Continued)

FOREIGN PATENT DOCUMENTS

WO WO-2006137891 A2 12/2006
WO WO-2007127327 A2 11/2007
(Continued)

OTHER PUBLICATIONS

Wang et al., Anal. Chem, 2011, 83, 1746-1752 (Year: 2011).*
(Continued)

*Primary Examiner* — Gurpreet Kaur
(74) *Attorney, Agent, or Firm* — Harness, Dickey & Pierce, P.L.C.

(57) ABSTRACT

Improved resolution and detection of nanoparticles are achieved when a nanopore connecting liquid compartments in a device running on the Coulter principle is provided with fluid coatings such as lipid walls. Fluid lipid walls are made of a lipid bilayer, and preferably include lipid anchored mobile ligands as part of the lipid bilayer. By varying the nature and concentration of the mobile ligand in the lipid bilayer, multifunctional coatings of lipids are provided.

20 Claims, 38 Drawing Sheets

Related U.S. Application Data continuation of application No. 13/400,472, filed on Feb. 20, 2012, now Pat. No. 9,347,929.

(60) Provisional application No. 61/448,093, filed on Mar. 1, 2011.

(51) Int. Cl.
    *B82Y 30/00*     (2011.01)
    *C12Q 1/68*     (2018.01)
    *C12Q 1/6869*     (2018.01)
    *G01N 15/12*     (2006.01)
    *G01N 15/00*     (2006.01)

(56) References Cited

U.S. PATENT DOCUMENTS

| | | | |
|---|---|---|---|
| 7,777,505 | B2 | 8/2010 | White et al. |
| 9,347,929 | B2 * | 5/2016 | Mayer .............. G01N 33/48721 |
| 9,557,292 | B2 | 1/2017 | Mayer et al. |
| 10,254,271 | B2 * | 4/2019 | Mayer .............. G01N 33/48721 |
| 10,317,361 | B2 | 6/2019 | Mayer et al. |
| 2006/0183112 | A1 | 8/2006 | Min et al. |
| 2007/0298511 | A1 | 12/2007 | Kang et al. |
| 2008/0254995 | A1 * | 10/2008 | Kim ....................... B82Y 30/00 |
| | | | 506/4 |
| 2008/0286750 | A1 | 11/2008 | Xu et al. |
| 2009/0184047 | A1 | 7/2009 | Thayumanavan et al. |
| 2010/0148126 | A1 * | 6/2010 | Guan .................. C07D 233/06 |
| | | | 252/500 |
| 2011/0159601 | A1 | 6/2011 | Golovchenko et al. |
| 2011/0177498 | A1 | 7/2011 | Clarke et al. |
| 2011/0250705 | A1 | 10/2011 | Polonsky et al. |
| 2012/0133354 | A1 | 5/2012 | Canas et al. |

FOREIGN PATENT DOCUMENTS

| | | |
|---|---|---|
| WO | WO-2008102120 A1 | 8/2008 |
| WO | WO-2008102121 A1 | 8/2008 |
| WO | WO-2009020682 A2 | 2/2009 |
| WO | WO-2009077734 A2 | 6/2009 |
| WO | WO-2010004265 A1 | 1/2010 |
| WO | WO-2010004273 A1 | 1/2010 |
| WO | WO-2010086602 A1 | 8/2010 |
| WO | WO-2010086603 A1 | 8/2010 |
| WO | WO-2010086622 A1 | 8/2010 |
| WO | WO-2010122293 A1 | 10/2010 |
| WO | WO-2014074922 A1 | 5/2014 |

OTHER PUBLICATIONS

Ali et al., "Biosensing and Supramolecular Bioconjugation in Single Conical Polymer Nanochannels. Facile Incorporation of Biorecognition Elements into Nanoconfined Geometries." Journal of the American Chemical Society, vol. 130, No. 48, pp. 16351-16357 (2008).
Axelrod et al., "Mobility measurement by analysis of fluorescence photobleaching recovery kinetics." Biophysical Journal, vol. 16, No. 9, pp. 1055-1069 (1976).
Bayley et al., "Stochastic sensors inspired by biology." Nature, vol. 413, pp. 226-230 (2001).
Benner et al., "Sequence-specific detection of individual DNA polymerase complexes in real time using a nanopore." Nature Nanotechnology, vol. 2, No. 11, pp. 718-724 (2007).
Branton et al., "The potential and challenges of nanopore sequencing." Nature Biotechnology, vol. 26, No. 10, pp. 1146-1153 (2008).
Clarke et al., "Continuous base identification for single-molecule nanopore DNA sequencing." Nature Nanotechnology, vol. 4, pp. 265-270 (2009).
Cremer et al., "Formation and Spreading of Lipid Bilayers on Planar Glass Supports." The Journal of Physical Chemistry B, vol. 103, No. 13, pp. 2554-2559 (1999).
DeBlois et al., "Counting and Sizing of Submicron Particles by the Resistive Pulse Technique." The Review of Scientific Instruments, vol. 41, No. 7, pp. 909-915 (1970).
Dekker, "Solid-state nanopores." Nature Nanotechnology, vol. 2, pp. 209-215 (2007).
Erickson, "Size and Shape of Protein Molecules at the Nanometer Level Determined by Sedimentation, Gel Filtration, and Electron Microscopy." Biological Procedures Online, vol. 11, No. 1, pp. 32-51 (2009).
Fologea et al., "Electrical characterization of protein molecules by a solid-state nanopore." Applied Physics Letters, vol. 91, No. 5, pp. 053901-1-053901-3 (2007).
Gennis, "Biomembranes: Molecular Structure and Function." Springer, New York, pp. 60-65 (1989).
Golibersuch, "Observation of Aspherical Particle Rotation in Poiseuille Flow via the Resistance Pulse Technique: I. Application to Human Erythrocytes." Biophysical Journal, vol. 13, No. 3, pp. 265-280 (1973).
Griffiths, "The realm of the nanopore: Interest in nanoscale research has skyrocketed, and the humble pore has become a king." Analytical Chemistry, vol. 80, No. 1, pp. 23-27 (2008).
Grover et al., "Electrical Sizing of Particles in Suspensions: I. Theory." Biophysical Journal, vol. 9, No. 11, pp. 1398-1414 (1969).
Grover et al., "Electrical Sizing of Particles in Suspensions: II. Experiments with Rigid Spheres." Biophysical Journal, vol. 9, No. 11, pp. 1415-1425 (1969).
Guo et al., "Charge substitution shows that repulsive electrostatic interactions impede the oligomerization of Alzheimer amyloid peptides." FEBS Letters, vol. 579, No. 17, pp. 3574-3578 (2005).
Hall et al., "Electrophoretic Force on a Protein-Coated DNA Molecule in a Solid-State Nanopore." Nano Letters, vol. 9, No. 12, pp. 4441-4445 (2009).
Han et al., "Label-Free Detection of Single Protein Molecules and Protein-Protein Interactions Using Synthetic Nanopores." Analytical Chemistry, vol. 80, No. 12, pp. 4651-4658 (2008).
Han et al., "Sensing protein molecules using nanofabricated pores." Applied Physics Letters, vol. 88, pp. 093901-1-093901-3 (2006).
Hansen et al., "Development of an automation technique for the establishment of functional lipid bilayer arrays." Journal of Micromechanics and Microengineering, vol. 19, No. 2, pp. 025014-1-025014-11 (2009).
Hernández-Ainsa et al., "Lipid-coated nanocapillaries for DNA sensing." Analyst, vol. 138, pp. 104-106 (2013).
Hille, "Ionic Channels in Excitable Membranes." Biophysical Journal, vol. 22, No. 2, pp. 283-294 (1978).
Howorka et al., "Nanopore analytics: sensing of single molecules." Chemical Society Reviews, vol. 38, No. 8, pp. 2360-2384 (2009).
Hurley, "Sizing Particles with a Coulter Counter." Biophysical Journal, vol. 10, No. 1, pp. 74-79 (1970).
Ito et al., "Simultaneous Determination of the Size and Surface Charge of Individual Nanoparticles Using a Carbon Nanotube-Based Coulter Counter." Analytical Chemistry, vol. 75, No. 10, pp. 2399-2406 (2003).
Jachimska et al., "Characterization of Globular Protein Solutions by Dynamic Light Scattering, Electrophoretic Mobility, and Viscosity Measurements." Langmuir, vol. 24, No. 13, pp. 6866-6872 (2008).
Jan et al., "Preparation and characterization of toxic Aβ aggregates for structural and functional studies in Alzheimer's disease research." Nature Protocols, vol. 5, No. 6, pp. 1186-1209 (2010).
Janssen et al., "Electromagnetic Torque Tweezers: A Versatile Approach for Measurement of Single-Molecule Twist and Torque." Nano Letters, vol. 12, No. 7, pp. 3634-3639 (2012).
Kasianowicz et al., "Characterization of individual polynucleotide molecules using a membrane channel." Proceedings of the National Academy of Sciences, vol. 93, No. 24, pp. 13770-13773 (1996).
Kellermayer et al., "Stepwise dynamics of epitaxially growing single amyloid fibrils." Proceedings of the National Academy of Sciences, vol. 105, No. 1, pp. 141-144 (2008).
Li et al., "Ion-beam sculpting at nanometre length scales." Nature, vol. 412, pp. 166-169 (2001).
Li et al., "The distribution of DNA translocation times in solid-state nanopores." Journal of Physics: Condensed Matter, vol. 22, No. 45, pp. 454129-1-454129-8 (2010).

(56) References Cited

OTHER PUBLICATIONS

Macrae et al., "A Semi-Synthetic Ion Channel Platform for Detection of Phosphatase and Protease Activity." ACS Nano, vol. 3, No. 11, pp. 3567-3580 (2009).
Majd et al., "Gramicidin Pores Report the Activity of Membrane-Active Enzymes." Journal of the American Chemical Society, vol. 131, No. 44, pp. 16119-16126 (2009).
Martin et al., "Learning Nature's Way: Biosensing with Synthetic Nanopores." Science, vol. 317, No. 5836, pp. 331-332 (2007).
Mathé et al., "Orientation discrimination of single-stranded DNA inside the α-hemolysin membrane channel." Proceedings of the National Academy of Sciences, vol. 102, No. 35, pp. 12377-12382 (2005).
Movileanu et al., "Detecting protein analytes that modulate transmembrane movement of a polymer chain within a single protein pore." Nature Biotechnology, vol. 18, No. 10, pp. 1091-1095 (2000).
Movileanu, "Interrogating single proteins through nanopores: challenges and opportunities." Trends in Biotechnology, vol. 27, No. 6, pp. 333-341 (2009).
Nilsson et al., "Localized functionalization of single nanopores." Advanced Materials, vol. 18, No. 4, pp. 427-431 (2006).
Oukhaled et al., "Unfolding of Proteins and Long Transient Conformations Detected by Single Nanopore Recording." Physical Review Letters, vol. 98, No. 15, pp. 158101-1-158101-4 (2007).
Pandey et al., "Proteomics to study genes and genomes." Nature, vol. 405, No. 6788, pp. 837-846 (2000).
Pedone et al., "Data Analysis of Translocation Events in Nanopore Experiments." Analytical Chemistry, vol. 81, No. 23, pp. 9689-9694 (2009).
Prangkio, "Investigation of Cytotoxicity and Ion Flux Induced by Various Aggregation States of Amyloid-Beta Peptides." Ph.D. Dissertation, The University of Michigan (2011).
Qin et al., "Effects of particle's off-axis position, shape, orientation and entry position on resistance changes of micro Coulter counting devices." Measurement Science and Technology, vol. 22, No. 4, pp. 045804-1-045804-10 (2011).
Raillon et al., "Nanopore Detection of Single Molecule RNAP-DNA Transcription Complex." Nano Letters, vol. 12, No. 3, pp. 1157-1164 (2012).
Reimhult et al., "Intact Vesicle Adsorption and Supported Biomembrane Formation from Vesicles in Solution: Influence of Surface Chemistry, Vesicle Size, Temperature, and Osmotic Pressure." Langmuir, vol. 19, No. 5, pp. 1681-1691 (2003).
Robertson et al., "Single-molecule mass spectrometry in solution using a solitary nanopore." Proceedings of the National Academy of Sciences, vol. 104, No. 20, pp. 8207-8211 (2007).
Rosenstein et al., "Integrated nanopore sensing platform with submicrosecond temporal resolution." Nature Methods, vol. 9, No. 5, pp. 487-492 (2012).
Rotem et al., "Protein Detection by Nanopores Equipped with Aptamers." Journal of the American Chemical Society, vol. 134, No. 5, pp. 2781-2787 (2012).
Sackmann, "Supported Membranes: Scientific and Practical Applications." Science, vol. 271, No. 5245, pp. 43-48 (1996).
Schar et al., "Sulfates of ethoxylated tridecyl alcohol in dishwashing formulations." Journal of the American Oil Chemists' Society, vol. 37, No. 9, pp. 427-430 (1960).
Sexton et al., "An Adsorption-Based Model for Pulse Duration in Resistive-Pulse Protein Sensing." Journal of the American Chemical Society, vol. 132, No. 19, pp. 6755-6763 (2010).
Sexton et al., "Resistive-Pulse Studies of Proteins and Protein/Antibody Complexes Using a Conical Nanotube Sensor." Journal of the American Chemical Society, vol. 129, No. 43, pp. 13144-13152 (2007).
Skinner et al., "Distinguishing Single- and Double-Stranded Nucleic Acid Molecules Using Solid-State Nanopores." Nano Letters, vol. 9, No. 8, pp. 2953-2960 (2009).
Solomentsev et al., "Electrophoretic transport of spheroidal colloids in nonhomogeneous electric fields." Industrial & Engineering Chemistry Research, vol. 34, No. 10, pp. 3231-3238 (1995).
Soni et al., "Detection of Nucleosomal Substructures using Solid-State Nanopores." Nano Letters, vol. 12, No. 6, pp. 3180-3186 (2012).
Starr et al., "Formation and Characterization of Planar Phospholipid Bilayers Supported on $TiO_2$ and $SrTiO_3$ Single Crystals." Langmuir, vol. 16, No. 26, pp. 10301-10308 (2000).
Studer, "Investigations on planar lipid bilayers in nano-pores to study the function of membrane proteins." Doctoral Thesis No. 18473, Eth Zurich (2009).
Talaga et al., "Single-Molecule Protein Unfolding in Solid State Nanopores." Journal of the American Chemical Society, vol. 131, No. 26, pp. 9287-9297 (2009).
Timbs et al., "Slow rotational mobilities of antibodies and lipids associated with substrate-supported phospholipid monolayers as measured by polarized fluorescence photobleaching recovery." Biophysical Journal, vol. 58, No. 2, pp. 413-428 (1990).
Uram et al., "Label-Free Affinity Assays by Rapid Detection of Immune Complexes in Submicrometer Pores." Angewandte Chemie International Edition, vol. 45, No. 14, pp. 2281-2285 (2006).
Uram et al., "Noise and Bandwidth of Current Recordings from Submicrometer Pores and Nanopores." ACS Nano, vol. 2, No. 5, pp. 857-872 (2008).
Uram et al., "Submicrometer Pore-Based Characterization and Quantification of Antibody-Virus Interactions." Small, vol. 2, No. 8-9, pp. 967-972 (2006).
Venkatesan et al., "Lipid bilayer coated $Al_2O_3$ nanopore sensors: towards a hybrid biological solid-state nanopore." Biomedical Microdevices, vol. 13, No. 4, pp. 671-682 (2011).
Wei et al., "Stochastic sensing of proteins with receptor-modified solid-state nanopores." Nature Nanotechnology, vol. 7, No. 4, pp. 257-263 (2012).
Woodside et al., "Direct Measurement of the Full, Sequence-Dependent Folding Landscape of a Nucleic Acid." Science, vol. 314, No. 5801, pp. 1001-1004 (2006).
Yusko et al., "Controlling protein translocation through nanopores with bio-inspired fluid walls." Nature Nanotechnology, vol. 6, No. 4, pp. 253-260 (2011).
Yusko et al., "Lipid Bilayers in Nanopores to Vary their Diameter, Characterize Amyloid-β Aggregates and Monitor the Activity of Membrane-Active Enzymes." Biophysical Journal, vol. 98, No. 2, p. 598a (2010).
Yusko et al., "Nanopore Recordings to Quantify Activity-Related Properties of Proteins." Nanopores: Sensing and Fundamental Biological Interactions, Springer Science + Business Media, Llc, pp. 203-225 (2011).
Yusko et al., "Single-Particle Characterization of Aβ Oligomers in Solution." ACS Nano, vol. 6, No. 7, pp. 5909-5919 (2012).
Zhao et al., "Real-Time Monitoring of Peptide Cleavage Using a Nanopore Probe." Journal of the American Chemical Society, vol. 131, No. 18, pp. 6324-6325 (2009).

* cited by examiner

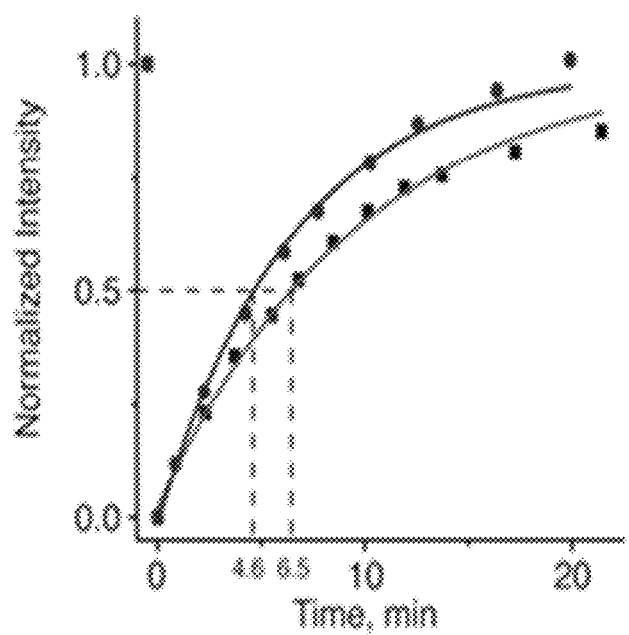
FIG. 17B
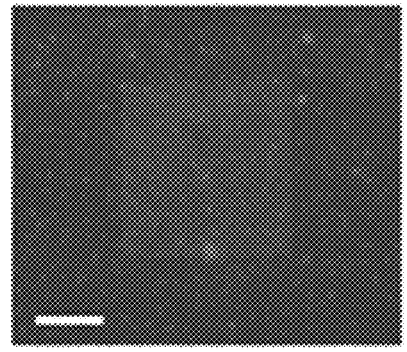
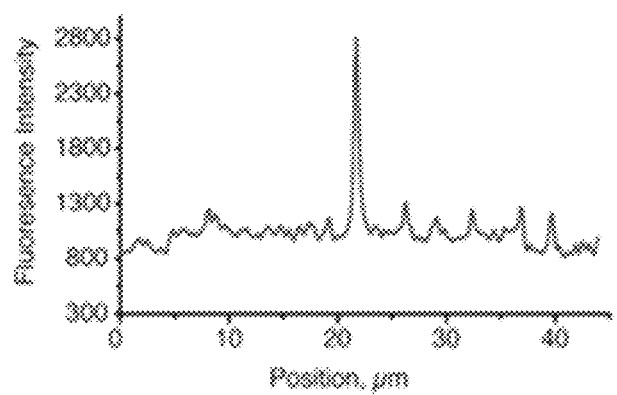
FIG. 18A

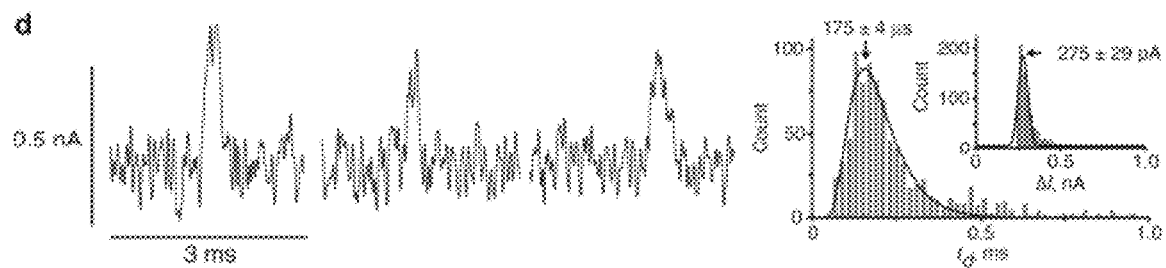
FIG. 24D
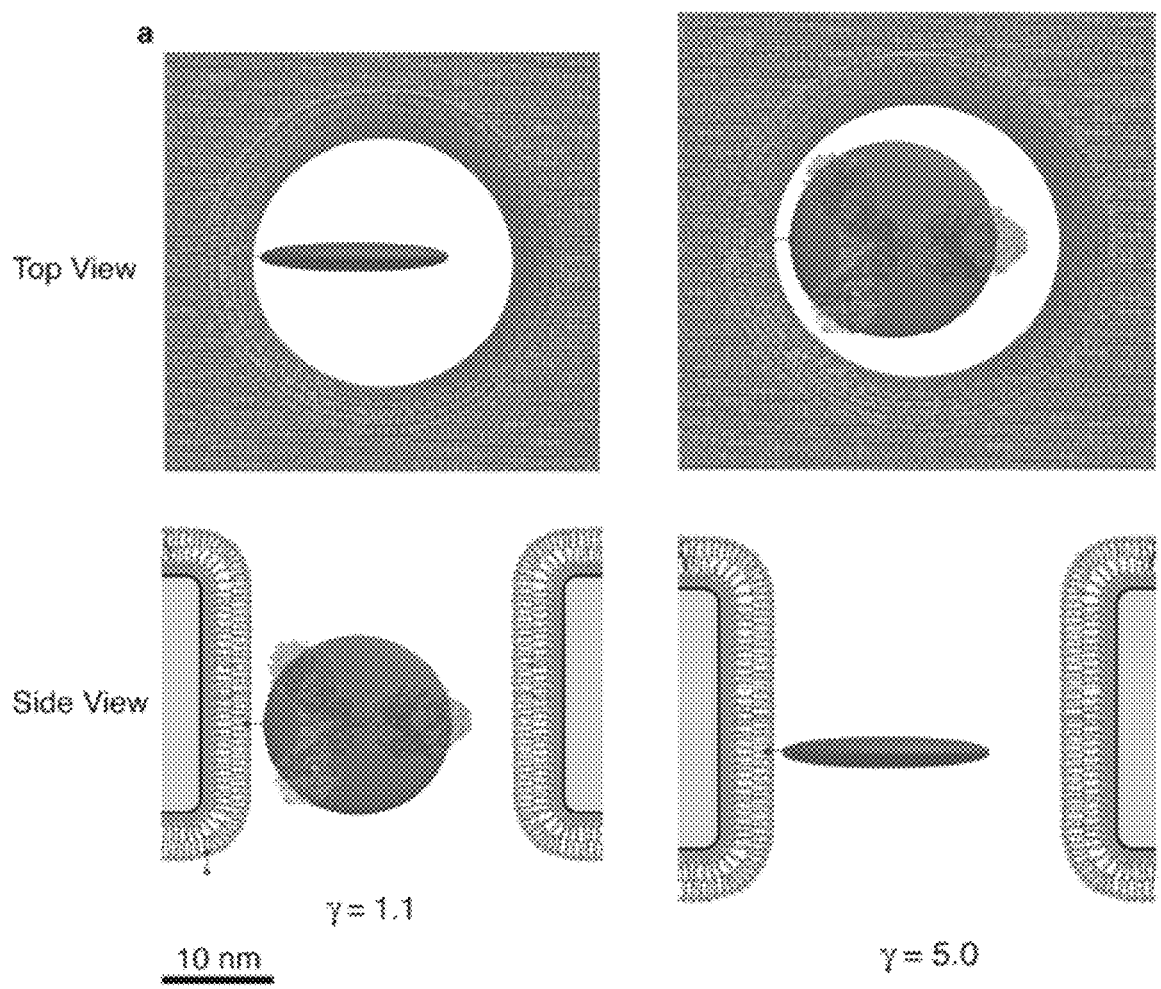
FIG. 25A  FIG. 25B

CONTROLLING TRANSLOCATION THROUGH NANOPORES WITH FLUID WALLS

CROSS-REFERENCE TO RELATED APPLICATIONS

This application is a continuation of U.S. application Ser. No. 15/157,591 filed on May 18, 2016, which is a continuation of U.S. application Ser. No. 13/400,472 filed on Feb. 20, 2012, now U.S. Pat. No. 9,347,929 issued May 24, 2016, which claims the benefit of U.S. Provisional Application No. 61/448,093 filed on Mar. 1, 2011. The entire disclosures of the above applications are incorporated herein by reference.

GOVERNMENT SUPPORT

This invention was made with government support under GM081705 awarded by the National Institutes of Health and DBET0449088 awarded by the National Science Foundation. The government has certain rights in the invention.

BACKGROUND

Synthetic nanopores enable fundamental and applied studies of individual biomolecules in high throughput; their performance is, however, subject to some limitations.

For example, recordings of resistive current pulses during the translocation of molecules through electrolyte-filled nanopores make it possible to study the size (1-6), conformation (7-8), and activity of single molecules in situ (11-17). This technique can characterize hundreds of unlabeled single molecules per second in physiological solutions and yields distributions of measured parameters from these single-molecule investigations (16,18). Nanopore-based experiments are relatively simple to set up, execute, and analyze, while providing unique information content including sub-molecular detail on the composition of individual molecules (18) and on the formation of molecular complexes or aggregates (2,19). In addition, nanopores hold tremendous promise for applied fields such as single-molecule binding assays (2,16,20), portable detection of (bio) warfare agents (4,5,21), and ultra-fast sequencing of DNA or RNA (22,23). In order to accelerate the realization of this potential, several challenges should be addressed; these include:

Difficulty to fabricate synthetic nanopores reliably on the (sub-) nanometer scale (24).
Difficulty to adjust or actuate the pore diameter, in situ (25,26).
Limited control of translocation times of single-molecule analytes, often leading to incomplete time resolution of translocation signals and associated inaccurate determination of the amplitude and duration of resistive pulses (27-29).
Limited control of the surface chemistry inside synthetic pores (16).
Non-specific interactions of analytes with the pore walls (2,6,30).
Pore clogging (16).
Low frequency of translocation events at low analyte concentrations (31); and
Poor specificity for analytes (16).

In conventional Coulter counting there are two liquid compartments with an electrode in each compartment and a pore connecting the compartments. The electrodes measure current or other electrical parameters, such as voltage, resistance, and capacitance, between the two compartments. When a particle from one of the liquid compartments enters the pore, it perturbs the electric field. The so-called Coulter effect is well-known and provides that the field is perturbed by a passage of a particle through the pore, and the effect is detectable and measurable especially when the pore and the particle are of comparable dimension. As the pore diameter decreases, smaller objects can be detected using the Coulter principle.

For detection, there must be a measureable change in an electrical parameter for each particle that passes through the pore. It has been theoretically and empirically found that the length of the pore is important, with the result that for small particles like a protein the pore must be very short in order to achieve enough perturbation in the electrical signal for it to be measured. So, for measuring nano-sized particles such as a protein, not only is a small diameter pore required but also a very short pore. Coulter counting of nano-sized particles has been limited by the fact that when a protein or other bio-molecule goes through or translocates through a short pore, the transit time is so short that the best available electronics cannot resolve the translocation.

A way of overcoming these and other drawbacks of using the Coulter principle on nano-sized analytes would be an advance.

REFERENCES FOR THE BACKGROUND SECTION

1. Robertson, J. W. F. et al., Single-molecule mass spectrometry in solution using a solitary nanopore, Proc. Natl. Acad. Sci., U.S.A. 104, 8207-8211 (2007).
2. Sexton, L. T. et al., Resistive-pulse studies of proteins and protein/antibody complexes using a conical nanotube sensor, J. Am. Chem. Soc. 129, 13144-13152 (2007).
3. Han, A. P. et al., Sensing protein molecules using nanofabricated pores, Appl. Phys. Lett. 88, 093901 (2006).
4. Han, A. P. et al., Label-free detection of single protein molecules and protein-protein interactions using synthetic nanopores, Anal. Chem. 80, 4651-4658 (2008).
5. Uram, J. D., Ke, K., Hunt, A. J. & Mayer, M., Submicrometer pore-based characterization and quantification of antibody-virus interactions, Small 2, 967-972 (2006).
6. Siwy, Z. et al., Protein biosensors based on biofunctionalized conical gold nanotubes, J. Am. Chem. Soc., 127, 5000-5001 (2005).
7. Ito, T., Sun, L. & Crooks, R. M., Simultaneous determination of the size and surface charge of individual nanoparticles using a carbon nanotube-based coulter counter, Anal. Chem. 75, 2399-2406 (2003).
8. Talaga, D. S. & Li, J. L., Single-molecule protein unfolding in solid state nanopores, J. Am. Chem. Soc. 131, 9287-9297 (2009).
9. Oukhaled, G. et al., Unfolding of proteins and long transient conformations detected by single nanopore recording, Phys. Rev. Lett. 98, 158101 (2007).
10. Benner, S. et al., Sequence-specific detection of individual DNA polymerase complexes in real time using a nanopore, Nat. Nanotechnol. 2, 718-724 (2007).
11. Macrae, M. X. et al., A semi-synthetic ion channel platform for detection of phosphatase and protease activity, ACS Nano 3, 3567-3580 (2009).
12. Clarke, J. et al., Continuous base identification for single-molecule nanopore DNA sequencing, Nat. Nanotechnol. 4, 265-270 (2009).
13. Zhao, Q. T., de Zoysa, R. S. S., Wang, D. Q., Jayawardhana, D. A. & Guan, X. Y., Real-time monitoring of 13. peptide cleavage using a nanopore probe, J. Am. Chem. Soc. 131, 6324-6325 (2009).
14. Hall, A. R., van Dorp, S., Lemay, S. G. & Dekker, C., Electrophoretic force on a protein-coated DNA molecule in a solid-state nanopore, Nano Lett. 9, 4441-4445 (2009).
15. Bayley, H. & Cremer, P. S., Stochastic sensors inspired by biology, Nature 413, 226-230 (2001).
16. Nakane, J. J., Akeson, M. & Marziali, A., Nanopore sensors for nucleic acid analysis, J. Phys. Condens. Matter 15, R1365-R1393 (2003).
17. Dekker, C., Solid-state Nanopores. Nat. Nanotechnol. 2, 209-215 (2007).
18. Martin, C. R. & Siwy, Z. S., Learning nature's way: Biosensing with synthetic nanopores, Science 317, 331-332 (2007).
19. Movileanu, L., Interrogating single proteins through nanopores: challenges and opportunities, Trends Biotechnol. 27, 333-341 (2009).
20. Howorka, S. & Siwy, Z., Nanopore analytics: sensing of single molecules, Chem. Soc. Rev. 38, 2360-2384 (2009).
21. Majd, S. et al., Applications of biological pores in nanomedicine, sensing, and nanoelectronics, Curr. Opin. Biotechnol. doi:10.1016/j.copbio.2010.1005.1002 (2010).
22. Griffiths, J., The realm of the nanopore, Anal. Chem. 80, 23-27 (2008).
23. Bayley, H. & Martin, C. R. Resistive-pulse sensing— from microbes to molecules, Chem. Rev. 100, 2575-2594 (2000).
24. Wanunu, M., Morrison, W., Rabin, Y., Grosberg, A. Y. & Meller, A., Electrostatic focusing of unlabelled DNA into nanoscale pores using a salt gradient, Nat. Nanotechnol. 5, 160-165 (2010).
25. Uram, J. D., Ke, K., Hunt, A. J. & Mayer, M., Label-free affinity assays by rapid detection of immune complexes in submicrometer pores, Angew. Chem.-Int. Edit. 45, 2281-2285 (2006).
26. Movileanu, L., Howorka, S., Braha, O. & Bayley, H., Detecting protein analytes that modulate transmembrane movement of a polymer chain within a single protein pore, Nat. Biotechnol. 18, 1091-1095 (2000).
27. Howorka, S., Nam, J., Bayley, H. & Kahne, D., Stochastic detection of monovalent and bivalent protein-ligand interactions, Angew. Chem.-Int. Edit. 43, 842-846 (2004).
28. Ding, S., Gao, C. L. & Gu, L. Q., Capturing single molecules of immunoglobulin and ricin with an aptamer-encoded glass nanopore, Anal. Chem. 81, 6649-6655 (2009).
29. Kasianowicz, J. J., Brandin, E., Branton, D. & Deamer, D. W., Characterization of individual polynucleotide molecules using a membrane channel, Proc. Natl. Acad. Sci. U.S.A. 93, 13770-13773 (1996).
30. Branton, D. et al., The potential and challenges of nanopore sequencing, Nat. Biotechnol. 26, 1146-1153 (2008).
31. Iqbal, S. M., Akin, D. & Bashir, R., Solid-state nanopore channels with DNA selectivity, Nat. Nanotechnol. 2, 243-248 (2007).

SUMMARY

It has now been surprisingly discovered that improved resolution and detection of nanoparticles is achieved when a nanopore connecting liquid compartments in a device running on the Coulter principle is provided with fluid walls. A fluid wall is provided when a substrate is provided with a fluid coating. A fluid coating in turn is one in which the diffusion coefficient, measured for example by a conventional FRAP (fluorescence recovery after photobleaching) technique is sufficiently high to provide the noted benefits. In one embodiment, a fluid wall is one in which the measured diffusion coefficient measured by FRAP is at least $10^{-18}$ m$^2$ sec$^{-1}$, at least $10^{-16}$ m$^2$ sec$^{-1}$, at least $10^{-14}$ m$^2$ sec$^{-1}$, or at least $10^{-12}$ m$^2$ sec$^{-1}$. Where the fluid lipid walls are made of a lipid monolayer or a lipid bilayer, they can include lipid anchored mobile ligands as part of the lipid bilayer. By varying the nature and concentration of the mobile ligand in the lipid bilayer, multifunctional coatings of lipids are provided that confer unprecedented capabilities to nanopore based sensors. For example, bilayer coatings make it possible to fine tune and actuate pore diameters in sub-nanometer increments. Incorporating lipid anchored mobile ligands confers specificity and slows down the translocation of targeted proteins sufficiently to time resolve translocation events of individual proteins.

In other aspects, advantages are provided because the fluid coatings prevent pore clogging and enable translocation experiments with proteins, peptide oligomers, fibrils, nucleic acids, and other biomolecules. Use of biocompatible fluid coatings described herein nearly eliminates non-specific binding and makes it possible to distinguish proteins by combined analysis of translocation time, volume, charge, shape, ligand affinity, and so on.

In an illustrative embodiment, a device and a method of use is provided. The device provides for measuring the volume of a biomolecule and for counting the passage of each biomolecule using the Coulter principle as is conventional in Coulter counting. The device includes a first liquid compartment, a second liquid compartment, and a synthetic nanopore disposed between the compartments. The nanopore defines a fluid conduit from the first liquid compartment and the second liquid compartment and provides a path for molecules or other nanoparticles in the first compartment to flow to the second compartment. The device also includes electrodes in both liquid compartments and means for controlling the electrodes to measure electrical resistance, voltage difference, or ionic current flow between the first and second electrodes. In an advance for application in so-called nano-Coulter counting, the synthetic nanopore providing a fluid path between the first and second liquid compartments is lined with a fluid wall. In one embodiment, the fluid wall comprises a lipid bilayer. In another, the fluid wall comprises a lipid monolayer. In an exemplary embodiment, a dimension of the synthetic nanopore perpendicular to the fluid flow direction is sub-micrometer, for example on the order of 10 to 500 nm. In preferred embodiments, the dimension is 10 to 50 nm, or 20 to 30 nm.

The length of the fluid path between the first and second liquid compartments, in the fluid flow direction, is about 10 to about 1000 nm, in an exemplary embodiment. For example, the length is about 10 to 300 nm.

A fluid lipid wall lining the nanopore of the Coulter counting device is made of a lipid bilayer, which can include lipid anchored ligands. Exemplary lipids in the bilayer are phospholipids.

A method of using the device involves introducing a solution containing biomolecules into the first liquid compartment. The nanopore connects the first liquid compartment to the second liquid compartment, enabling dissolved molecules to move through the nanopore. As molecules flow through the nanopore, the electric field is perturbed, providing a time based perturbation of the electric field. In one aspect, these perturbations are analyzed according to known principles to provide various measured parameters of the biomolecule, including volume, concentration, and so on. In another aspect, advantage is taken of the fluid walls to measure charge on translocating molecules for the first time. Disclosure of this aspect is provided in non-limiting fashion in Example 5 below.

Lipid-coated, synthetic nanopores are multifunctional, fluid, and self-assembling. This meets many of the unmet challenges in nanopore sensing and is particularly beneficial in the context of single-molecule studies of native proteins. For example, the fluidity of the coating enables capture and concentration of proteins from dilute solutions and permits translocation of lipid-anchored proteins at frequencies that reveal information about their affinity to ligands on these lipid anchors. Fluid coatings also eliminate non-specific adsorption of proteins to the synthetic walls of the pore, since the surface is fluid, involved in molecular motion, and self-repairing. This effect permits translocating captured proteins on top of a fluid, biocompatible coating such as a lipid bilayer and establishes a predictable, quantitative relationship between translocation times and the charge of individual proteins. The viscous character of the fluid coating slows the translocation speed of lipid-anchored proteins and makes it possible to introduce selectivity for specific biomolecules while resolving translocation events completely in time. These viscous coatings therefore enable accurate quantitative analyses of the molecular volume and qualitative analyses of the shape of individual proteins. The anti-fouling character of fluid coatings made it possible to translocate aggregated forms of disease-relevant amyloid-β (Aβ) peptides through the pore without clogging. This capability permits analyses of the diameter, length, and volume from a large number of individual Aβ oligomers and fibrils during their aggregation in situ.

DRAWINGS

The drawings described herein are for illustrative purposes only of selected embodiments and not all possible implementations, and are not intended to limit the scope of the present disclosure.

FIG. 1A, FIG. 1B, FIG. 1C, and FIG. 1D illustrate synthetic nanopores with bilayer-coated fluid walls. FIG. 1A) Cartoon showing a cross-section through one sensillum in the antenna of the silk moth *Bombyx mori*. Capture, pre-concentration, and translocation of pheromones through the exoskeleton of these sensilla towards dendrites of olfactory neurons is thought to occur via lipid-coated nanopores and pore tubules[32-34]. FIG. 1B) Cartoon, drawn to scale, showing a synthetic, lipid-coated (yellow) nanopore in a silicon nitride substrate (grey) and the interstitial water layer (blue). FIG. 1C) Nanopore resistance and corresponding open pore diameter as a function of the thickness of the bilayer coating[38]. Red curve is a best fit of the data to equation (1). Numbers underneath the lipid cartoons refer to the number of carbons in their acyl chains (see Table 1). FIG. 1D) Actuation of nanopore diameters by a change in the thickness of the bilayer coating, Δd, in response to a thermal phase transition of DMPC lipids (see Supplementary Section S1). Blue dotted line and grey shaded region represent the mean value and range of phase transition temperatures reported for DMPC lipids[39]. Inset: cycling the temperature between 13° and 27° C. actuated the pore diameter dynamically as indicated by the larger changes in electrical resistance through a pore with (green squares) than without (back squares) a bilayer.

FIG. 2A, FIG. 2B, and FIG. 2C capture affinity-dependent pre-concentration, and translocation of specific proteins after binding to ligands on mobile lipid anchors. FIG. 2A) Cartoon, drawn to scale, illustrating binding of streptavidin (large particles) to specific lipid-anchored biotin-PE (small circles) followed by single molecule translocation of the anchored complex through the nanopore. FIG. 2B) Current versus time traces illustrating capture, pre-concentration, and reduced translocation speed of streptavidin. In the absence of biotin groups, only rare translocation events with short translocation times, $t_d$, could be detected in electrolytes containing 6 pM streptavidin (top current trace). In contrast, 0.4 mol % of biotinylated lipids in the lipid coating strongly increased the event frequency and slowed down the translocation speed sufficiently to enable complete time resolution of translocation events (bottom current trace). FIG. 2C) Minimum bulk concentrations of streptavidin, polyclonal anti-biotin Fab fragments, and monoclonal anti-biotin IgG antibodies required to observe at least 30-100 translocation events per second.

FIG. 3A, FIG. 3B, and FIG. 3C illustrate controlling the translocation times, $t_d$, of single lipid-anchored proteins by the viscosity of the bilayer coating and distinguishing proteins by their most probable $t_d$ values. FIG. 3A) Distribution of translocation times of streptavidin. Insets: current versus time traces illustrating that $t_d$ could be prolonged more with intermediate viscosity POPC bilayers (bottom current traces) than with low viscosity DAPPC bilayers (top current traces). FIG. 3B) Translocation of anti-biotin Fab fragments through nanopores with bilayers of intermediate viscosity (POPC) or high viscosity (~49 mol % cholesterol and 50 mol % POPC). FIG. 3C) Translocation of anti-biotin antibodies through a pore with a coating of intermediate viscosity (POPC). Curves represent a best fit of the corresponding data to a biased diffusion first passage time model[14] (equation S10 in Supplementary Section S5). All bilayers contained 0.15-0.4 mol % biotin-PE. See Supplementary Sections S7 and S9 for binning methods, errors of $t_d$, and measurement errors.

FIG. 4A, FIG. 4B, and FIG. 4C illustrate distribution of ΔI values and corresponding molecular volumes and shape factors of individual proteins translocating through bilayer-coated nanopores with biotinylated lipids. FIGS. 4A-4C, Translocation of streptavidin (FIG. 4A), anti-biotin Fab fragments (FIG. 4B) and anti-biotin antibodies (FIG. 4C); the dashed vertical lines indicate ΔI values that would be expected for IgG antibodies with a volume of 347 nm³ and different shape factors γ; see Supplementary Section S6 for a schematic illustration and discussion of shape factors[52,55].

FIG. 5 is a comparison of experimental and theoretical values of charge-dependent translocation times of streptavidin. Experimental values are shown in black squares and the curve represents the theoretical prediction by equation 3. Dashed black line corresponds to the expected translocation time for streptavidin assuming a translocation event due purely to diffusion in one dimension ($t_d = l_p^2$ (2$D_L$), i.e. without an electrophoretic effect. The valence |z| of the net charge of streptavidin was varied by the pH of the electrolyte[56]. The length of the pore with the bilayer coating was 28±0.2 nm. Note that the curve is not a best fit to the data; it is the prediction of $t_d$ as a function of |z| according to equation (3) when all parameters were fixed to their known values.

FIG. 6A and FIG. 6B illustrate bilayer-coated nanopores that resist clogging and enable the monitoring of the aggregation of amyloid-beta (Aβ) peptides. FIG. 6A, Cartoon illustrating clogging of uncoated nanopores and a typical current versus time trace during clogging of a nanopore by Aβ aggregates. This concatenated current trace shows several 1 s recordings and one 5 min recording. FIG. 6B, Cartoon illustrating translocation of individual Aβ aggregates through a bilayer-coated nanopore with a fluid wall (white arrow in the inset) and a typical current versus time trace of translocation events. The bilayer coating conferred non-fouling properties to these pores and enabled resistive pulse recordings over at least 40 min without clogging. Both recordings are 5 s long, one was taken immediately after addition of the Aβ sample and the other one 40 min later. Aβ (1-40) samples were aggregated for 72 h.

FIG. 7 is a diagram of a device operating under the Coulter principle. References in the captions of FIGS. 8-12 are those listed in Example 7.

FIG. 8A and FIG. 8B—Nanopores with fluid walls make it possible to characterize Aβ aggregates by resistive pulse recordings. FIG. 8A. Illustration of the experimental setup with fluid access channels to a nanopore embedded in a silicon nitride chip.[54,55] Silver-silver/chloride electrodes immersed in the two fluidic compartments are connected to a patch-clamp amplifier and used to measure the ionic current through the nanopore. Inset left. Cartoon showing a cross-section of a nanopore that is coated with a fluid lipid bilayer, thereby enabling the translocation of Aβ aggregates without clogging of the pore. Inset right. Original current trace showing a characteristic resistive pulse with the parameters $\Delta I$ and $t_d$. FIG. 8B. Original current traces recorded before adding Aβ, after adding Aβ that was permitted to aggregate for 1 or 3 days. The nanopore had a length of 18 nm and a diameter of 28 nm before the lipid bilayer coating (length of 28 nm and a diameter of 18 nm after the bilayer coating).

FIG. 9A and FIG. 9B—scatter plots of $\Delta I$ values versus $t_d$ values from the translocation of individual Aβ aggregates reveal clusters of translocation events due to spherical oligomers, protofibrils with lengths shorter than the length of the nanopore, protofibrils with lengths longer than the length of the nanopore, and mature fibers. FIG. 9A) Scatter plots of $\Delta I(t_d)$ from aggregates of $A\beta_{(1-40)}$ that were analyzed after 0, 1, 2, and 3 days of incubation. FIG. 9B) Scatter plot of all data combined and color coded according to the results from statistical cluster analysis.[56]

FIG. 10A, FIG. 10B, FIG. 10C, and FIG. 10D show a transmission electron microscopy (TEM) analysis of the size of $A\beta_{(1-40)}$ aggregates. FIG. 10A. Micrographs showing aggregates with increasing size after incubation in water for 0, 1, 2 and 3 days. FIG. 10B & FIG. 10C. Histograms of the diameters (FIG. 10B) and lengths (FIG. 10C) of all aggregates that were not mature fibers. Inset in FIG. 10C. Proportion of aggregates with lengths longer than 10 nm and 45 nm. FIG. 10D. Boxplots characterizing mature fibers after three days of aggregation. The fibers were characterized by their apparent widths when lying flat $w_2$ (red arrows in FIG. 10A) on the TEM grid and when twisted or crossing over themselves $w_1$ (blue arrows in FIG. 10A) on the TEM grid.[22] The box represents the range between the $1^{st}$ and $3^{rd}$ quartiles, the dashed line represents the median, the dot is the mean, and the whiskers extend to the range of the data (minimum and maximum values) except for outliers, which are plotted as "x".

FIG. 11 is estimated lengths of $A\beta_{(1-40)}$ protofibrils in clusters (i) and (ii). The lengths of protofibrils were estimated by solving a system of equations for $\Delta I$ ($\gamma$, $l_M$) and $\gamma$ ($l_M$) and assuming that all aggregates were cylindrical. The dotted lines indicate the location of local maxima in the size distributions of $A\beta_{(1-40)}$ predicted by Cabriolu et al. The local maxima of the Gaussian fits to the data are located at: 5.3, 7.0, 10.3, 13.5, and 19.9 nm. Note that the two histograms have different bin-widths and are not normalized.

FIG. 12 consists of frequency of translocation events organized by cluster classification reveal time-dependent aggregation. Mean values and standard deviations were calculated by counting the number of translocation events within a given cluster classification during several recordings totaling 40-100 s in duration.

FIG. 13A and FIG. 13B Schematic cross-section of the silicon chip and of the nanopore with the channel leading to the pore. FIG. 13A) Silicon chip (dark) with a silicon nitride layer (gray) on the top; the free-standing part of this Si3N4 layer constitutes a window with a nanopore and with a channel through the silicon nitride that leads to the pore. FIG. 13B) Schematic illustration of this channel with a length $l_C$ of 258±9 nm and a radius $r_C$ of 50±7.5 nm, which led to a nanopore with radii $r_P$ of 16-50 nm and lengths 1p of 12-22 nm, depending on the chip. Schematic illustration of a lipid bilayer coating with a thickness d and a water layer between the bilayer and the chip with a thickness wL; this bilayer coating increases the effective length of the nanopore to lP'=lP+2(wL+d) and reduces the effective radius to rP'=rP−wL−d.

FIG. 14A, FIG. 14B, FIG. 14C and FIG. 14D illustrate transmission electron micrographs of several nanopores used in this work. The brightest part in the center of each image depicts the shape and size of the nanopore and the surrounding circle with reduced brightness reflects the channel leading to the nanopore. All scale bars are 50 nm. FIG. 14A) Pore used for experiments with bilayers that contained lipids with different acyl-chain lengths (<rP>=14 nm, lP=12 nm, rC=48 nm, and lC=264 nm).

FIG. 14B) Pore used for sensing streptavidin (<rP>=9.6 nm, lP=18 nm, <rC>=49 nm, and lC=258 nm). FIG. 14C) Pore used for sensing monoclonal anti-biotin antibody and anti-biotin antibody Fab fragment (<rP>=16.5 nm, lP=22 nm, <rC>=53 nm, and lC=255 nm). FIG. 14D) Pore used for sensing aggregates of Aβ peptides. For these experiments, the channel created by a focused ion beam without sculpting was used as the pore (<rP>=48 nm and lP=275 nm; rC=0 and lC=0). Notation of a radius as <r> indicates an area-equivalent radius calculated with equations (S4) or (S5). All dimensions refer to the pores before bilayer coating.

FIG. 15 is shrinking and actuating the diameter of bilayer-coated nanopores with temperature. Resistance as a function of temperature in a nanopore coated with a bilayer of DMPC lipids, (circles), and in a pore without a bilayer coating, (squares). The bottom curve (-) represents a physical model based on equations (S3), (S7), and (S8) and described the resistance through the uncoated nanopore. Inclusion of the bilayer thickness, d, as a fitting parameter by employing equations (S6)-(S8) described the resistance through a bilayer coated-nanopore in the temperature range from 280 K to 290 K (top curve, R2=0.95, N=5) and in the temperature range from 300 K to 310 K (middle curve, R2=0.97, N=5). The dimensions of the nanopore before bilayer formation were rP=13 nm, lP=28 nm, rC=50 nm, and lC=247 nm. The recording buffer contained 500 mM KCl and 10 mM HEPES (pH 7.4±0.1), and the applied potential difference was ±0.1 V.

FIG. 16A, FIG. 16B, FIG. 16C, and FIG. 16E describe fluorescence micrographs of Si—Si3N4 chips with a supported lipid bilayer containing Rh-PE lipids and corresponding line scans. FIG. 16A) Epifluorescence micrograph with a line scan to quantify the fluorescence intensity along the path shown by the solid white line. This pore had an area-equivalent diameter of 33.5 nm and a length of 22 nm without the bilayer coating. FIG. 16B) Plot of fluorescence intensity as a function of position along the line scan. The numbers 1-4 correspond to the numbers in FIG. 16A to the location on the chip indicated in the schematic illustration FIG. 16C. FIG. 16E) Additional epifluorescence micrographs showing the diffraction limited spot at the location of the nanopore. Line scans were measured from the opposite corners of the silicon nitride window similar to that in panel FIG. 16A. From top to bottom these pores had area-equivalent diameters of 31 nm, 33.5 nm, and 20 nm; and lengths of 20 nm, 22 nm, and 18 nm. All bilayers were labeled with 0.8 mol % Rh-PE. All scale bars correspond to 10 μm.

FIG. 17A and FIG. 17B describe fluorescence micrographs for determining bilayer fluidity by fluorescence recovery after photobleaching (FRAP) experiments. FIG. 17A, Epifluorescence micrographs indicating the recovery of fluorescence in a photobleached spot of the lipid bilayer on the Si—Si3N4 chip. FIG. 17B, Plot of intensity versus time from two separate FRAP experiments on a chip that was coated with a bilayer containing 98.8 mol % POPC (■) or with 98.8 mol % DΔPPC (●). The larger t½ value for POPC lipids compared to DΔPPC lipids indicated the increased viscosity of POPC bilayers compared to DΔPPC bilayers. All bilayers were labeled with 0.8 mol % Rh-PE and contained 0.4 mol % of 1,2-dipalmitoyl-sn-glycero-3-phosphoethanolamine-N-(cap biotinyl) (biotin-PE) because the same chips were later used to sense the translocation of streptavidin (FIG. 3A and FIG. 4A). Images in a were both contrast enhanced to the same extent to increase clarity. The scale bars correspond to 25 μm.

FIG. 18A and FIG. 18B describe fluorescence micrographs of silicon-nitride windows with a nanopore after exposure to fluorescently labeled-streptavidin. FIG. 18A, Fluorescence micrograph taken of the silicon nitride window after physisorption of streptavidin-TRITC onto a chip that was cleaned with a fresh 3:1 mixture of concentrated sulfuric acid and a 30% (v/v) hydrogen peroxide solution (Piranha solution). The line scan beneath the image corresponds to the intensity of fluorescence along a diagonal path across the silicon nitride window through the location of the nanopore at its center. FIG. 18B, Fluorescence micrograph taken of the same silicon nitride window but after formation of a supported lipid bilayer of POPC lipids followed by incubation with streptavidin-TRITC. The line scan beneath the image corresponds to the intensity of fluorescence along a diagonal path across the silicon nitride window through the location of the nanopore at its center. The nanopore for these experiments had an area-equivalent diameter of 110 nm and a length of 275 nm. Scale bars correspond to 10 μm. The same camera and exposure settings were used to acquire both images.

FIG. 19A, FIG. 19B, FIG. 19C and FIG. 19D contain power spectra of the electrical current noise from chips with a bilayer coating and from chips without a bilayer coating. FIG. 19A, FIG. 19B, Power spectra of the noise before and after formation of supported lipid bilayers from two different lipids on the same chip while a voltage of −0.1 V was applied. The nanopore had a diameter of 28 nm before formation of the supported lipid bilayer (FIG. 19A, POPC lipids; FIG. 19B, DΔPPC lipids). In FIG. 19B, the current recording was recorded with the hardware filter of the amplifier set to a cut-off frequency of 2 kHz. FIG. 19C, FIG. 19D, Power spectra of the noise from two independent experiments with a chip containing a very small area-equivalent diameter of 9 nm, which was too small for the formation of a lipid bilayer inside the nanopore. In FIG. 19D, the current recording was recorded with the hardware filter of the amplifier set to a cut-off frequency of 2 kHz. The electrolyte for all recordings contained 500 mM KCl and 10 mM HEPES with a pH of 7.4±0.1.

FIG. 20—Nanopore coatings with increasing mole fractions of negatively charged lipids reduce the resistance of the nanopore in electrolytes with low ionic strength. The supported lipid bilayers were formed from liposomes with the indicated mole fractions, $X_{P4}$, of DOPA lipids with a background of POPC lipids. The pore used for these experiments had a diameter of 28 nm before the bilayer coating. The electrolyte had an ionic strength of ~2.5 mM and contained 750 μM $CaCl_2$ and 250 μM KCl with a pH of ~7.

FIG. 21 describes charges on the surface of a pore with a diameter of 0.5 μm did not significantly affect the permeation of ions, and hence resistance, through the pore. Currents were measured as a function of applied potential difference through a conical pore (tip diameter 500 nm) without a bilayer (■), through the same pore with an electrically neutral bilayer coating of POPC lipids (▲), and through the same pore with a bilayer coating containing 40 mol % of negatively charged lipids (✦). The recording electrolyte was the same as in Fig. S8.

FIG. 22A, FIG. 22B, and FIG. 22C are bar graphs comparing the frequency of resistive pulses due to the translocation of streptavidin, anti-biotin mAb, and anti-biotin Fab fragments through bilayer-coated nanopores with biotin-PE lipids and respective control experiments. FIG. 22A, Frequency of resistive pulses due to translocation of SA through a nanopore with a bilayer coating that contained biotin-PE lipids and after exchanging the electrolyte for 3 h to remove SA from solution compared to a coating without biotin-PE lipids (in this case the frequency of events was 0.09 $s^{-1}$ and is too low to be seen as a bar). FIG. 22B, Frequency of resistive pulses due to the translocation of anti-biotin mAb through a nanopore with a bilayer coating that contained biotin-PE lipids compared to the same experiment after adding 10 μM of soluble biotin to the solution and compared to an experiment with a nanopore coating that did not contain biotin-PE lipids. FIG. 22C, Frequency of resistive pulses due to the translocation of anti-biotin Fab through a nanopore with a bilayer coating that contained biotin-PE lipids compared to a coating without biotin-PE lipids. The concentrations of the proteins are shown above the bars. Bilayers were formed from ~99 mol % POPC, 0.8 mol % Rh-PE, and if indicated, 0.15 mol % biotin-PE.

FIG. 23A, FIG. 23B, and FIG. 23C are a description of detection of monoclonal anti-biotin $IgG_1$ antibody (mAb) with a bilayer-coated nanopore. FIG. 23A, Current versus time trace showing resistive pulses due to translocation of mAbs that were bound to biotin-PE lipids in the bilayer coating and analysis of $t_d$ and ΔI of the corresponding resistive pulses. Resistive pulses occurred at a frequency of 34 $s^{-1}$. FIG. 23B, Current versus time trace recorded after the addition of excess biotin (10 μM) to the solution, illustrating the reduced frequency of resistive pulses (1.3 $s^{-1}$) and analysis of $t_d$ and M of the corresponding resistive pulses. FIG. 23C, Current versus time trace recorded using the same nanopore as a and b but with a bilayer coating that did not contain biotin-PE lipids, illustrating the reduced frequency (2 $s^{-1}$) of resistive pulses even at a concentration of mAb of 25 nM and analysis of $t_d$ and ΔI of the corresponding resistive pulses. Distributions of $t_d$ values were fit with equation (S10) as described in Supplementary Section S5.4 and S7.1. Bilayers were formed from ~99 mol % POPC, 0.8 mol % Rh-PE, and if indicated, 0.15 mol % biotin-PE. The experiments were performed with the nanopore shown in FIG. 14C. The recording buffer contained 2.0 M KCl and 10 mM HEPES buffered at a pH of 7.4±0.1, and currents were recorded at an applied potential difference of −0.1 V.

FIG. 24A, FIG. 24B, FIG. 24C, and FIG. 24D describe viscosity of bilayers which can slow the translocation of anti-biotin Fab fragments that are bound to biotin-PE lipids permitting time-resolved determination of the peak amplitude of resistive pulses. FIG. 24A, Current traces showing resistive pulses due to the translocation of Fab fragments through the nanopore. Resistive pulses were observed at a frequency of ~100 s$^{-1}$ with bilayer coatings that contained biotin-PE, whereas bilayer coatings without biotin-PE resulted in resistive pulses at a frequency of 2 s$^{-1}$. FIG. 24B, Individual resistive pulses from translocation of Fab fragments through a bilayer-coated nanopore containing 99.2 mol % POPC and 0.8 mol % Rh-PE in the bilayer coating (but no biotin-PE) and analysis of $t_d$ and $\Delta I$ of these resistive-pulses. FIG. 24C, Individual resistive pulses from translocation of Fab fragments through a bilayer-coated nanopore containing 0.15 mol % biotin-PE, ~99 mol % POPC, and 0.8 mol % Rh-PE and analysis of $t_d$ and $\Delta I$ of these resistive-pulses. FIG. 24D, Individual resistive-pulses from translocation of Fab fragments through a nanopore coated with a bilayer of increased viscosity (containing 0.15 mol % biotin-PE, 49.5 mol % POPC, 49.5 mol % cholesterol, and 0.8 mol % Rh-PE) and analysis of $t_d$ and $\Delta I$ of these resistive-pulses. Distributions of $t_d$, except the incomplete distribution in FIG. 24B, were fit with equation (S10) as described in Supplementary Section S5.4 and S7.1. The experiments were performed with the nanopore shown in FIG. 24C. The recording buffer contained 2.0 M KCl and 10 mM HEPES buffered at a pH of 7.4±0.1. Currents were recorded at an applied potential difference of −0.1 V.

FIG. 25A and FIG. 25B illustrate two extremes of possible orientations of an IgG antibody, approximated by an oblate spheroid, during its translocation through a nanopore. FIG. 25A, Cartoon illustrating the translocation of an oblate spheroid with its pole-to-pole axis oriented perpendicular to the length axis of the pore; this orientation would result in a shape factor, γ, of 1.1. FIG. 25B, Illustration of the same oblate spheroid as in FIG. 25A but translocating through the pore with its equatorial axis oriented perpendicular to the length axis of the pore; this orientation would result in a shape factor, γ, of 5.0. Note that the illustration is drawn to scale and that the nanopore was drawn to match the dimensions of the pore used for the experiments in FIG. 4C of the main text. A scaled space-filling model of an IgG antibody[30] with a volume of 347 nm$^3$ overlays the oblate spheroid with the same volume.

FIG. 26A and FIG. 26B—Translocation of non-spherical lipid-anchored streptavidin-IgG complexes resulted in broad distributions of $\Delta I$ due to the various orientations the complex could assume inside the nanopore. FIG. 26A, Distributions of $\Delta I$ and $t_d$ resulting from the translocation of streptavidin while bound to biotin-PE lipids in the bilayer coating of a nanopore. FIG. 26B, Distributions of $\Delta I$ and $t_d$ after the addition of a biotinylated polyclonal, IgG antibody against catalase. Note that before recording resistive pulses, the electrolyte solutions were thoroughly rinsed to remove unbound proteins from the solution. The bilayer coating in this experiment contained 0.15% biotin-PE, 0.8% Rh-PE, and ~99% POPC. The nanopore had a diameter of 36 nm and a length of 26 nm with the bilayer coating.

FIG. 27 is cumulative distributions of $t_d$ obtained from translocation events of mAb at different applied voltages. Distributions of $t_d$ values were determined from recording translocation events of mAb while applying potential differences of 120 mV (upper curve -), 100 mV (second curve from top -), 80 mV (middle curve -), 70 mV (second curve from bottom -), and 60 mV (lower curve -) across the chip. The inset shows the distributions over the range of $t_d$ values of 20 μs to 150 μs. Best curve fits of this data to equation (S13) determined the most probable values of $t_d$ ($t_{d,\,mp}$) in order of decreasing applied potential difference: 40 μs, 43 μs, 60 μs, 67 μs, and 90 μs.

FIG. 28A, FIG. 28B, and FIG. 28C describe effect of different bin-widths for determining the most frequently observed value of $t_d$ based on best curve fits of $t_d$ data in histograms to equation (S14). Different bin-widths of FIG. 28A) 15 μs, FIG. 28B) 30 μs, and FIG. 28C) 50 μs were used to produce these histograms from $t_d$ values that were measured from translocation events of streptavidin in an electrolyte with pH=6.6. These $t_d$ histograms were fit with equation (S14) using the non-linear curve fitting function of the software OriginPro 8 with its so called "Extreme Function".

FIG. 29 describes most probable $t_d$ values for the monoclonal anti-biotin IgG$_1$ antibody (mAb) as a function of the voltage drop, $V_P$, across a bilayer-coated nanopore containing biotin-PE. The red curve was obtained by a best fit of equation (S18) to the data with z as the only fitting parameter. The fit returned a value for z of −4.2±0.5 with $R^2$=0.94 (N=8). The error bars of the most probable $t_d$ values in this plot are likely overestimates that are based on an 1p of ±1 nm since all of these recordings were performed on the same chip with the same bilayer and the variations in 1p between current recordings are more likely to be ±0.2 nm due to fluctuations in the thickness of the water layer and lipid bilayer. The bilayer coating in this experiment contained 0.15% biotin-PE, 0.8% Rh-PE, and ~99% POPC. After the bilayer coating, the nanopore had a diameter of 36 nm and a length of 24 nm.

FIG. 30A, FIG. 30B, and FIG. 30C contain a capillary electropherograms for determining the charge of the proteins used in this work. FIG. 30A, FIG. 30B, Electropherograms obtained with a CE instrument equipped with UV detection. Protein samples were prepared in PBS at pH 7.4 and included the neutral marker, 4-methoxybenzyl alcohol. The neutral maker appeared at 15-15.5 min and is labeled in the figure. Peaks due to the protein are shown in red and the time of each peak's maxima is indicated in the figure. The capillary was a fused silica capillary with a total length of 64.5 cm and an internal diameter of 50 μm. The length of the capillary to the detector was 56 cm and the total applied voltage was 15 kV. The temperature of the capillary was maintained at 25° C. FIG. 30C) Electropherogram obtained with a CE instrument equipped with fluorescence excitation at 490 nm and detection at 540 nm. The protein sample was prepared in PBS at pH 7.4 and included the zwitterionic fluorophore, rhodamine B, which served as the neutral fluorescent marker. The sample contained 1.8 μM of the anti-biotin IgG mAb and 0.5 μM of biotin-5-fluorescein, with a net charge of z=−1. The capillary was a fused silica capillary with a total length of 30 cm and an internal diameter of 50 μm. The length of the capillary to the detector was 20 cm and the total applied voltage was 7.0 kV. The temperature of the capillary in FIG. 30C was maintained at 28° C. Note that in all cases, the baseline of the electropherograms were adjusted.

FIG. 31A and FIG. 31B are a characterization of $t_d$ and $\Delta I$ for pulses of various simulated translocation times resulting from an input from a waveform generator. FIG. 31A. Measured values for the pulse magnitude, $\Delta I$, of pulses input into the headstage with a waveform generator. The dotted line denotes the value of $t_d$ at which $\Delta I$ was attenuated by 3% (~50 µs). FIG. 31B. Measured values for the pulse duration of pulses input into the headstage with a waveform generator show that $t_d$ could be accurately determined if it exceeded a threshold value of ~25 µs. Therefore the lower limit of accurate quantification of $t_d$ values was 25 µs. The line is plotted with a slope equal to 1.

FIG. 32 is histograms of $t_d$ values measured from current pulses with defined duration and added electrical noise from resistive pulse experiments. Current pulses with precisely defined durations of 30, 50, 70, 100, 120, 140, and 160 µs were combined with electrical noise from a resistive-pulse experiment and the duration of these pulses was determined by their half-width. The red lines were obtained by fitting the histograms with a Gaussian distribution. From these fits, the measurement error of $t_d$, at, was determined to be 2.3, 4.0, 3.4, 3.9, 3.2, 3.2, and 3.4 µs (listed in order of increasing pulse duration).

FIG. 33 is gel electrophoresis results showing aggregation of amyloid-beta (residues 1-40) as a function of incubation time in water. Lane 1 (0 h), containing a solution of freshly prepared $A\beta_{(1-40)}$, shows that initially most of the $A\beta$ peptides in solution were monomers with a molecular weight of ~4 kDa. Lanes 2 (24 h), 3 (48 h), and 4 (72 h) show that as $A\beta$ aggregated in solution for increasing times, it formed aggregates of large molecular weight (6-250 kDa). Furthermore, lanes 2 and 3 show a population with a very large molecular weight (greater than 250 kDa) that remained in the wells of the polyacrylamide gel as it would be expected for fibrillar aggregates. The inset shows the same gel but exposed for 180 s and reveals that aggregates of large molecular weight (greater than 250 kDa), which remained in the well of the gel, were already present after 24 h of aggregation (lane 2). The molecular weight markers were See Blue Plus2 Stained Standard Markers from Invitrogen.

FIG. 34 is nanopores without a fluid lipid coating clogged after adding $A\beta_{(1-40)}$. Plot of eight concatenated, 20 sec, current versus time traces. The time gap between current traces is not to scale. The elapsed time between adding $A\beta_{(1-40)}$ (0.025 mg×mL$^{-1}$ in the top solution compartment) and the last current trace is 231 s, and the average time interval between recordings was 15 s. Before adding $A\beta_{(1-40)}$, the current was −52 nA, and after adding $A\beta_{(1-40)}$ the current decreased to ~−25 nA. The gradual decrease of the current was due to adsorption of $A\beta$ on the nanopore walls while the stepwise changes in current presumably indicate the adsorption and desorption of large aggregates. Note that after a few seconds, reliable analysis of $A\beta$ aggregates cannot be performed, and after two minutes, no more resistive-pulses can be observed. This experiment proceeded under identical conditions to those reported in the main text with the exception that the nanopore was not coated with a lipid bilayer. The $A\beta_{(1-40)}$ sample had been permitted to aggregate in pure water for ~3 h prior to the experiment. The applied electric potential difference was −0.2 V.

FIG. 35 shows that nanopores with a fluid lipid coating do not clog after adding $A\beta_{(1-40)}$ thereby permitting characterization of aggregates. Plot of four concatenated current traces that are each 20 s in duration. The time gap between current traces is not to scale. The elapsed time between adding $A\beta_{(1-40)}$ (0.0125 mg×mL$^{-1}$ in the top solution compartment) and the last current trace is 180 s. This $A\beta_{(1-40)}$ sample had been permitted to aggregate in pure water for one day prior to the experiment. Bilayer-coated nanopores remain usable for sensing resistive-pulses of $A\beta$ aggregates for at least 1.5 h.[1]

Figure 38:
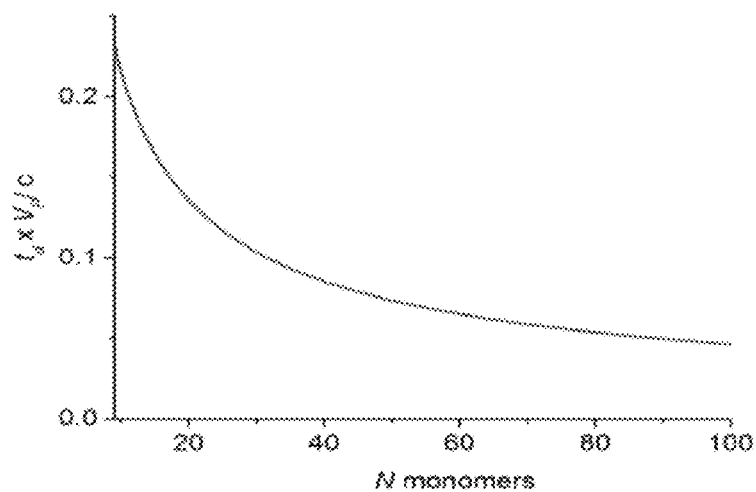

FIG. 38 describes a predicted trend in the most-probable translocation time for aggregates with constant charge per molecular weight while neglecting electrostatic effects and assuming a spherical aggregate.

Figure 39A:
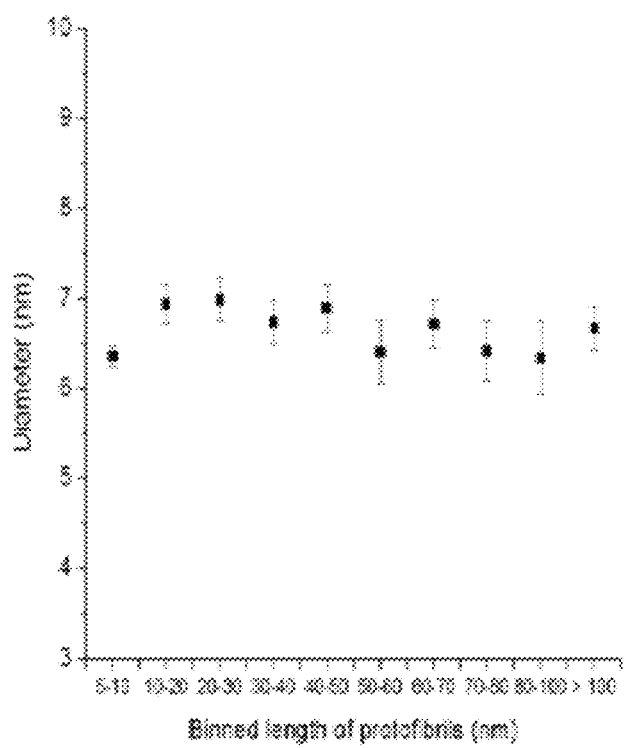
Figure 39B:
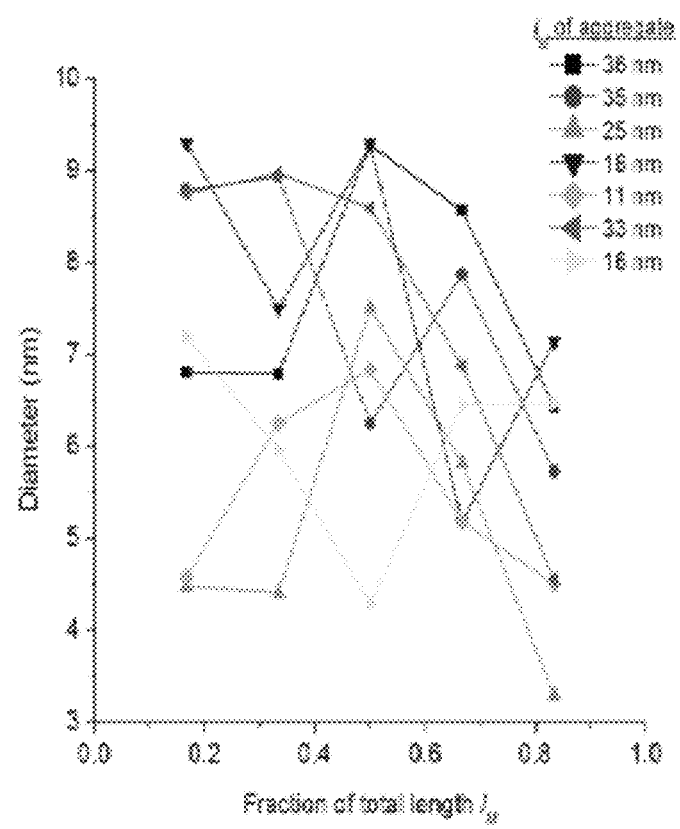

FIG. 39A and FIG. 39B show a diameter of protofibrils with various lengths (FIG. 39A) and diameter of individual protofibrils at various positions throughout the length of the aggregate as seen in TEM micrographs (FIG. 39B). FIG. 39A. Mean diameter of protofibrils with various total lengths, $l_M$, for protofibrils grouped into bins with lengths ranging from 5 nm to greater than 100 nm. Error bars are standard error of the mean. FIG. 39B. The diameter of seven aggregates measured at five different locations within the length of the aggregate. Note that the diameter remains relatively constant throughout the length of the individual aggregate suggesting that the shape of these protofibrils resembles that of a cylinder more than that of a prolate.

Figure 40A:
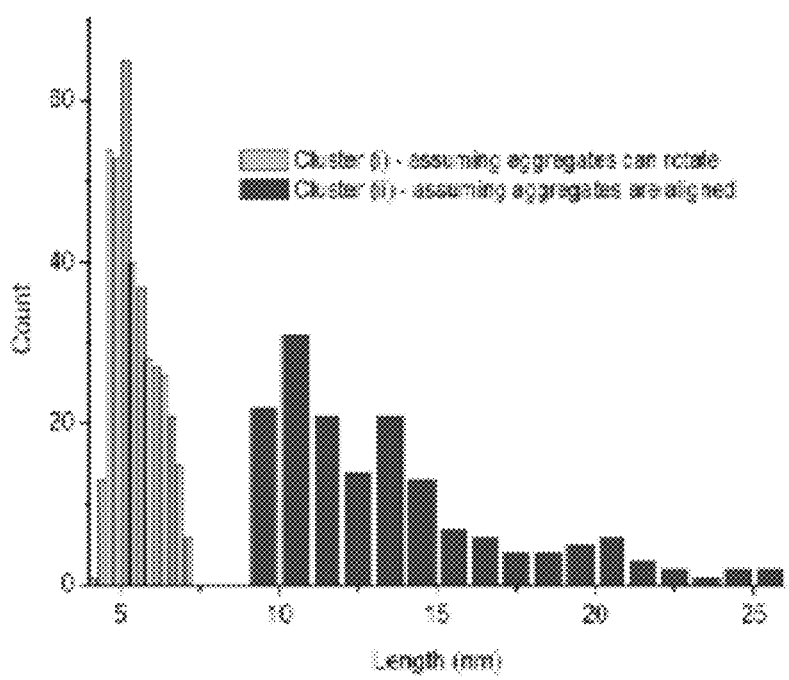
Figure 40B:
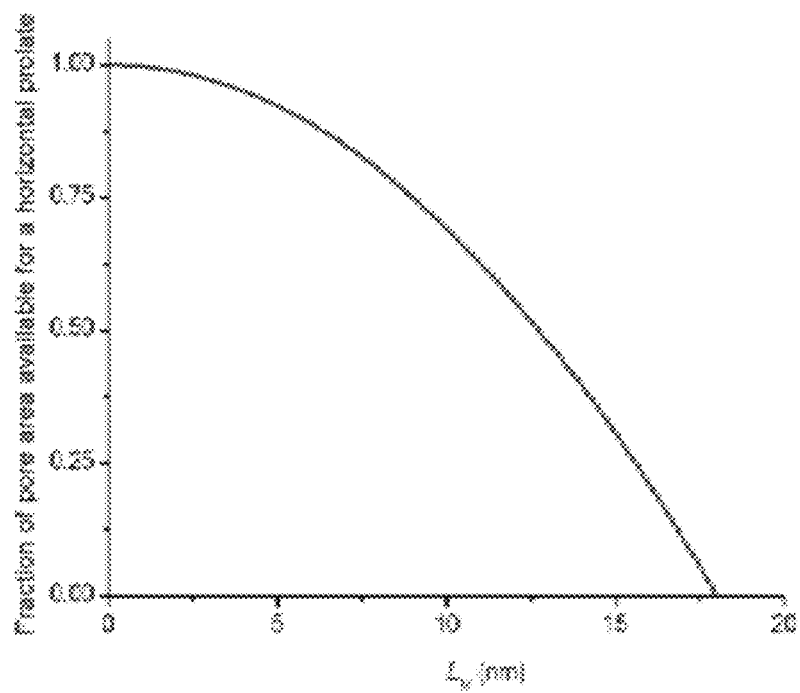

FIG. 40A and FIG. 40B show length of aggregates in cluster (i) assuming that aggregates are free to rotate in three dimensions inside the nanopore (FIG. 40A) and the fraction of the cross-sectional area of a nanopore that a horizontal cylinder of length $l_M$ could occupy (FIG. 40B). The lengths of aggregates in cluster (ii) are the same as those plotted in FIG. 3 of the main text and are shown for comparison.

Figure 41:
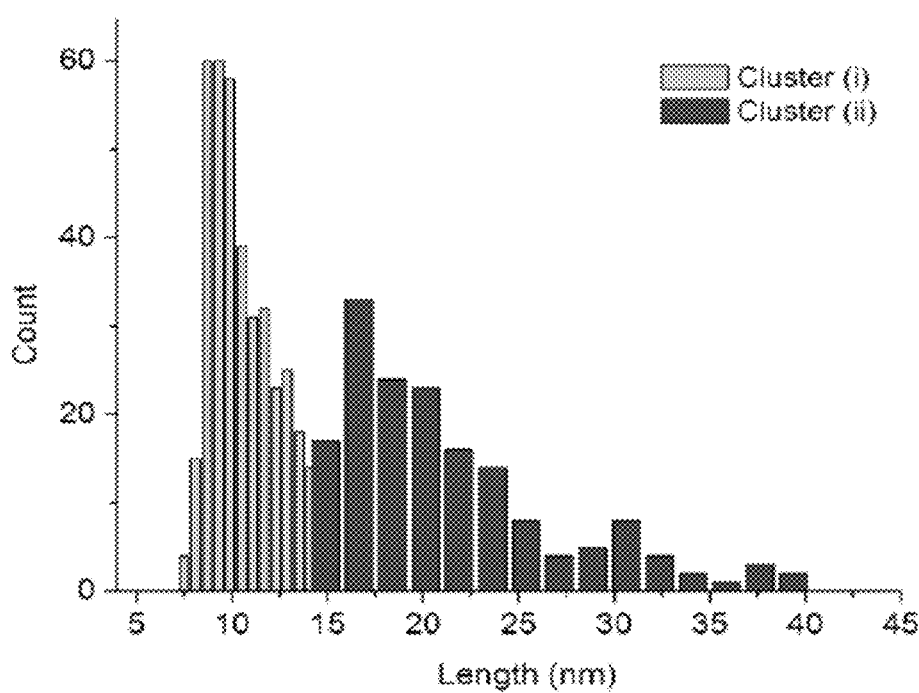

FIG. 41 shows the length of aggregates in clusters (i) and (ii) when defining their shape and volume as prolate spheroids.

Figure 42A:
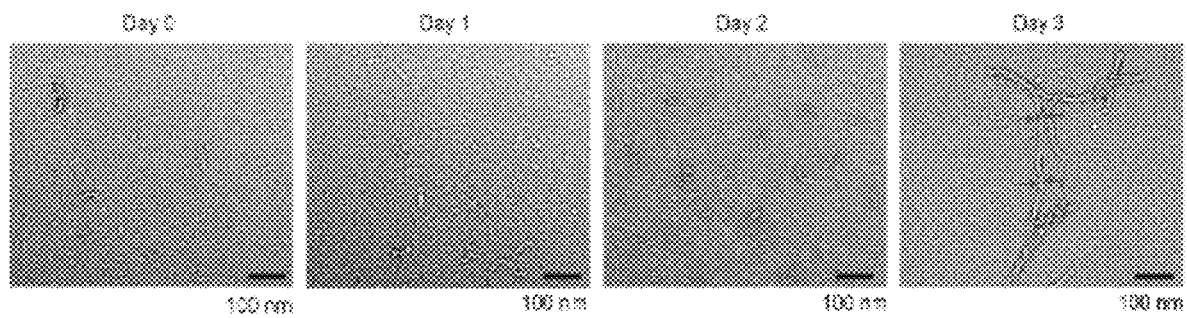
Figure 42B:
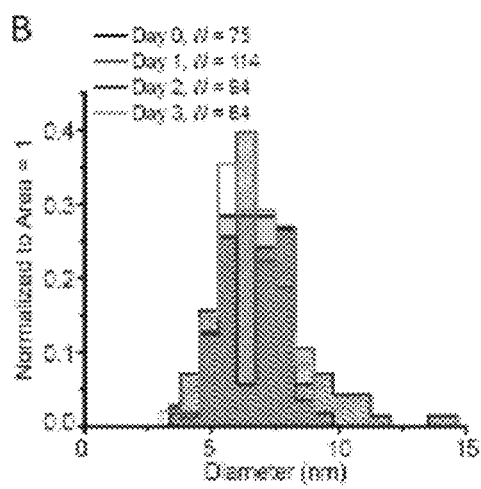
Figure 42C:
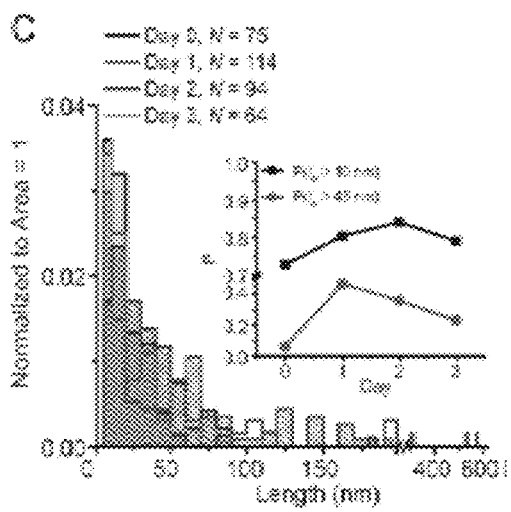
Figure 42D:
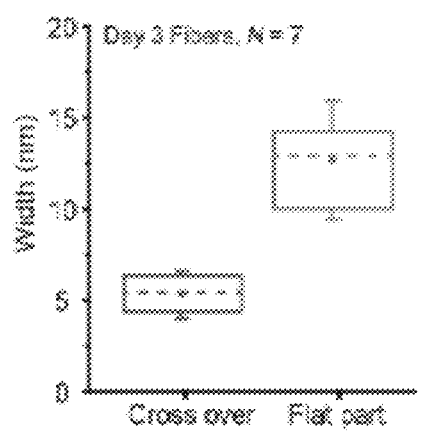

FIG. 42A, FIG. 42B, FIG. 42C, and FIG. 42D show an analysis of the size of $A\beta_{(1-40)}$ aggregates seen in micrographs taken with a transmission electron microscope. FIG. 42A. Micrographs showing aggregates with increasing size after incubation in pure water for 0, 1, 2 and 3 days. FIG. 42B & FIG. 42C. Histograms of the diameters (FIG. 42B) and lengths (FIG. 42C) of all aggregates that were not mature fibers. Inset in FIG. 42C. the proportion of aggregates with lengths longer than 10 nm and 45 nm, the effective length of the nanopore, as a function of aggregation time. FIG. 42D. Boxplots characterizing the mature fibers that formed after three days of aggregation. The fibers were characterized by their apparent widths when lying flat (blue arrows in FIG. 42A) on the TEM grid and when twisted or crossing over itself (red arrows in FIG. 42A) on the TEM grid.[23] The box represents the range between the 1$^{st}$ and 3$^{rd}$ quartiles, the dashed line represents the median, the dot is the mean, and the whiskers extend to the range of the data (minimum and maximum values).

DETAILED DESCRIPTION

In one embodiment, a nano-Coulter counter is provided and a method of using it. A method of detecting, quantifying, or characterizing a biomolecule or collection of biomolecules using the Coulter principle involves providing a transit path for biomolecules to pass through a nanopore from a first liquid compartment to a second liquid compartment. The first and second liquid compartments contain electrodes disposed to measure voltage, electrical current, or electrical resistance between the two liquid compartments. The method further includes measuring the voltage difference, electrical current, or electrical resistance between the two liquid compartments over time as individual biomolecules pass through the nanopore. In the method, the nanopore is a passageway or conduit through a substrate, with the passageway is lined with a fluid wall. In one embodiment, the fluid wall comprises a lipid bilayer and can contain a lipid anchored ligand that binds individual biomolecules.

The method is further characterized by the nanopore having a nominal width (perpendicular to the transit path) that is about 1.5 to about 50 times the dimension of the biomolecules. The nanopore is further characterized by a length (parallel to the transit path) of about 1 to 5 times its nominal width.

The apparatus and method operate on the Coulter principle. As biomolecules pass through or are drawn through the nanopore, it changes the electrical conductance (or other measureable electric parameter) which is detected by the electrodes and their control means. In effect, the biomolecules alter the effective cross-section of the conductive channel (the nanopore) through which they pass. If desired, a plurality of nanopores or nanochannels can be provided to separate the two liquid chambers containing an electrolyte solution. When particles or biomolecules flow from the first to the second liquid compartment, the electrical resistance of the liquid filled nanopore/nanochannel is changed. These changes in electrical resistance (or other electric parameter) are recorded as current or voltage pulses, which in turn are correlated to size, electrophoretic and diffusive mobility, surface charge, and concentration of the biomolecules, in non-limiting fashion.

In another aspect, a method of measuring the translocation time, ligand affinity, charge, volume, shape, size, or other characteristic of a biomolecule according to the Coulter principle is provided. The method involves detecting and measuring a change in conductivity, resistivity, resistance, conductance, current flow, voltage, or other electrical parameter measured between two liquid compartments separated by and fluidically coupled through a synthetic nanopore, upon translocation of a biomolecule such as a protein from one liquid compartment through the nanopore to the other liquid compartment. The nanopore comprises a passageway lined with a fluid wall. In one embodiment, the fluid wall comprises a lipid bilayer. The method further involves deriving the desired molecule characteristic from the measured electrical parameter. In preferred embodiments, the nanopore connecting the first and second compartments is about 10 to 100 nm in diameter (the dimension perpendicular to the flow path between the compartments) and is about 10 to 50 nm long (the dimension parallel to the flow path).

The changes in the electrical parameter that are measured in the method arise from the Coulter effect that provides that, in various embodiments, best results are obtained when the diameter or dimension of the molecule is approximately 2% to approximately 65% of the nominal diameter or dimension of the nanopore.

In another embodiment, a device is provided for measuring a parameter of a biomolecule using the Coulter principle. Such a "nano-Coulter counter" contains a first liquid compartment and a second liquid compartment defining a fluid flow direction from the first to the second compartment. A synthetic nanopore is disposed between and provides a fluid path between the first and second liquid compartments. There is a first electrode in the first liquid compartment and a second electrode in the second liquid compartment. In addition, means are provided for controlling the electrodes to measure resistance, voltage difference, current flow, or other electrical parameter between the first and second electrodes. Advantageously, the synthetic nanopore is a passageway between the first and second liquid compartments lined with a fluid wall, and wherein a dimension of the synthetic nanopore perpendicular to the fluid flow direction is about 10 to 500 nm, for example, about 10 to 100 nm, 10 to 50 nm, or 20 to 30 nm, in non-limiting embodiments.

Further non-limiting description of the various aspects and embodiments of the invention will now be provided. It is to be understood that limitations and features discussed with respect to one embodiment are also applicable and usable with other embodiments, unless the context requires otherwise. In particular, the characteristics of the nanopore separating the first and second liquid compartments are common to most of the aspects of the invention described herein. The nanopore is characterized by a width and length, and by the chemical composition of the lipid bilayer formed on the wall of the substrate that forms the nanopore.

Coulter Counting

In a device operating according the Coulter principle or Coulter effect, particles suspended—or biomolecules dissolved—in an electrolyte solution are drawn through a small aperture, separating two electrodes between which an electric current flows. The aperture is referred to in the current teachings as a nanopore. Nanochannel is sometimes used for the same concept. The voltage applied across the aperture creates a "sensing zone". As particles pass through the aperture (or "sensing zone"), they displace their own volume of electrolyte, momentarily changing the impedance of the aperture.

This change in impedance produces a pulse that is digitally processed in real time. The Coulter Principle states that the pulse is directly proportional to the tri-dimensional volume of the particle that produced it. Analyzing these pulses enables a size distribution to be acquired and displayed in volume ($nm^3$, $\mu m^3$ or fL) and diameter ($\mu m$ or nm). In addition, a metering device is used to draw a known volume of the particle suspension through the aperture (displayed in FIG. 7 as level sensors 16 and 18 attached between the first liquid compartment and the control means); a count of the number of pulses can then yield the concentration of particles in the sample.

Figure 7:
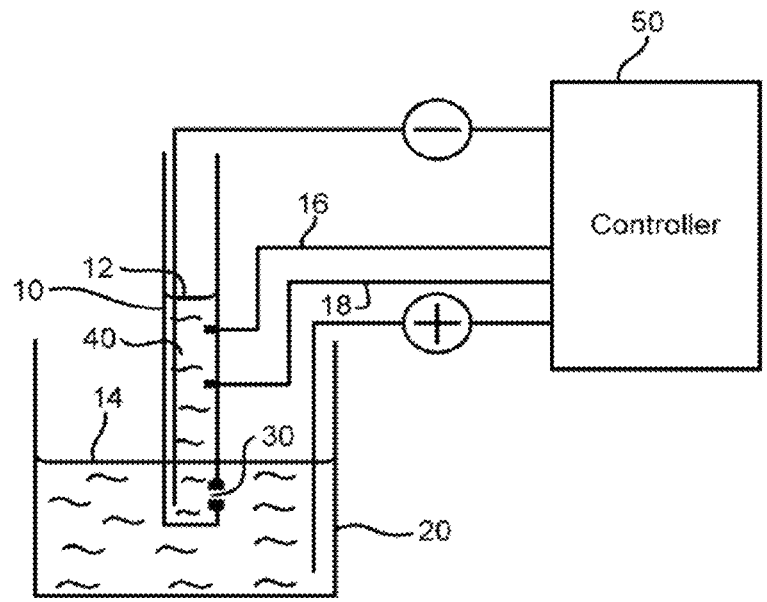

The basic non-electronic part of a traditional Coulter counter unit, as shown in FIG. 7, consists of a reservoir (the second liquid compartment 20) into which a finger-like tube (the first liquid compartment 10) is partially immersed. Near the lower end of the tube 10 is a very small hole 30 of known diameter. (Assortments of tubes are available covering a large range of hole sizes.) In the current teachings, the hole 30 is the nanopore discussed further herein.

If the "finger" 10 is filled to some point 12 above the level 14 of the outside reservoir 20, the contents 40 of the finger will slowly flow through the hole 30 until the two levels are equalized. This means that any particles suspended in or dissolved in the first liquid compartment 10 (such as the biomolecules described herein) will get flushed through the hole 30 also.

If electrodes (drawn as + and − in FIG. 7 are provided in the finger (first liquid compartment 10) and in the reservoir (second liquid compartment 20), an electrical current will then also pass through the hole (aperture or nanopore 30) along with the fluid. This current (or any similar parameter such as voltage or resistance) can be monitored for irregularities, for example by an oscilloscope type of device. Means 50 are provided for controlling the electrodes to monitor and display the changes in measured electrical parameters. In various embodiments, the measured parameters are provided as outputs for further manipulation by other modules or calculating means to provide other information derivable theoretically from the measured pulses.

Conventional Coulter counters are well known and commercially available. Method of controlling the electrodes to measure electrical parameters are provided in various of these commercial embodiments. The theoretical development of the derivation of molecular parameters from Coulter effect measurements is also well developed. Means for deriving the parameters are provided in commercial embodiments, and several algorithms and procedures for their calculation are also given in the Examples section below, and in references recited therein.

Fluid Coatings

Fluid coatings include those exhibiting a diffusion coefficient as measured with conventional fluorescence recovery after photobleaching (FRAP) that is sufficiently high to provide the benefits discussed herein, including the ability of the nano-Coulter counter with fluid walls to time resolve the translocation events. In various embodiments, the diffusion coefficient is at least $10^{-18}$ m$^2$ sec$^{-1}$, at least $10^{-16}$ m$^2$ sec$^{-1}$, at least $10^{-14}$ m$^2$ sec$^{-1}$, or at least $10^{-12}$ m$^2$ sec$^{-1}$. Although the invention is not limited by theory, it is believed that the viscosity characteristics of the fluid coatings contribute to the advantages observed when using them. In a preferred aspect, the fluid coating is provided on the nanopore aperture by applying a bilayer or monolayer to the surface of the substrate in the nanopore aperture. Basically, any molecule that is amphipathic is potentially capable of forming a suitable bilayer or monolayer on the substrates to provide nanopores with fluid walls. Examples include a surfactant or detergent having a hydrophilic group and a hydrophobic group. Other examples include without limitation molecules generated from click chemistry that resemble lipids, such as those described in "Vesicle and stable monolayer formation from simple "click" chemistry adducts in water" by Santanu Bhattacharya and Joydeep Biswas in Langmuir 2011 ASAP, the full disclosure of which is incorporated by reference herein. It is preferred in some embodiments to use surfactant, detergent, or lipid materials that have a charged hydrophilic head; in particular embodiments, phospholipids are preferred.

When the surface to which the coating is applied is hydrophilic, amphipathic molecules form or self-assemble on the substrate to make bilayers. When the surface is hydrophobic (or is modified to be hydrophobic, such as by silanization or other technique), amphipathic molecules tend to form a monolayer. In the monolayer, the hydrophobic tail of the amphipathic molecule is attracted to the hydrophobic surface so that the hydrophilic head of the molecule is exposed to the solution being tested. When the substrate has a hydrophilic surface, it attracts the hydrophilic head of the amphipathic molecule, and a bilayer forms such that the hydrophilic head of the second layer is exposed to the solution.

Lipid Coatings

When lipids are applied, they form fluid lipid walls on the nanopore. The lipids that make up the lipid bilayers or monolayers formed on the walls of the substrate to provide the nanopores are amphipathic, having a hydrophilic head and a hydrophobic tail.

Lipid bilayers and monolayers can be applied to the surface of the substrate to provide the nanopores with fluid walls, for example by exposing the substrate to solutions of liposomes made up of lipid components. Lipid bilayers and monolayers are well known.

Suitable phospholipids have a moiety that includes a charged phosphate group forming the hydrophilic head, and one or more fatty acid residues forming the hydrophobic tail. One group of phospholipids is derived chemically from fatty triglycerides by replacing one of the three fatty acid residues with a phosphate group. The phosphate group can be further esterified with functionalizing molecules.

Replacing one of the fatty acid residues on a triglyceride with a phosphate group results in the formation of a phosphatide. The diacylglycerol phosphate formed by a simple substitution of the phosphate for one of the acyl groups is called a phosphatidic acid. If the phosphatidic acid is esterified in turn, the phospholipid is a phosphatidyl lipid. Examples include phosphatidyl choline, phosphatidyl ethanolamine, phosphatidyl serine, phosphatidyl glycerol, and the like.

Phospholipids of the phosphatidic acid and phosphatidyl series are named as glycerol derivatives, naming the acyl or fatty acid group on the one and two hydroxyls of the parent glycerol, with the phosphate or the phosphatidyl group provided at position three of glycerol. Normally two of the three glycerol positions are esterified with fatty acids. In the lysophosphatidyl phospholipids (such as those exemplified in the Table), only the 1 position has a fatty acid moiety, with the phosphate containing group located on the 3-position.

Non-limiting examples of phospholipids in these classes are given in the following table, which illustrates the naming convention and the generic names of the various classes of phospholipid.

TABLE

Representative Phospholipids

| Abbreviation | CAS | Name | Type |
| --- | --- | --- | --- |
| DDPC | 3436-44-0 | 1,2-Didecanoyl-sn-glycero-3-phosphocholine | Phosphatidylcholine |
| DEPA-NA | 80724-31-8 | 1,2-Dierucoyl-sn-glycero-3-phosphate (Sodium Salt) | Phosphatidic acid |
| DEPC | 56649-39-9 | 1,2-Dierucoyl-sn-glycero-3-phosphocholine | Phosphatidylcholine |
| DEPE | 988-07-2 | 1,2-Dierucoyl-sn-glycero-3-phosphoethanolamine | Phosphatidylethanolamine |
| DEPG-NA | | 1,2-Dierucoyl-sn-glycero-3[Phospho-rac-(1-glycerol . . . ) (Sodium Salt) | Phosphatidylglycerol |
| DLOPC | 998-06-1 | 1,2-Dilinoleoyl-sn-glycero-3-phosphocholine | Phosphatidylcholine |
| DLPA-NA | | 1,2-Dilauroyl-sn-glycero-3-phosphate (Sodium Salt) | Phosphatidic acid |

TABLE-continued

Representative Phospholipids

| Abbreviation | CAS | Name | Type |
|---|---|---|---|
| DLPC | 18194-25-7 | 1,2-Dilauroyl-sn-glycero-3-phosphocholine | Phosphatidylcholine |
| DLPE | | 1,2-Dilauroyl-sn-glycero-3-phosphoethanolamine | Phosphatidylethanolamine |
| DLPG-NA | | 1,2-Dilauroyl-sn-glycero-3[Phospho-rac-(1-glycerol . . . ) (Sodium Salt) | Phosphatidylglycerol |
| DLPG-NH4 | | 1,2-Dilauroyl-sn-glycero-3[Phospho-rac-(1-glycerol . . . ) (Ammonium Salt) | Phosphatidylglycerol |
| DLPS-NA | | 1,2-Dilauroyl-sn-glycero-3-phosphoserine (Sodium Salt) | Phosphatidylserine |
| DMPA-NA | 80724-3 | 1,2-Dimyristoyl-sn-glycero-3-phosphate (Sodium Salt) | Phosphatidic acid |
| DMPC | 18194-24-6 | 1,2-Dimyristoyl-sn-glycero-3-phosphocholine | Phosphatidylcholine |
| DMPE | 988-07-2 | 1,2-Dimyristoyl-sn-glycero-3-phosphoethanolamine | Phosphatidylethanolamine |
| DMPG-NA | 67232-80-8 | 1,2-Dimyristoyl-sn-glycero-3[Phospho-rac-(1-glycerol . . . ) (Sodium Salt) | Phosphatidylglycerol |
| DMPG-NH4 | | 1,2-Dimyristoyl-sn-glycero-3[Phospho-rac-(1-glycerol . . . ) (Ammonium Salt) | Phosphatidylglycerol |
| DMPG-NH4/NA | | 1,2-Dimyristoyl-sn-glycero-3[Phospho-rac-(1-glycerol . . . ) (Sodium/Ammonium Salt) | Phosphatidylglycerol |
| DMPS-NA | | 1,2-Dimyristoyl-sn-glycero-3-phosphoserine (Sodium Salt) | Phosphatidylserine |
| DOPA-NA | | 1,2-Dioleoyl-sn-glycero-3-phosphate (Sodium Salt) | Phosphatidic acid |
| DOPC | 4235-95-4 | 1,2-Dioleoyl-sn-glycero-3-phosphocholine | Phosphatidylcholine |
| DOPE | 4004-5-1- | 1,2-Dioleoyl-sn-glycero-3-phosphoethanolamine | Phosphatidylethanolamine |
| DOPG-NA | 62700-69-0 | 1,2-Dioleoyl-sn-glycero-3[Phospho-rac-(1-glycerol . . . ) (Sodium Salt) | Phosphatidylglycerol |
| DOPS-NA | 70614-14-1 | 1,2-Dioleoyl-sn-glycero-3-phosphoserine (Sodium Salt) | Phosphatidylserine |
| DPPA-NA | 71065-87-7 | 1,2-Dipalmitoyl-sn-glycero-3-phosphate (Sodium Salt) | Phosphatidic acid |
| DPPC | 63-89-8 | 1,2-Dipalmitoyl-sn-glycero-3-phosphocholine | Phosphatidylcholine |
| DPPE | 923-61-5 | 1,2-Dipalmitoyl-sn-glycero-3-phosphoethanolamine | Phosphatidylethanolamine |
| DPPG-NA | 67232-81-9 | 1,2-Dipalmitoyl-sn-glycero-3[Phospho-rac-(1-glycerol . . . ) (Sodium Salt) | Phosphatidylglycerol |
| DPPG-NH4 | 73548-70-6 | 1,2-Dipalmitoyl-sn-glycero-3[Phospho-rac-(1-glycerol . . . ) (Ammonium Salt) | Phosphatidylglycerol |
| DPPS-NA | | 1,2-Dipalmitoyl-sn-glycero-3-phosphoserine (Sodium Salt) | Phosphatidylserine |
| DSPA-NA | 108321-18-2 | 1,2-Distearoyl-sn-glycero-3-phosphate (Sodium Salt) | Phosphatidic acid |
| DSPC | 816-94-4 | 1,2-Distearoyl-sn-glycero-3-phosphocholine | Phosphatidylcholine |
| DSPE | 1069-79-0 | 1,2-Distearoyl-sn-glycero-3-phosphoethanolamine | Phosphatidylethanolamine |
| DSPG-NA | 67232-82-0 | 1,2-Distearoyl-sn-glycero-3[Phospho-rac-(1-glycerol . . . ) (Sodium Salt) | Phosphatidylglycerol |
| DSPG-NH4 | 108347-80-4 | 1,2-Distearoyl-sn-glycero-3[Phospho-rac-(1-glycerol . . . ) (Ammonium Salt) | Phosphatidylglycerol |
| DSPS-NA | | 1,2-Distearoyl-sn-glycero-3-phosphoserine (Sodium Salt) | Phosphatidylserine |
| Egg Sphingomyelin empty Liposome | | | |
| EPC | | Egg-PC | Phosphatidylcholine |
| HEPC | | Hydrogenated Egg PC | Phosphatidylcholine |
| HSPC | | High purity Hydrogenated Soy PC | Phosphatidylcholine |
| HSPC | | Hydrogenated Soy PC | Phosphatidylcholine |
| LYSOPC MYRISTIC | 18194-24-6 | 1-Myristoyl-sn-glycero-3-phosphocholine | Lysophosphatidylcholine |
| LYSOPC PALMITIC | 17364-16-8 | 1-Palmitoyl-sn-glycero-3-phosphocholine | Lysophosphatidylcholine |
| LYSOPC STEARIC | 19420-57-6 | 1-Stearoyl-sn-glycero-3-phosphocholine | Lysophosphatidylcholine |
| Milk Sphingomyelin MPPC | | 1-Myristoyl-2-palmitoyl-sn-glycero 3-phosphocholine | Phosphatidylcholine |
| MSPC | | 1-Myristoyl-2-stearoyl-sn-glycero-3-phosphocholine | Phosphatidylcholine |

TABLE-continued

Representative Phospholipids

| Abbreviation | CAS | Name | Type |
|---|---|---|---|
| PMPC | | 1-Palmitoyl-2-myristoyl-sn-glycero-3-phosphocholine | Phosphatidylcholine |
| POPC | 26853-31-6 | 1-Palmitoyl-2-oleoyl-sn-glycero-3-phosphocholine | Phosphatidylcholine |
| POPE | | 1-Palmitoyl-2-oleoyl-sn-glycero-3-phosphoethanolamine | Phosphatidylethanolamine |
| POPG-NA | 81490-05-3 | 1-Palmitoyl-2-oleoyl-sn-glycero-3[Phospho-rac-(1-glycerol) . . . ] (Sodium Salt) | Phosphatidylglycerol |
| PSPC | | 1-Palmitoyl-2-stearoyl-sn-glycero-3-phosphocholine | Phosphatidylcholine |
| SMPC | | 1-Stearoyl-2-myristoyl-sn-glycero-3-phosphocholine | Phosphatidylcholine |
| SOPC | | 1-Stearoyl-2-oleoyl-sn-glycero-3-phosphocholine | Phosphatidylcholine |
| SPPC | | 1-Stearoyl-2-palmitoyl-sn-glycero-3-phosphocholine | Phosphatidylcholine |

Another class of phospholipids that form bilayers is the sphingolipids. Sphingomyelin is a class of sphingolipids that has a phosphocholine or phosphoethanolamine molecule with an ester linkage to the one hydroxy group of a ceramide. A ceramide in turn consists of a fatty acid chain attached through an amide linkage to sphingosine. An exemplary structure of a sphingolipid is

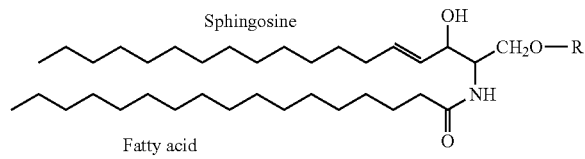

wherein R is the phosphorocholine or phosphoroethanolamine group. The sphingolipids can vary with the structure of the fatty acid, which is shown in the Figure as a $C_{17}$ saturated fatty acid.

Lipid Anchored Ligands

The preferred phospholipids and sphingolipids self-assemble onto the substrate as a bilayer or monolayer when a substrate is exposed to a solution or suspension of liposomes made from the respective phospholipids. The liposomes in turn self-assemble in solution when the component lipids are dissolved in an aqueous system. If desired, a lipid molecule containing a ligand (also called a "liganded phospholipid") is also provided in the solution from which the liposomes are produced. When assembled onto the substrate surface in a bilayer, this provides a lipid anchored ligand in the fluid wall. In certain embodiments, the ligand of the liganded phospholipid serves to bind or otherwise interact with biomolecules or other analytes of interest.

The phospholipid derivatized with the ligand is provided in a suitable mole fraction relative to the other phospholipids. Normally, the mole fraction of the liganded phospholipid is 0.5 or less, and above 0.000001. Depending on the specificity and binding constant of the ligand for the biomolecule, the mole fraction of ligand in the bilayer can be at least 0.000001, at least 0.00001, at least 0.0001, at least 0.001, or at least 0.01 (the numbers are mole fractions ranging from zero to one. A mole percent ligand can be derived by multiplying the mole fraction by 100). In various embodiments, the mole fraction of liganded phospholipid is no more than 0.5, no more than 0.2, no more than 0.1, no more than 0.01, and no more than 0.001. Typical ranges of mole fraction for the liganded phospholipid in the fluid lipid walls are 0.000001-0.2, 0.00001-0.2, 0.001-0.1, 0.01-0.1, 0.000001-0.1, 0.00001-0.1, 0.000001-0.01, 0.000001-0.001, and so on. In a preferred embodiment, the ligand is covalently attached to a structure like that of the other phospholipids in the bilayer. For example, a liganding functional group such as biotin can be covalently attached to the nitrogen of a phosphatidylethanolamine molecule. Many other examples are known or can be synthesized.

The ligand to be incorporated into the bilayer to provide the lipid anchored ligand of the invention is selected from compounds that have a wide range of functional groups. Basically, any functional group to which the biomolecule of interest will bind or link to covalently can be used. For any ligand/biomolecule combination, suitable conditions can be empirically determined. Generally, the stronger the affinity of the ligand and biomolecule (expressed in the conventional way as binding constants or inhibition constants), the lower the mole fraction need be provided of the ligand in the fluid wall. The converse is also true in that the weaker the affinity of the ligand and biomolecule interaction, the higher the mole fraction need be provided of the ligand in the fluid wall. A quick calculation suggests that ~20 mM will be the weakest equilibrium dissociation constant (Kd) that the system will work with for detecting specifically lipid-attached proteins. Stronger affinities (Kd<20 mM) will allow the system to use less ligand in the fluid walls.

The nature of the ligand and its concentration in the bilayer can be varied to provide a suitable amount of binding in the fluid wall lining the nanopore. Although the invention is not limited by theory, this affinity of the biomolecule for the ligand in the fluid wall or the covalent bond of a biomolecule to a lipid in the fluid wall accounts for at least some of the advantages provided by the method. In particular, it is believed that binding to these ligands or covalent bond to a lipid in fluid wall effectively anchors the protein to a lipid in the fluid wall and slows down the translocation of the biomolecule through the nanopore, thereby allowing the electronics to time resolve the translocation events.

Examples of Ligands

Examples of ligands that can be covalently incorporated into the phospholipid bilayers as discussed above include biotin, cholesterol, sulfonamide, nickel (coupled with nickel chelating lipids) and antibodies. Other examples of ligands include proteins. In various embodiments proteins used as ligands contain functional groups or can be modified to contain functional groups that can react for covalent attachment. Examples of such groups on proteins include thiol groups, maleimide groups, N-hydroxysuccimide (NHS) ester groups, or so called "Click" chemistry, which proceeds through nitrile, acetylene, or azide groups, or cycloadditions such as the Diels Alder reaction.

Manufacture of Nanopores

The nanoholes can be fabricated in materials such as silicon nitride, silicon dioxide, borosilicate glass, aluminum oxide, or polyethylene terephthalate. Depending on the material and the size of the desired hole, different fabrication techniques are used. Common techniques include the so called "track etching technique" (Harrell, C. C. et al., (2003), Synthetic single-nanopore and nanotube membranes, Anal. Chem. 75:6861-6867), the "ion beam sculpting" technique (Jiali Li et al., (2001), Ion Beam Sculpting at nanometer length scales, *Nature* 412, 166-169), the "electron beam sculpting" technique (Storm, A. J. et al., (2003), Fabrication of solid-state nanopores with single-nanometer precision, *Nat. Mater.* 2:537-540), and "the laser machining in glass" technique (Joglekar et al. (2004), Optics at critical intensity: applications to nanomorphing, *PNAS,* 101: 5856-5861).

When the lipid bilayer is formed in the passageway of the substrate, the effective dimension or diameter of the passageway is reduced by the thickness of the bilayers formed. One speaks then of a nanopore having a nominal dimension that takes into account the lowering of the effective diameter of the passageway as a consequence of the bilayer being formed. Normally the nominal diameter or dimension of the nanopore is the dimension of the passage or hole through the substrate reduced by two times the bilayer thickness plus a layer of water between the lipid bilayer and the substrate surface or one time a monolayers thickness. If the passageway is perfectly round, diameter and dimension are used interchangeably. For shapes other than round, other dimensions can be used, such as chords, long axes, short axes, and the like. Frequently, the dimension of interest is the nominal dimension of the nanopore that permits a non-spherical biomolecule to pass through, in some orientation where the dimension of the biomolecule and the pore are in relation to one another.

The nominal dimension of the nanopore, being a function of the bilayer thickness, is therefore also a function of the length of the "tail" (the acyl chains) on the phospholipids in the bilayer, since the thickness of the bilayer depends on the tail length. The length of the tail in turn depends on the number of carbon atoms and the number of double bonds. These features are illustrated further in the Examples section below. In certain embodiments, the nominal dimension of the nanopores can be fine-tuned by the choice of phospholipid.

Biomolecules

Using the methods and devices described herein, a variety of biomolecules can be detected and studied. Generally speaking, any molecule or particle having nanometer dimensions can be studied. These include biomolecules such as proteins, nucleic acids, antibodies, polysaccharides, virus capsids, biopolymers such as fibrils and so on as well synthetic particles such as polystyrene particles, gold nanoparticles, or dendritic particles. Additional subjects of study include protein aggregates such as those formed by amyloid beta (Aβ) peptides. Other aggregates include immune complexes and G-protein coupled receptors. By using the nanopores with fluid walls, translocation times of such molecules or particles through nanopores is slowed down sufficiently that the transit or translocation events can be isolated and measured.

Further non-limiting description is provided in the following Examples section. The Examples present enabling disclosure for carrying out the invention.

EXAMPLES

Nanopores hold tremendous promise for applications such as single-molecule binding assays[1-3], portable detection of (bio)warfare agents[4-6], and ultra-fast sequencing of DNA or RNA[7,8]. Nanopore-based experiments provide sub-molecular detail on the composition of individual molecules[9] and on the formation of molecular complexes or aggregates[1,10]. Recording of resistive current pulses during the translocation of single molecules through electrolyte-filled nanopores makes it possible to study their size[1,4,6,11-13], conformation[14,15], and activity[16,17] in situ[3,18-23]. This technique can characterize hundreds of unlabeled single molecules per second in physiological solutions and yields distributions of measured parameters from these single-molecule investigations[3,9]. However, several challenges should be addressed. First, there is a need for methods that can reliably fabricate synthetic nanopores on the sub-nanometer scale[24] and adjust or actuate pore diameters in situ[24,25]. Second, better control of translocation times of single-molecule analytes are still needed to achieve complete time resolution of translocation signals and more accurate determination of the amplitude and duration of resistive pulses[26-28]. Third, methods to control the surface chemistry inside synthetic pores[16] may reduce non-specific interactions of analytes with the pore walls[1,3,29] and prevent pore clogging[3]. Finally, low frequency of translocation events at low analyte concentrations[30] and the poor specificity of the nanopores for analytes[3] need to be improved.

Nature solved most of these challenges in the design of biological nanopores[23]. Ion channel proteins, for instance, fold into three-dimensional structures with predetermined locations of individual atoms and precisely defined internal diameters that can be actuated by ligand binding or by changes in the environment of the pore[31]. Many ion channel proteins are specific towards ligands and permeants, have minimal non-specific interactions, and irreversible clogging is rare. However, instability of these proteins limits their sensing applications[23].

Figure 1A:
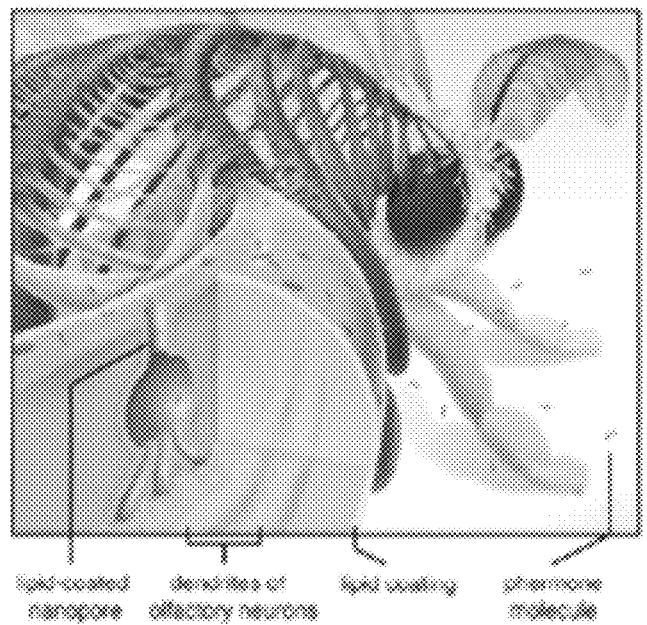

Insects detect pheromones by translocating odorant molecules through lipid-coated nanopores (diameter 6-65 nm) that span their exoskeleton (FIG. 1a)[32-34]. These lipid coatings are thought to participate in capture, pre-concentration, and subsequent translocation of odorants to specific receptors on dendrites of olfactory neurons in the antennae of insects[32,34]. Inspired by this design, we explored whether coating synthetic nanopores of comparable diameters with fluid lipid bilayers could provide benefits for nanopore-based, resistive pulse sensing of single proteins while addressing the associated challenges. Coating synthetic nanopores with organic molecules has been shown but these coatings were fixed on the surface of the pore[35-37]. Here we introduce the concept of fluid coatings Methods Lipids and Proteins We obtained all phospholipids from Avanti Polar Lipids, Inc. We purchased the proteins streptavidin (SA) and monoclonal anti-biotin antibody (mAb, B7653) from Sigma Alrdrich and polyclonal anti-biotin Fab fragments (Fab, 20938) from Rockland Inc.

Nanopores

We used a focused ion beam to fabricate nanopores in a silicon nitride membrane that was supported by a silicon chip (see Supplementary Section S1 for information on the pores)[59]. Prior to experiments, we cleaned the pore-containing chips for at least 30 min with a fresh mixture of 3:1 (v/v) concentrated sulfuric acid and 30% (v/v) aqueous hydrogen peroxide solution at a temperature of 60-70° C. followed by rinsing with deionized water and drying with argon gas. To create separate fluid compartments on either side of the nanopore, we mounted the chip between two pieces of cured polydimethylsiloxane (PDMS)[10]. After each experiment, we rinsed the silicon chips for 2-3 min successively with the following solvents: water, ethanol, methanol, and chloroform. We stored chips in chloroform between experiments.

Formation of Supported Lipid Bilayers

We formed supported lipid bilayers by fusion of small unilamellar vesicles (SUVs)[40-43]. We prepared these SUVs as described in Supplementary Section S2. To form the supported lipid bilayer on silicon nitride membranes, we filled the top compartment of the PDMS fluidic setup with 10-30 μL of the aqueous solution with the SUVs and the bottom compartment with a 150 mM KCl solution without liposomes. After 5-10 min, we removed excess SUVs by immersing the entire fluidic setup for 5-10 min in a large (500 mL) beaker containing deionized water. Before recordings, the fluidic compartments were filled with the desired electrolyte. Each liposome preparation contained 0.8 mol % of the fluorescently-labeled lipid, 1,2-dipalmitoyl-sn-glycero-3-phosphoethanolamine-N-(lissamine rhodamine B sulfonyl) (Rh-PE), for measuring the fluidity of lipid bilayers by fluorescence recovery after photobleaching (FRAP, see Supplementary Section S2).

Electrical Resistance as a Function of Bilayer Thickness

We used Ag/AgCl pellet electrodes (Warner Instruments) to monitor ionic currents through electrolyte-filled nanopores with a patch-clamp amplifier (Axopatch 200B, Molecular Devices Inc.) in voltage clamp mode (i.e., at constant applied voltage). See Supplementary Section S9 for a description of data acquisition methods. We determined the resistance between the electrodes by measuring the current at various applied voltages in the range of ±0.5 V; the slope of the corresponding current versus voltage plots equaled the inverse of the resistance. To measure the resistance as a function of the bilayer thickness, we formed different lipid bilayers on the same chip by using SUVs composed of DLPC, DMPC, DΔPPC, or DEPC lipids. We cleaned this chip before the formation of each lipid bilayer as described above. The chip used for these experiments contained a nanopore with a diameter of 28 nm and a length of 12 nm (see Supplementary Section S1 for a TEM image) and the recording buffer contained 500 mM KCl and 10 mM HEPES at a pH value of 7.4±0.1. To measure the resistance of nanopores as a function of temperature, we used a feedback-controlled Peltier Cooler from Warner Instruments (see Supplementary Section S1).

Sensing Proteins with Biotinylated Lipids in the Bilayer

We formed supported lipid bilayers on the silicon chip from SUVs containing 0.15-0.4 mol % of biotin-PE, 0.8 mol % Rh-PE, and ~99 mol % POPC. We used an electrolyte containing 2.0 M KCl and 10 mM HEPES with a pH of 7.4±0.1 and performed all current recordings at −0.1 V. To detect SA, we used a nanopore with an area-equivalent diameter of 19.2 nm (see Supplementary Section S1) and a length of 18 nm (before formation of the bilayer), and we added SA to the top compartment at concentrations of 3.2-6.2 pM. To detect mAb and Fab, we used a nanopore with an area equivalent diameter of 33.0 nm and a length of 22 nm; we added mAb or Fab to the top compartment at concentrations of mAb or Fab of 0.1-50 nM. (See Supplementary Section S9 for a description of the resistive-pulse analysis.)

Detection of Aggregates of Amyloid-Beta (Aβ) Peptides

See Supplementary Section S10 for a description of Aβ sample preparation. We used a nanopore with a diameter of 96 nm and a length of ~275 nm (before bilayer coating), which was either uncoated or coated with a POPC bilayer. We added solutions containing Aβ peptides (residues 1-40) to the top compartment at concentrations of Aβ of 0.1 to 0.2 mg×mL$^{-1}$. We used an electrolyte containing 70 mM KCl and 10 mM HEPES with a pH of 7.4±0.1 and recorded resistive pulses at +0.2 V.

Example 1

Bilayer Coatings Enable Fine Tuning and Actuating Pore Diameters

Figure 1B:
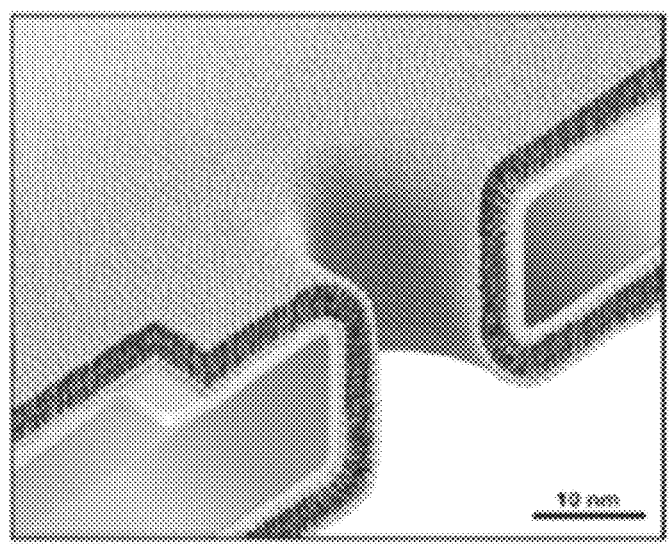

To create lipid bilayer-coated nanopores (FIG. 1b), we exposed silicon chips that contained a single pore through a silicon nitride window to an aqueous suspension of small unilamellar liposomes[40-43]. Spreading of these liposomes on the $Si_3N_4$ window and on the walls of the nanopore (see Supplementary Sections S1-S3) created a bilayer coating and reduced the nanopore diameter. The thickness and surface chemistry of this coating can be accurately controlled by the choice of lipids in the liposome preparation. For instance, the bilayer thickness is fine-tuned by the length and the number of double bonds in the hydrocarbon tails of the lipids (FIG. 1c), whereas the surface chemistry is controlled by the nature of their polar head groups (see Supplementary Section S4).

Figure 1C:
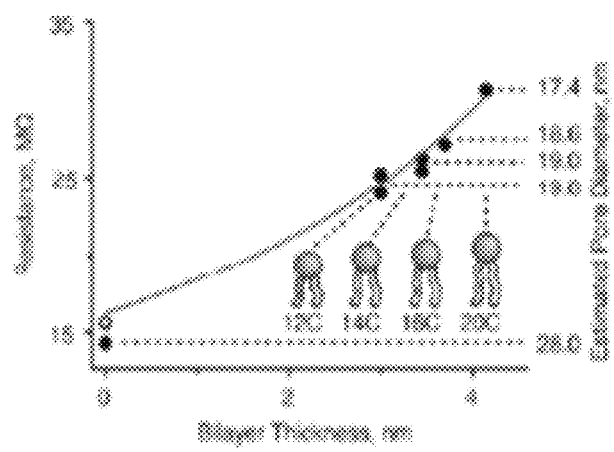

The capability of fine-tuning the diameter of nanopores is illustrated by the red curve in FIG. 1c. This curve resulted from a best fit of the data to a simple physical model that described the electrical resistance through the nanopore, R (a), as the sum of four terms: 1) the resistance of the cylindrical nanopore, 2) the access resistance to and from the nanopore[31], 3) the resistance of the cylindrical channel through the silicon nitride window that led to the pore (see Supplementary Section S1 for a schematic drawing), and 4) the access resistance to this cylindrical channel. These four resistances in series are represented in sequence by the terms in equation (1) (see Supplementary Section S1 for a derivation):

$$R = \frac{\rho(l_P + 2d + 2w_L)}{\pi(r_P - d - w_L)^2} + \frac{\rho}{2(r_P - d - w_L)} + \frac{\rho(l_C + 2d + 2w_L)}{\pi(r_C - d - w_L)^2} + \frac{\rho}{4(r_C - d - w_L)}, \quad (1)$$

where ρ (Ω m) represents the resistivity of the electrolyte, $l_P$ (m) the length of the cylindrical nanopore, d (m) the thickness of the lipid bilayer (see Table 1), $w_L$ (m) the thickness of the interstitial water layer between the bilayer and the silicon nitride wall of the pore[44,45], $r_P$ (m) the radius of the nanopore, $l_C$ (m) the length of the cylindrical channel through the silicon nitride that led to the pore, and $r_C$ (m) the radius of this cylindrical channel (see Supplementary Section S1 for values of ρ, $l_P$, $r_P$, $l_C$, and $r_C$).

TABLE 1

Lipids used in this work to coat nanopore walls.

| Chemical Name | Abbreviation | Acyl Chains[a] | Bilayer Thickness[b] (nm) |
|---|---|---|---|
| 1,2-dilauroyl-sn-glycero-3-phosphocholine | DLPC | (12:0) | 3.0 ± 0.1 |
| 1,2-dimyristoyl-sn-glycero-3-phosphocholine | DMPC | (14:0) | 3.4 ± 0.1 |
| 1,2-dipalmitoleoyl-sn-glycero-3-phosphocholine | D☐PPC | (16:1) | 3.6 ± 0.1 |
| 1,2-dieicosenoyl-sn-glycero-3-phosphocholine | DEPC | (20:1) | 4.2 ± 0.1 |
| 1-palmitoyl-2-oleoyl-sn-glycero-3-phosphocholine | POPC | (18:1-16:0) | 3.7 ± 0.1 |
| 1,2-dipalmitoyl-sn-glycero-3-phosphoethanolamine-N-(cap biotinyl) | biotin-PE | (16:0) | — |

[a]For lipids with two identical acyl chains, (c:db) indicates the number of carbons (c) and the number of double bonds (db); for lipids with two different acyl chains, (c1:d1-c2:db2) refer to acyl chains 1 and 2.
[b]Thickness according to Lewis et al[38].

Equation (1) shows that this model estimated the effective, open radius of a pore by taking into account the reduction of its radius and increase of its length as a function of the thickness of the bilayer coating and the thickness of the interstitial water layer between the bilayer and the silicon nitride wall of the pore. A fit of the data in FIG. 1c to this model returned a thickness of the water layer of $w_L=1.2\pm0.1$ nm (literature values: 0.5-1.7 nm)[44,45] as the only fitting parameter. The excellent fit of the data to equation (1) ($R^2=0.97$, $N=7$) and the realistic value for the thickness of the water layer, suggest that self-assembled bilayer coatings make it possible to fine-tune and predict the radius of a cylindrical nanopore in increments of two carbon atoms (albeit in a range limited to lipids that can generate stable supported lipid bilayers).

Figure 1D:
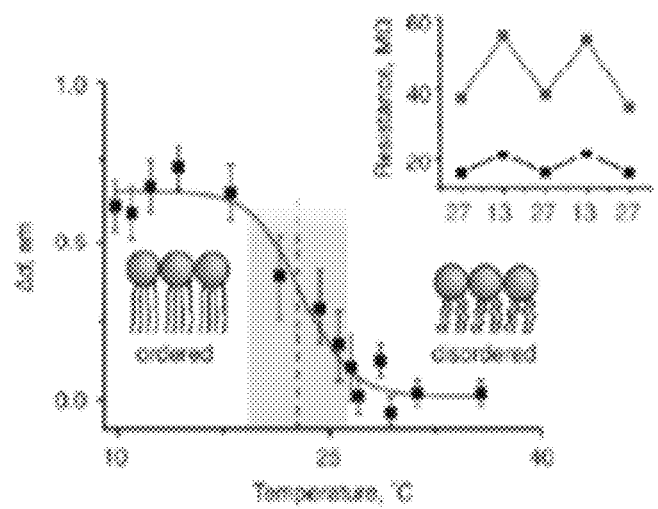

Since the sensitivity and information content of nanopore-based single-molecule experiments depend strongly on the size of the pore, one particularly desirable feature for nanopore sensing would be the ability to adjust the diameter of a nanopore dynamically to the size of various analytes, in situ. FIG. 1d demonstrates that a thermal phase transition of a coating of DMPC lipids (Table 1) from the ordered gel phase ($L_\beta$) to the disordered liquid crystalline phase ($L_\beta$) decreased the estimated thickness of the bilayer coating by $\Delta d \approx 0.7$ nm (lit.: 0.9-1.1 nm)[39,46,47] and made it possible to actuate the diameter of the nanopores dynamically by 1.4±0.1 nm. FIG. 1d also shows that the midpoint (dashed blue line) and range (grey area) of the phase transition in the nanopore coating occurred precisely at the reported temperature for DMPC lipids of 23.5±2.3° C.[39]. Changing the diameter of nanopores by a phase transition of lipids may be a relevant mechanism by which insects regulate their water uptake and evaporative loss through lipid-coated nanopores in their exoskeleton[34,48]. In the context of synthetic nanopores, this bio-inspired capability of changing pore diameters constitutes a novel approach to determine thermal phase transition temperatures of lipid bilayers, in situ.

Example 2

Figure 2A:
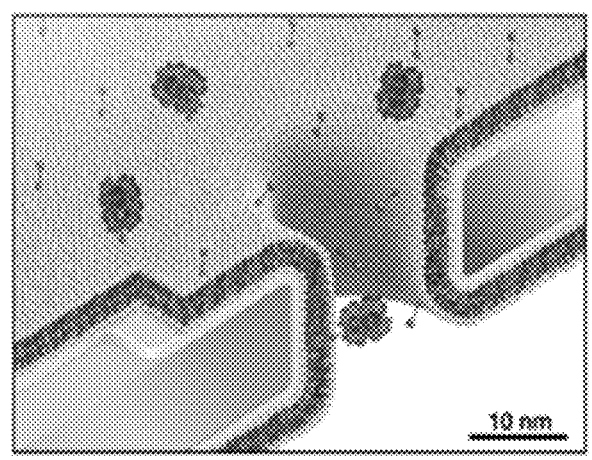

Lipid Anchored Ligands Concentrate Specific Analytes and Enable their Translocation In addition to fine-tuning and actuating the diameters of nanopores, bilayer coatings provide a straightforward strategy to render nanopore recordings specific for certain analytes by functionalizing the bilayer surface with ligands or receptors. FIG. 2 illustrates that adding defined mole fractions of lipids with desired functional groups (here, biotinylated lipids) during the formulation of liposomes and the subsequent formation of a bilayer coating[42] can control the surface density of ligands in and around the pore. These lipid-anchored ligands, which were mobile within the fluid sheet of the lipid bilayer, could concentrate dilute analytes from the bulk solution to specific ligands on the bilayer surface and deliver these analytes to the pore by two-dimensional diffusion (FIG. 2a,b). Compare the lipid coating of olfactory sensilla in insect antenna, which contributes to the extremely sensitive detection of lipophilic pheromones by insects[32,34,49].

Figure 2B:
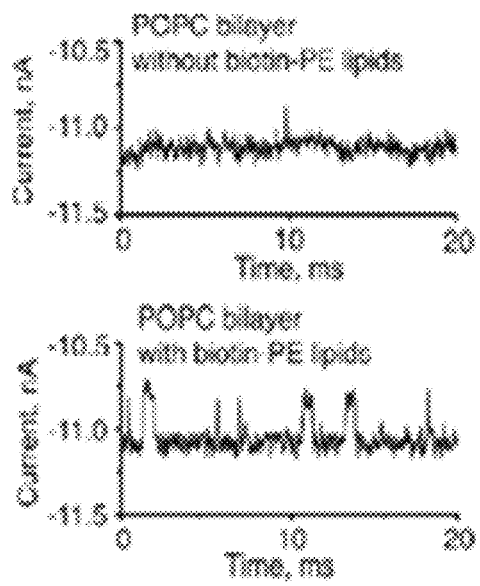
Figure 2C:
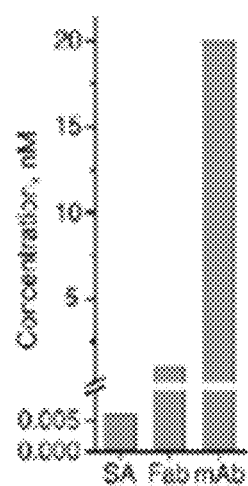

Pre-concentrating and translocating analytes that are bound to a fluid surface also made it possible to distinguish between different analytes based on their affinity to the displayed ligand (FIG. 2c). For instance, proteins present at picomolar concentrations in the bulk electrolyte solution concentrated at the surface and induced frequent translocation events if they bound with high affinity to lipid-anchored ligands in the bilayer. In contrast, proteins with low affinity to these ligands required more than 300-fold increased bulk concentrations to reach comparable frequencies of time-resolved translocation events (FIG. 2c). In the case of streptavidin, polyclonal anti-biotin Fab fragments and monoclonal anti-biotin IgG antibodies, we found that to reach a frequency of 30-100 translocation events per second, a concentration of only 0.006 nM streptavidin was required compared to 1 nM of Fab fragment and 20 nM monoclonal antibody. Control experiments revealed that in the absence of biotinylated lipids in the bilayer coating, or in the presence of excess biotin in solution, the frequency of detectable translocation events for each protein was up to 500-fold lower than in the presence of specific capture sites in the bilayer (FIG. 2b and Supplementary Section S5).

Example 3

Bilayer Viscosity Controls and Prolongs Translocation of Lipid-Anchored Analytes The capability of moving captured analytes through pores with fluid walls made it possible to obtain the translocation time, $t_d$, through the pore as well as the corresponding amplitude of the resistive pulses, $\Delta I$. This information is unique to the fluid nanopore coatings introduced here; previous reports on nanopore recordings with specific, surface-attached binding groups captured analytes on permanently fixed positions4,5 and did not allow translocation of bound analytes thereby excluding the possibility to determine $t_d$ or to relate $\Delta I$ to the molecular volume of the bound analyte. An additional benefit of translocating analytes that are bound to a lipid anchor emerges if the intrinsic translocation speed of the unbound analyte through a pore is too fast to resolve $t_d$ and $\Delta I$ completely in time—a problem encountered previously by other groups26-28.

FIG. 2b and Supplementary Section S5 show that translocation events of individual proteins could not be fully resolved without lipid-anchored capture sites. In contrast, anchoring analytes to lipids during their passage through the pore had the advantage that the translocation speed was dominated by the high viscosity of the bilayer coating rather than the low viscosity of the aqueous electrolyte in the pore50. The resulting, prolonged translocation times enabled time-resolved detection of $t_d$ (FIG. 3) and $\Delta I$ (FIG. 4) combined with accurate, quantitative characterization of individual proteins. Alternative strategies for prolonging the translocation time by increasing the length of the pore or the viscosity of the electrolyte or by reducing the applied voltage have been associated with a reduction of the amplitude of translocation events and reduced the signal to noise ratio28. In contrast, bilayer coatings with fluid capture sites can fine-tune the viscosity of the bilayer and prolong the translocation times of lipid-anchored analytes while the conductivity of the aqueous electrolyte remains unchanged.

Figure 3A:
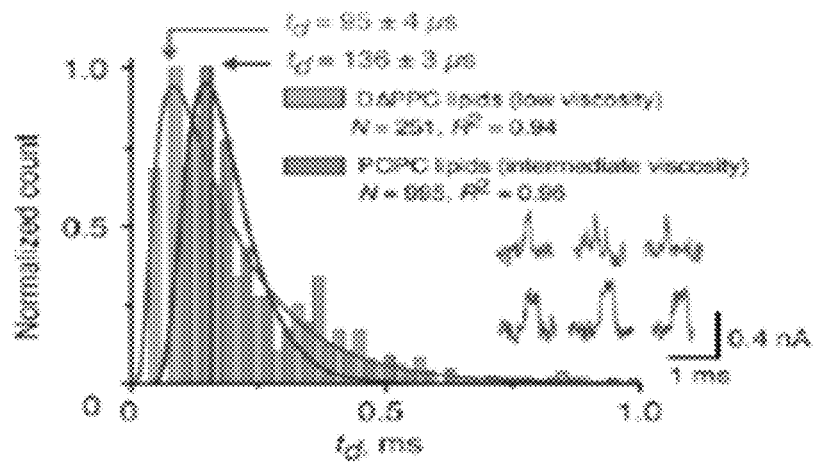
Figure 3B:
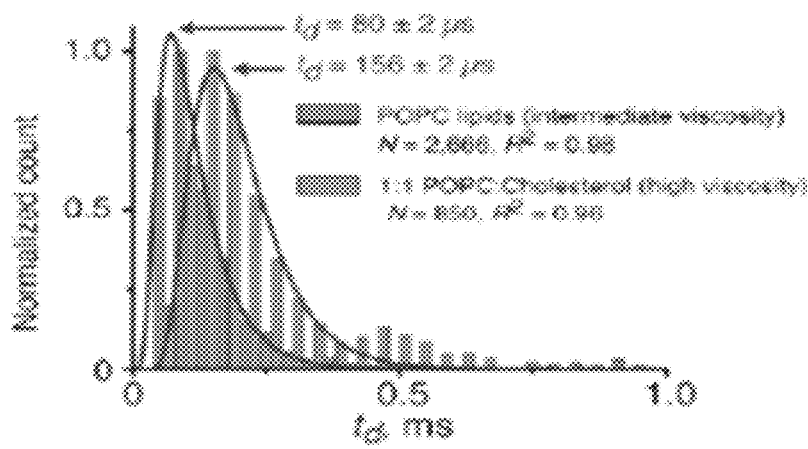

FIG. 3a demonstrates that acyl chains with increasing length and saturation could slow down translocation speeds. For instance, POPC lipids with one monounsaturated acyl chain of 18 carbon atoms and a second saturated acyl chain of 16 carbons generated approximately 1.4 times more viscous bilayers than DΔPPC lipids with two monounsaturated acyl chains of 16 carbons. These two bilayer coatings resulted in most frequently observed translocation times for streptavidin of 114±15 □s in the POPC coating compared to 81±10 μs in the DΔPPC coating (FIG. 3a). Translocation speeds could be slowed down even further by adding 50 mol % cholesterol to a POPC bilayer; in this case the most frequently observed translocation time of Fab fragments doubled from 78±5 μs to 175±4 μs (FIG. 3b).

Example 4

Resolving Translocation Events Enables Determining the Volume of Individual Proteins Complete time resolution of translocation events of lipid-anchored proteins allowed us to determine the volume of individual translocating proteins based on accurate acquisition of the amplitude of resistive pulses, ΔI(t). FIG. 4 shows amplitude distributions of the resistive pulses for three different biotin-binding proteins. We used equation (2) to estimate the transiently excluded volume of electrolyte, Λ(t) (m³) during the translocation of these three proteins12,13, 51.

$$\Delta I(t) = \frac{\gamma V_a \Lambda(t)}{\rho(l_P + 1.6 r_P)^2} S\left(\frac{r_P}{d_M}\right) \quad (2)$$

Figure 4A:
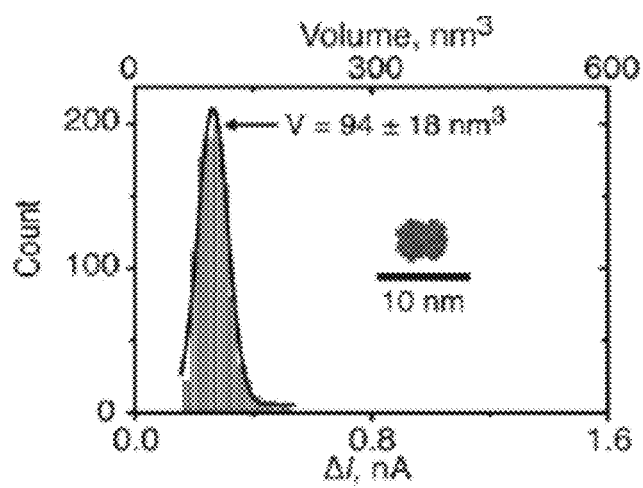
Figure 4B:
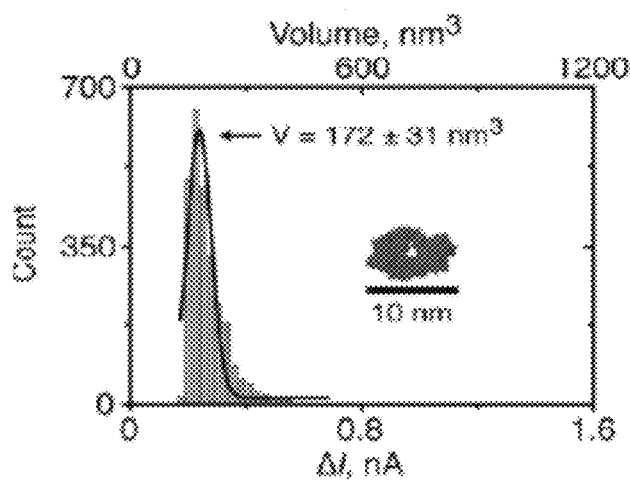
Figure 4C:
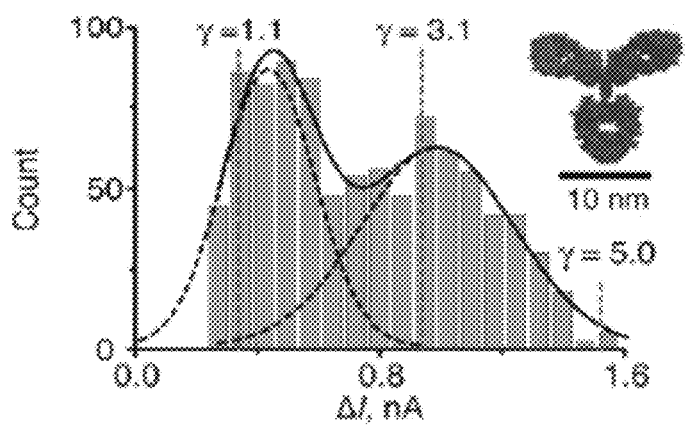

In this equation, γ (unitless) represents a shape factor52 with a value of 1.5 for spheres, Va (V) is the total applied voltage, and S(rP/dM) is a correction factor that depends on the relative values of rP and the diameter of the molecule, dM. Like most groups, we used a value of 1 for S(rP, dM) for all calculations12,13. Since Λ(t) from the translocation of spheroidal particles is approximately equal to the molecular volume of the particles14,29, we were able to estimate the molecular volumes of streptavidin (94±18 nm3; lit. value: 105±3 nm3)53, Fab fragments (172±31 nm3; lit. value: ~140 nm3)54, and antibodies (308-696 nm3; lit. value: 347±15 nm3)55. The distributions of ΔI values for streptavidin (FIG. 4a) and Fab fragments (FIG. 4b) were significantly narrower than the distribution for the antibodies (FIG. 4c). Since control experiments revealed that the broad distribution was not caused by contamination of the antibody sample with other proteins (see Supplementary Section S6), we attribute the broad distribution of ΔI values in FIG. 4c primarily to the complex molecular shape of IgG antibodies (γ≠1.5) compared to the approximately spherical shape (γ≈1.5) of streptavidin and Fab fragments (for a detailed discussion on the proposed effect of molecular shape on ΔI, see Supplementary Section S6).

Example 5

Determining Translocation Time and Charge of Different Proteins

Figure 3C:
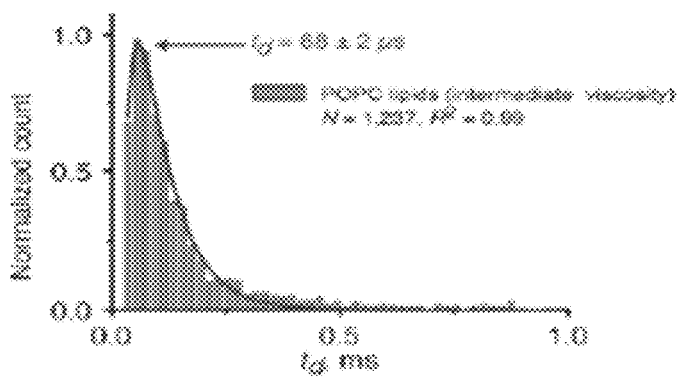

FIG. 3 shows that different proteins moved through the nanopores at different, truly distributed speeds as expected for biased diffusion first passage time processes14. Because we performed the experiments with streptavidin using a different pore (see Supplementary Table 51 for dimensions of pores used for all experiments), a direct comparison of the most frequently observed td values was only possible between Fab fragments (78±5 μs, blue bars in FIG. 3b) and monoclonal antibodies (54±8 μs; FIG. 3c). The observed differences in td values added a third dimension for distinguishing between different proteins in addition to comparing their affinity to specific ligands based on the frequency of translocation events (FIG. 2c) and quantifying their molecular volumes based on ΔI values (FIG. 4a-c).

Since the translocation speed of different lipid-anchored proteins varied, we hypothesized that the fluid nature of the pore walls may minimize non-specific adsorption processes and open the door to determining the net charge of proteins. To test this hypothesis, we developed the simplest possible model that yields a relationship between td of a lipid-anchored protein and the net charge of this protein, |z|×e, based on a model introduced recently by Sexton et al26. Here z (unitless) is the net valency of the overall charge on the protein and e (C) is the elementary charge of an electron. This model assumed that a charged protein experiences an electrophoretic force that is opposed by the viscous drag inside the pore and leads to a constant drift velocity (lP/td) through the pore. It also assumed that the viscous drag of lipid-anchored proteins is determined by the diffusion constant of the lipid anchor, DL (m2 s-1) in the lipid bilayer rather than by the diffusion constant of the protein in the aqueous electrolyte inside the pore lumen50. Based on these assumptions, we derived equation (3) to predict td values theoretically (for a detailed derivation and additional assumptions made, see Supplementary Section S8):

$$t_d = \frac{l_P^2 k_B T}{|z| e V_P D_L} \quad (3)$$

Here kB (J K-1) is the Boltzmann constant, T (K) is temperature and Vp (V) refers to the part of the total applied voltage that drops inside the pore; it does not include the voltage drop due to the access resistance to and from the pore (see Supplementary Section S8).

Figure 5:
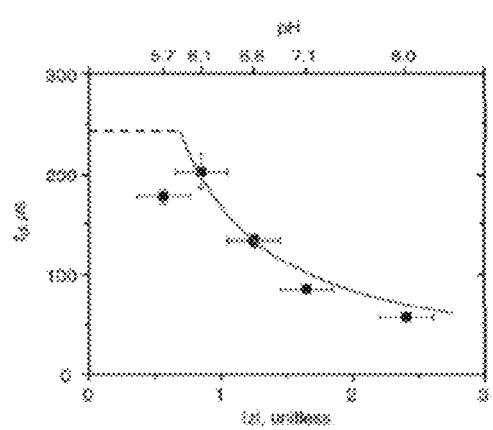

Equation (3) made it possible to compare theoretically predicted td values with experimentally determined values for proteins with known net charge. FIG. 5 shows this comparison for translocation events of streptavidin at five different pH values in the recording electrolyte and therefore five different values of |z|. The excellent agreement between the data (black squares) and the predicted td values (red curve) supports the simple model used for the derivation of equation (3).

Additional support for this model stems from a comparison between two bilayer coatings of different viscosity. In one experiment we coated the nanopore with a POPC bilayer and in the other experiment with a DΔPPC bilayer. Before adding streptavidin to the top compartment of the chips, we determined the lateral diffusion coefficient of lipids in the POPC bilayer (DL=1.13±0.11 nm2 μs-1) and in the DΔPPC bilayer (DL=1.56±0.16 nm2 μs-1) by fluorescence recovery after photobleaching (FRAP) experiments on the silicon nitride support (see Supplementary Section S2)57. With these $D_L$ values and a valence of net charge of $|z|=|-1.9\pm0.4|$ at pH 7.456, equation (3) predicted a translocation time for streptavidin of 126±29 µs in POPC-coated pores and of 91±21 µs in DΔPPC-coated pores. Experimentally, the most frequently observed translocation time of streptavidin (FIG. 3a) was 114±15 µs through pores with a POPC coating (deviation from the predicted value: −10%) and 81±10 µs through pores with a DΔPPC coating (deviation from the predicted value: −11%). The excellent agreement between the theoretically predicted values of td and the experimentally measured td values as well as the data in Table 2 confirm that translocation times of lipid-anchored analytes were indeed dominated by the viscosity of the bilayer50 and were hence independent of the shape of the proteins (FIG. 3b,c).

TABLE 2

Comparison of diffusion coefficients of lipid-anchored proteins within the nanopore, $D_P$, with diffusion coefficients of lipids, $D_L$, in coatings of two different lipid bilayers on three different nanopores.

| Protein | Lipid bilayer[a] | $D_L^b$ (nm² µs⁻¹) | $D_P^c$ (nm² µs⁻¹) | ΔD % |
|---|---|---|---|---|
| SA[d] | DΔPPC | 1.56 ± 0.16 | 1.7 ± 0.4 | +9 |
| SA[d] | POPC | 1.13 ± 0.11 | 1.2 ± 0.3 | +6 |
| SA[e] | POPC | 1.65 ± 0.17 | 1.9 ± 0.5 | +15 |
| mAb[f] | POPC | 1.29 ± 0.13 | 2.6 ± 0.7 | +100 |
| Fab[f] | POPC | 1.27 ± 0.13 | 1.5 ± 0.2 | +18 |

[a]All lipid bilayers also contained 0.15-0.4 mol % of biotin-PE.
[b]Values for $D_L$ were determined by FRAP as described in Supplementary Section S2.
[c]Values for $D_P$ were determined with equation (3) based on the most frequently measured values of $t_d$ and values of $|z|$ for SA from Sivasankar et al[56] and values of $|z|$ for mAb and Fab as determined by capillary electrophoresis (see Supplementary Section S8).
[d]Nanopore dimensions: $r_P$ = 10.0 nm, $l_P$ = 18 nm
[e]Nanopore dimensions: $r_P$ = 10.5 nm, $l_P$ = 18 nm
[f]Nanopore dimensions: $r_P$ = 16.5 nm, $l_P$ = 22 nm These observations raise the possibility to use $t_d$ values, in analogy to migration times in electrophoresis, for distinguishing between, and possibly identifying, specific proteins. The agreement between theory and experiment also suggests that determining translocation times of lipid-anchored proteins through a bilayer-coated nanopore makes it possible to determine the net charge of proteins. For instance, at pH 7.4, the measured $t_d$ values suggest a net charge between −2.9 and −5.3 for the polyclonal anti-biotin Fab fragments and a net charge of −4.2±0.5 for the monoclonal anti-biotin antibodies (see Supplementary Section S8). These values agree well with results from capillary electrophoresis experiments (see Supplementary Section S8). Moreover, for a protein with known charge, translocation experiments combined with equation (3), make it possible to determine—non-optically—the lateral diffusion constants of lipids and therefore the fluidity of bilayers within seconds (Table 2). This attribute might be useful to test therapeutic compounds for their propensity to change membrane fluidity[57].

Finally, the agreement between predicted and experimental $t_d$ values suggests that the measured $t_d$ values are close to the "true" electrophoretic translocation times. In other words, these measured translocation times represent translocation in the absence of non-specific adsorption of proteins to the bilayer coating or to the silicon nitride substrates. This point is important because all single-molecule translocation experiments with proteins reported so far were hampered by non-specific adsorption of proteins to the nanopore walls with regard to accurate determination of $t_d$ values[1,14,26]. In some cases, these interactions increased the translocation times of proteins by several orders of magnitude[26].

Example 6

Fluid Walls Translocate Aggregated Aβ Peptides without Clogging

Figure 6A:
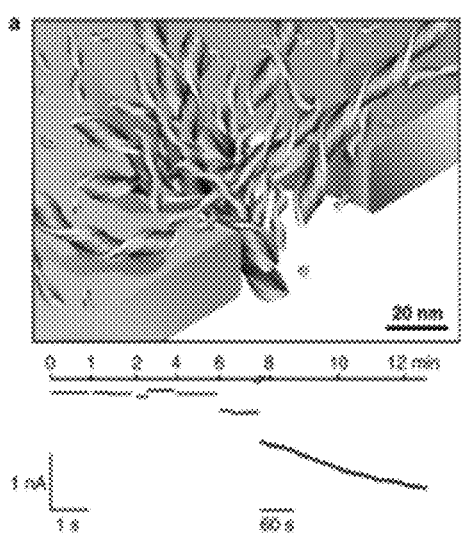
Figure 6B:
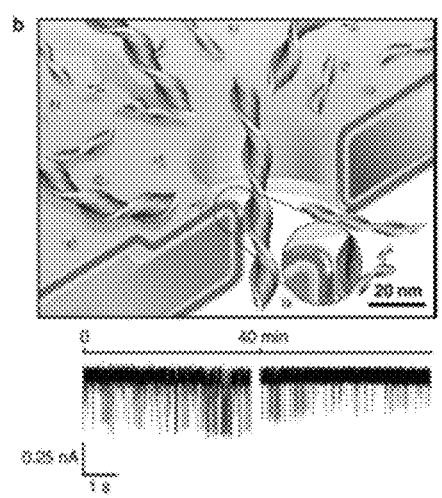

Due to the unique capability of fluid bilayer coatings to eliminate non-specific interactions, these pores made it possible to analyze translocation events of molecules that aggregate and have a tendency to clog nanopores. Amyloidogenic peptides, such as Alzheimer's disease-related amyloid-β (Aβ) peptides[58], belong to this category of molecules. The current versus time trace in FIG. 6a shows that a nanopore without a bilayer coating clogged within minutes after addition of Aβ peptides. Despite several attempts, we were never able to detect translocation events from samples of Aβ peptides with uncoated pores. In contrast, FIG. 6b illustrates that coating nanopores with bio-inspired, fluid lipid bilayers incurred non-fouling properties to these pores and made it possible to detect numerous large amplitude translocation events due to the passage of individual Aβ oligomers and fibrils.

References for Methods Section and for Examples 1-6
1 Sexton, L. T. et al. Resistive-pulse studies of proteins and protein/antibody complexes using a conical nanotube sensor. *J. Am. Chem. Soc.* 129, 13144-13152 (2007).
2 Movileanu, L., Howorka, S., Braha, O. & Bayley, H. Detecting protein analytes that modulate transmembrane movement of a polymer chain within a single protein pore. *Nature Biotech.* 18, 1091-1095 (2000).
3 Howorka, S. & Siwy, Z. Nanopore analytics: sensing of single molecules. *Chem. Soc. Rev.* 38, 2360-2384 (2009).
4 Siwy, Z. et al. Protein biosensors based on biofunctionalized conical gold nanotubes. *J. Am. Chem. Soc.* 127, 5000-5001 (2005).
5 Ding, S., Gao, C. L. & Gu, L. Q. Capturing single molecules of immunoglobulin and ricin with an aptamer-encoded glass nanopore. *Anal. Chem.* 81, 6649-6655 (2009).
6 Uram, J. D., Ke, K., Hunt, A. J. & Mayer, M. Submicrometer pore-based characterization and quantification of antibody-virus interactions. *Small* 2, 967-972 (2006).
7 Branton, D. et al. The potential and challenges of nanopore sequencing. *Nature Biotech.* 26, 1146-1153 (2008).
8 Iqbal, S. M., Akin, D. & Bashir, R. Solid-state nanopore channels with DNA selectivity. *Nature Nanotech.* 2, 243-248 (2007).
9 Wanunu, M., Morrison, W., Rabin, Y., Grosberg, A. Y. & Meller, A. Electrostatic focusing of unlabelled DNA into nanoscale pores using a salt gradient. *Nature Nanotech.* 5, 160-165 (2010).
10 Uram, J. D., Ke, K., Hunt, A. J. & Mayer, M. Label-free affinity assays by rapid detection of immune complexes in submicrometer pores. *Angew. Chem.-Int. Edit.* 45, 2281-2285 (2006).
11 Robertson, J. W. F. et al. Single-molecule mass spectrometry in solution using a solitary nanopore. *Proc. Natl. Acad. Sci. U.S.A.* 104, 8207-8211 (2007).
12 Han, A. P. et al. Label-free detection of single protein molecules and protein-protein interactions using synthetic nanopores. *Anal. Chem.* 80, 4651-4658 (2008).
13 Ito, T., Sun, L. & Crooks, R. M. Simultaneous determination of the size and surface charge of individual nanoparticles using a carbon nanotube-based coulter counter. *Anal. Chem.* 75, 2399-2406 (2003).

14 Talaga, D. S. & Li, J. L. Single-molecule protein unfolding in solid state nanopores. *J. Am. Chem. Soc.* 131, 9287-9297 (2009).

15 Oukhaled, G. et al. Unfolding of proteins and long transient conformations detected by single nanopore recording. *Phys. Rev. Lett.* 98, 158101 (2007).

16 Benner, S. et al. Sequence-specific detection of individual DNA polymerase complexes in real time using a nanopore. *Nature Nanotech.* 2, 718-724 (2007).

17 Clarke, J. et al. Continuous base identification for single-molecule nanopore DNA sequencing. *Nature Nanotech.* 4, 265-270 (2009).

18 Bayley, H. & Cremer, P. S. Stochastic sensors inspired by biology. *Nature* 413, 226-230 (2001).

19 Nakane, J. J., Akeson, M. & Marziali, A. Nanopore sensors for nucleic acid analysis. *J. Phys. Condens. Matter* 15, R1365-R1393 (2003).

20 Dekker, C. Solid-state nanopores. *Nature Nanotech.* 2, 209-215 (2007).

21 Martin, C. R. & Siwy, Z. S. Learning nature's way: Biosensing with synthetic nanopores. *Science* 317, 331-332 (2007).

22 Movileanu, L. Interrogating single proteins through nanopores: challenges and opportunities. *Trends Biotechnol.* 27, 333-341 (2009).

23 Majd, S. et al. Applications of biological pores in nanomedicine, sensing, and nanoelectronics. *Curr. Opin. Biotechnol.* 21, 439-476 (2010).

24 Hou, X. et al. A biomimetic potassium responsive nanochannel: G-Quadruplex DNA conformational switching in a synthetic nanopore. *J. Am. Chem. Soc.* 131, 7800-7805 (2009).

25 Yameen, B. et al. Single conical nanopores displaying pH-tunable rectifying characteristics. Manipulating ionic transport with zwitterionic polymer brushes. *J. Am. Chem. Soc.* 131, 2070-2071 (2009).

26 Sexton, L. T. et al. An adsorption-based model for pulse duration in resistive-pulse protein sensing. *J. Am. Chem. Soc.* 132, 6755-6763 (2010).

27 Pedone, D., Firnkes, M. & Rant, U. Data analysis of translocation events in nanopore experiments. *Anal. Chem.* 81, 9689-9694 (2009).

28 Uram, J. D., Ke, K. & Mayer, M. Noise and bandwidth of current recordings from submicrometer pores and nanopores. *ACS Nano* 2, 857-872 (2008).

29 Fologea, D., Ledden, B., David, S. M. & Li, J. Electrical characterization of protein molecules by a solid-state nanopore. *Appl. Phys. Lett.* 91, 053901 (2007).

30 Chun, K. Y., Mafe, S., Ramirez, P. & Stroeve, P. Protein transport through gold-coated, charged nanopores: Effects of applied voltage. *Chem. Phys. Lett.* 418, 561-564 (2006).

31 Hille, B. *Ion Channels of Excitable Membranes*. (Sinauer Associates, Inc., Sunderland, 2001).

32 Steinbrecht, R. A. Pore structures in insect olfactory sensilla: A review of data and concepts. *Int. J. Insect Morphol. Embryol.* 26, 229-245 (1997).

33 Zacharuk, R. Y. Antennae and Sensilla in *Comparative Insect Physiology Chemistry and Pharmacology* (ed. G. A. Kerkut & L. I. Gilbert) (Pergamon Press, Oxford, 1985).

34 Locke, M. Permeability of insect cuticle to water and lipids. *Science* 147, 295-298 (1965).

35 Nilsson, J., Lee, J. R. I., Ratto, T. V. & Letant, S. E. Localized functionalization of single nanopores. *Adv. Mater.* 18, 427-431 (2006).

36 Wang, G. L., Zhang, B., Wayment, J. R., Harris, J. M. & White, H. S. Electrostatic-gated transport in chemically modified glass nanopore electrodes. *J. Am. Chem. Soc.* 128, 7679-7686 (2006).

37 Wanunu, M. & Meller, A. Chemically modified solid-state nanopores. *Nano Lett.* 7, 1580-1585 (2007).

38 Lewis, B. A. & Engelman, D. M. Lipid bilayer thickness varies linearly with acyl chain-length in fluid phosphatidylcholine vesicles. *J. Mol. Biol.* 166, 211-217 (1983).

39 Caffrey, M. & Hogan, J. LIPIDAT: A database of lipid phase transition temperatures and enthalpy changes. DMPC data subset analysis. *Chem. Phys. Lipids* 61, 1-109 (1992).

40 Watts, T. H., Brian, A. A., Kappler, J. W., Marrack, P. & McConnell, H. M. Antigen presentation by supported planar membranes containing affinity-purified I-Ad. Proc. Natl. Acad. Sci. U.S.A. 81, 7564-7568 (1984).

41 Cremer, P. S. & Boxer, S. G. Formation and spreading of lipid bilayers on planar glass supports. *J. Phys. Chem. B* 103, 2554-2559 (1999).

42 Reimhult, E., Hook, F. & Kasemo, B. Intact vesicle adsorption and supported biomembrane formation from vesicles in solution: Influence of surface chemistry, vesicle size, temperature, and osmotic pressure. *Langmuir* 19, 1681-1691 (2003).

43 Sackmann, E. Supported membranes: Scientific and practical applications. *Science* 271, 43-48 (1996).

44 Miller, C. E., Majewski, J., Gog, T. & Kuhl, T. L. Characterization of biological thin films at the solid-liquid interface by X-ray reflectivity. *Phys. Rev. Lett.* 94 (2005).

45 Bayerl, T. M. & Bloom, M. Physical-properties of single phospholipid-bilayers adsorbed to micro glass-beads—a new vesicular model system studied by H-2-nuclear magnetic-resonance. *Biophys. J.* 58, 357-362 (1990).

46 Tokumasu, F., Jin, A. J. & Dvorak, J. A. Lipid membrane phase behaviour elucidated in real time by controlled environment atomic force microscopy. *J. Electron Microsc.* 51, 1-9 (2002).

47 Schuy, S. & Janshoff, A. Thermal expansion of microstructured DMPC bilayers quantified by temperature-controlled atomic force microscopy. *ChemPhysChem* 7, 1207-1210 (2006).

48 Gibbs, A. G. Lipid melting and cuticular permeability: new insights into an old problem. *J. Insect Physiol.* 48, 391-400 (2002).

49 Adam, G. & Delbrueck, M. Reduction of Dimensionality in Biological Diffusion Processes in *Structural Chemistry and Molecular Biology* (ed. A. Rich & N. Davidson) 198-215 (W. H. Freeman and Company, San Francisco, 1968).

50 Gambin, Y. et al. Lateral mobility of proteins in liquid membranes revisited. *Proc. Natl. Acad. Sci. U.S.A.* 103, 2098-2102 (2006).

51 Grover, N. B., Naaman, J., Ben-sasson, S., Doljansk, F. & Nadav, E. Electrical sizing of particles in suspensions. 2. Experiments with rigid spheres. *Biophys. J.* 9, 1415-1425 (1969).

52 Grover, N. B., Naaman, J., Ben-sasson, S. & Doljansk, F. Electrical sizing of particles in suspensions. I. Theory. *Biophys. J.* 9, 1398-1414 (1969).

53 Neish, C. S., Martin, I. L., Henderson, R. M. & Edwardson, J. M. Direct visualization of ligand-protein interactions using atomic force microscopy. *Br. J. Pharmacol.* 135, 1943-1950 (2002).

54 Janeway, C. A. *Immunobiology: the immune system in health and disease*. 5th edn, (Garland Publishing, New York, 2001).

55 Schneider, S. W., Larmer, J., Henderson, R. M. & Oberleithner, H. Molecular weights of individual proteins correlate with molecular volumes measured by atomic force microscopy. *Pflugers Arch.* 435, 362-367 (1998).

56 Sivasankar, S., Subramaniam, S. & Leckband, D. Direct molecular level measurements of the electrostatic properties of a protein surface. *Proc. Natl. Acad. Sci. U.S.A.* 95, 12961-12966 (1998).

57 Majd, S. & Mayer, M. Hydrogel stamping of arrays of supported lipid bilayers with various lipid compositions for the screening of drug-membrane and protein-membrane interactions. *Angew. Chem.-Int. Edit.* 44, 6697-6700 (2005).

58 Capone, R. et al. Amyloid-beta-induced ion flux in artificial lipid bilayers and neuronal cells: Resolving a controversy. *Neurotox. Res.* 16, 1-13 (2009).

59 Li, J. et al. Ion-beam sculpting at nanometre length scales. *Nature* 412, 166-169 (2001).

Example 7

Single Particle Characterization of Aβ Oligomers in Solution.

Figure 8A:
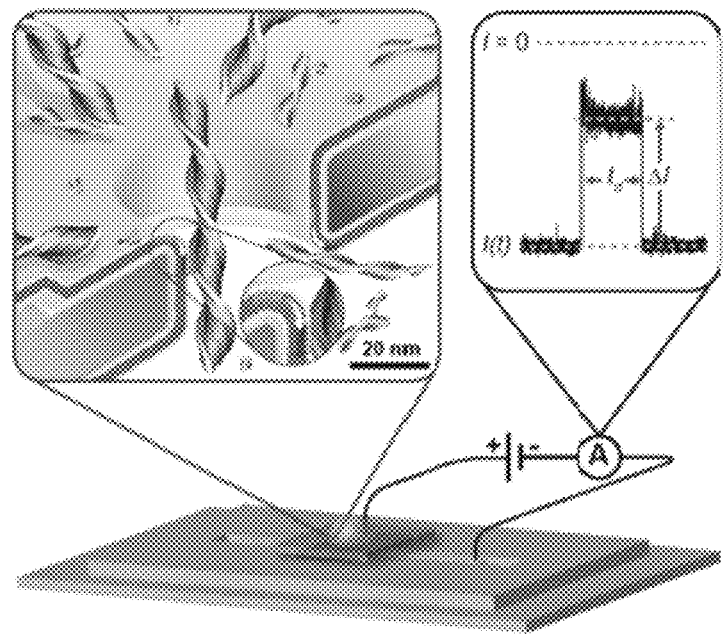

Here, we extend the use of lipid-coated nanopores from analyzing Aβ fibers to characterizing the smaller and clinically more relevant soluble oligomeric Aβ species. The lipid coating of the nanopore (FIG. 8A inset) is required for detection of Aβ aggregates since nanopores without the fluid coating clogged due to adsorption of Aβ on the nanopore walls (see Supporting Information S11).[35] We show that resistive pulse sensing with lipid-coated nanopores can be used to track the time-dependent aggregation of $A\beta_{(1-40)}$ by monitoring the distribution of Aβ aggregates in solution, and we validated this method by analyzing transmission electron microscopy micrographs of $A\beta_{(1-40)}$ aggregates.

To perform nanopore-based detection of $A\beta_{(1-40)}$ aggregates, we started from aqueous solutions containing mostly $A\beta_{(1-40)}$ monomers (see Supporting Information S12). We prepared aggregates of $A\beta_{(1-40)}$ by incubating these solutions for zero to three days before adding them to the electrolyte in the top compartment of the recording setup (FIG. 8A).[20,52] We confirmed by gel electrophoresis that this preparation method resulted in increasing aggregate sizes over time (see Supporting Information S13).[52]

Figure 8B:
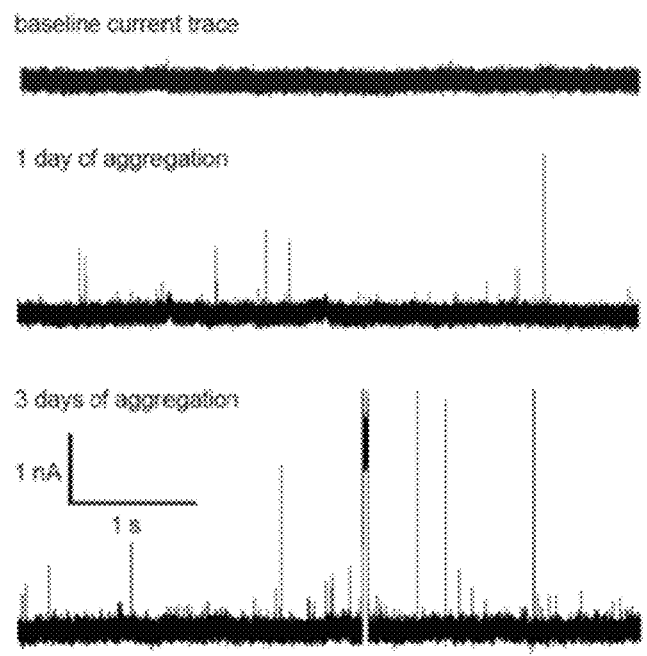
Figure 9A:
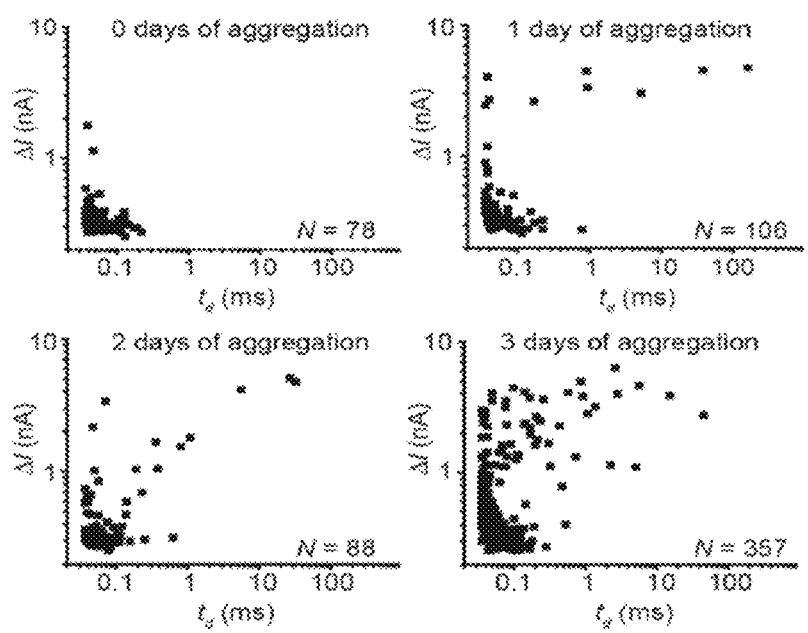
Figure 9B:
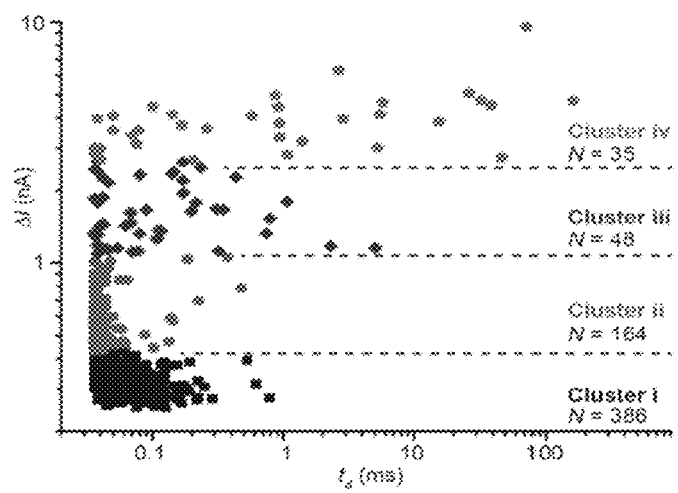

FIG. 8B shows recordings of the baseline current before and after adding $A\beta_{(1-40)}$ solutions that had been permitted to aggregate for one and three days. Consistent with time-dependent aggregation, the current trace from the three-day sample shows resistive pulses with increased frequency and larger amplitude than the current trace from the one-day sample. FIG. 9A shows scatter plots of ΔI versus $t_d$ values for translocation events with a ΔI value greater than 250 pA (5 times the standard deviation of the noise) and with a $t_d$ value greater than 35 μs (the smallest $t_d$ value we can measure accurately).[35,53] As expected, the values of ΔI, and hence the sizes of aggregates, increased with increasing aggregation time. Interestingly, the amplitude of ΔI values reached a maximum at ~5 nA (~10% of the baseline current magnitude), despite large variations in $t_d$ values (FIG. 9B, cluster iv). This result is consistent with translocation of cylindrical objects with similar diameters but varying lengths that are longer than the length of the nanopore, since the sensing zone is limited to the volume of the nanopore and its effective length. These characteristics apply to protofibrils, which have lengths up to 200 nm, and fibers, which have can reach lengths up several μm. Both types of aggregates have constant diameters along their length, and therefore, resistive pulses due to their translocation will have a maximum ΔI value but very distributed $t_d$ values.[8,21]

In order to distinguish among resistive pulses resulting from the translocation of spherical oligomers, protofibrils or fibers through the nanopore, we performed a cluster analysis on a data set from all resistive pulses (FIG. 9B) based on the ΔI and $t_d$ value for each translocation event. To perform the cluster analysis we used the Fuzzy algorithm in the open-source, statistics software R and set the number of clusters to four, since we expected four clusters of ΔI versus $t_d$ values to emerge representing the translocation of: (i) spherical oligomers, (ii) cylindrical protofibrils with lengths shorter than the effective length of the nanopore, (iii) cylindrical protofibrils with lengths longer than the effective length of the nanopore, or (iv) fibers with a length longer than the effective length of the nanopore. The colored points in FIG. 9B illustrate the resulting assignment given to each recorded resistive pulse. FIG. 9B also reveals the expected result that clusters (iii) and (iv) contain resistive pulses with ΔI values that converge at 1 to 2 nA and at 3 to 4 nA, respectively, while their $t_d$ values vary by four orders of magnitude (35 us to 100 ms), suggesting these clusters contain resistive pulses due to the translocation of protofibrils and fibers with lengths longer than the length of the nanopore and with somewhat constant diameters.

To determine the size of $A\beta_{(1-40)}$ aggregates in each cluster, we used the value of ΔI from each translocation event and considered two extreme cases yielding two different equations.[35,47,57] Equation (3) describes the relationship between ΔI and the excluded volume, Λ(nm³), of spherical oligomers,[58-61] while equation (4) describes the relationship between ΔI and the average cross-sectional area, $A_X$ (nm²), of aggregates with lengths longer than the effective length of the nanopore.[57,62]

$$\Delta I = \frac{\gamma V_A \Lambda}{\rho(l_P + 1.6 r_P)^2} \text{ for } l_M < l_{\text{eff}} \qquad (3)$$

$$\Delta I = \frac{\gamma V_A A_X}{\rho(l_P + 1.6 r_P)} \text{ for } l_M > l_{\text{eff}} \qquad (4)$$

In these equations, γ is a shape factor (equal to a value of 1.5 for globular spheres and a value of 1.0 for long cylinders aligned parallel to the electric field),[47,48,63-66] $V_A$ (V) is the applied electric potential difference, p m) is the resistivity of the electrolyte solution, $l_P$ (m) is the length of the nanopore, $r_P$ (m) is the radius of the nanopore, and $l_M$ is the length of the protofibril or fiber. The effective length of the cylindrical nanopore, $l_{\text{eff}}$, is defined by the term ($l_P$+1.6$r_P$) in the denominator of equations (3) and (4), and it accounts for the extension of the electric field lines from the nanopore into the bulk solution.[67]

Figure 10A:
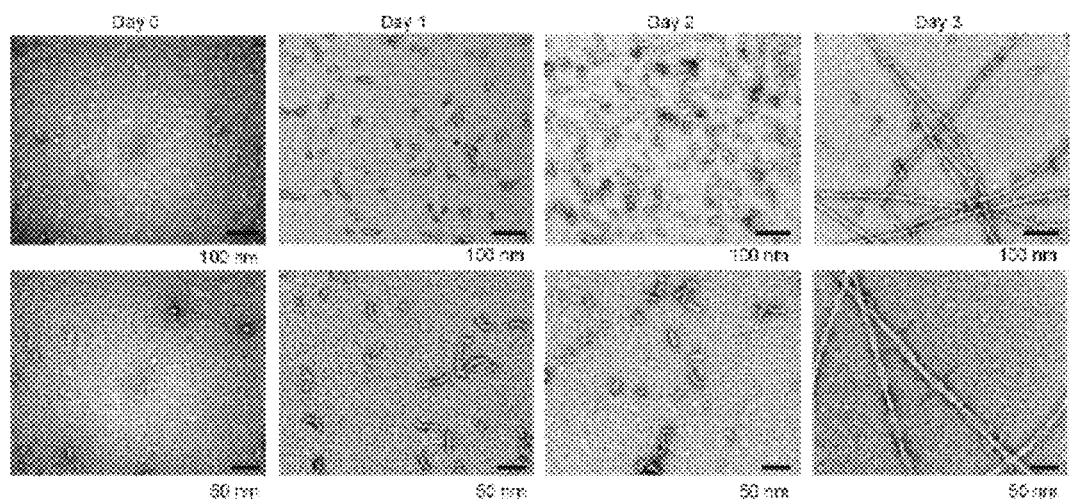
Figure 10B:
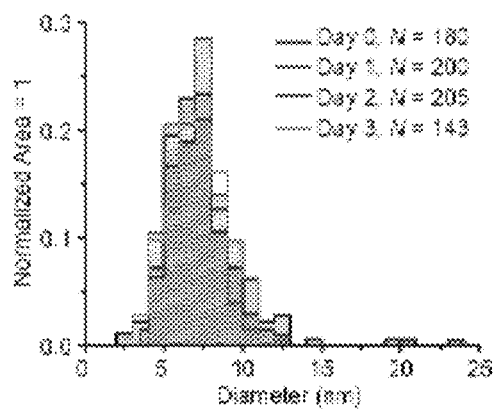
Figure 10C:
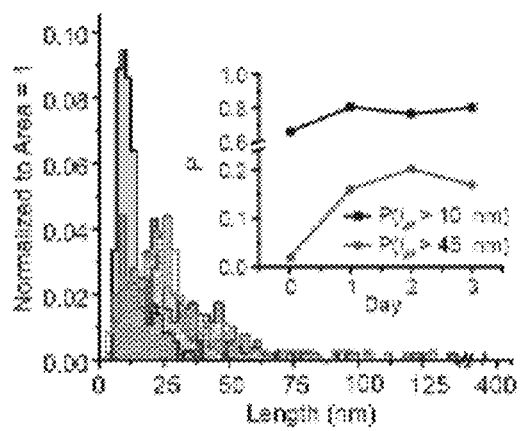
Figure 10D:
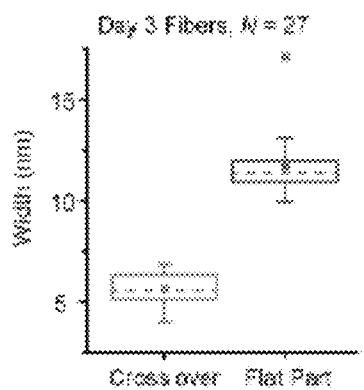

Table 3 lists the mean value of ΔI and the range of ΔI values that we measured for each cluster as well as the values for the excluded volume that we calculated using equation (1) for cluster (i) and the values for the cross-sectional areas that we calculated using equation (2) for clusters (iii) and (iv). Table 3 also compares the sizes of $A\beta_{(1-40)}$ aggregates as determined from resistive-pulse analysis with those that we determined from analysis of TEM images from the same samples (FIG. 10) as well as with those reported in literature. For instance, the mean ΔI of the resistive pulses in cluster (i) corresponds to a spherical diameter of 5.5 nm (with a range of 5-6 nm), and we measured via TEM that the smallest spherical aggregates had an average diameter of 6.2±1.2 nm (N=18) (FIG. 3A). Similarly, the mean ΔI of the resistive pulses in cluster (iii) due to protofibrils with $l_M > l_{eff}$ corresponds to a cylindrical diameter of 4.4 nm (with a range of 3.6 to 5.6 nm). In TEM micrographs, we observed protofibrils with an average diameter of 6.4±1.5 nm (N=117) and with lengths ranging from ~6 nm to 350 nm (FIGS. 10B & 10C); the reported diameter of protofibrils in literature is ~5 nm.[19,21] Finally, the mean ΔI of resistive pulses in cluster (iv) due to fibers corresponds to a cross-sectional-area of 36 nm² (with a range of 25 nm² to 88 nm²). From the TEM micrographs, we estimated the cross-sectional area of $A\beta_{(1-40)}$ fibers to be 51±10 nm² (N=27) based on the two visible widths of the twisting fibers of 5.6±0.8 nm and 11.5±1.5 nm (FIG. 10A: Day 3 and FIG. 10D). The literature values of the cross-sectional areas of amyloid fibers range from 30 nm² to 90 nm².[2,22,23,27] For these three forms of $A\beta_{(1-40)}$ aggregates, the general agreement among the sizes determined from resistive-pulse analysis with those determined by TEM analysis and those reported in literature demonstrates that resistive-pulse analysis makes it possible to characterize Aβ oligomers, protofibrils, and fibers. This agreement also indicates that the cluster analysis produced reasonable assignments for the majority of the resistive pulses. We provide additional evidence for the accuracy of the cluster analysis in Supporting Information S14.

consistent with reduced diffusive spreading due to accelerated motion through the pore as a result of reduced viscous drag on aggregates in cluster (ii) compared to those in cluster (i) (see Supporting Information S15 for distributions of $t_d$ values in clusters i and ii).[57,62] Indeed, prolate spheroids moving parallel to their long axis experience less viscous drag than a spherical particle of similar volume.[73] These effects combined with the strong electrophoretic force on an aggregate due to the net negative charge of an Aβ monomer of −3 at pH 7.0[15,74] and the high electric field in the nanopore ($V_A/l_{eff}=4.5 \times 10^6$ V m$^{-1}$) likely orients protofibril aggregates with their length axis parallel to the electric field in in the nanopore. The second assumption, based on results by Kellermayer et al., was that the elongation of Aβ protofibrils occurs at a constant diameter, $\theta_C$, for lengths greater than 6.5 nm.[8] We confirmed the validity of this assumption by TEM analysis of the samples used here (see FIG. 10 and Supporting Information S16). Consequently, the excluded volume of these protofibrils could be described by the equation of cylinder, $\Lambda = \frac{1}{4} \pi \theta_C^2 l_M$, and a system of equations that includes the shape factor $\gamma_\parallel$ as a function of the length of the aggregate, $l_M$, and ΔI as a function of $\gamma_\parallel$ and $l_M$. We summarized the details of these equations, the resulting shape factors, and results of this analysis in the Supporting Information S17. Solving this system of equations while using the values of ΔI from the resistive pulses in cluster (ii)

TABLE 3

Average values of ΔI, excluded volumes Λ, diameters of spherical $A\beta_{(1-40)}$ aggregates $\theta_s$, and cross-sectional areas $A_x$ as well the corresponding cylindrical diameter $\theta_c$ of rod-shaped $A\beta_{(1-40)}$ aggregates in each cluster compared to equivalent values measured via TEM and values reported in literature.

| cluster | ⟨ΔI⟩ (min, max) pA | Λ (min, max) nm³ | θs (min, max) nm | TEM Values nm | literature value nm |
|---|---|---|---|---|---|
| (i): spherical oligomers | 324 (250, 432) | 85 (66[a], 113) | 5.5 (5.0, 6.0) | θc = 6.2 ± 1.2 | — |
| (ii): protofibrils $I_M \leq I_{eff}$ | 596 (433, 1051) | 206 (189, 388) | — | θc = 6.5 ± 2.0 | θc = 5 [Ref. 19,21] |

| cluster | ⟨ΔI⟩ pA | $A_x$ nm² | θs nm | TEM Values nm | literature value nm |
|---|---|---|---|---|---|
| (iii): protofibrils $I_M > I_{eff}$ | 1655 (1087, 2639) | 15 (10, 24) | 4.4 (3.6, 5.6) | θc = 6.4 ± 1.5 | θc = 5 [Ref. 19,21] |
| (iv): fibers $I_M \gg I_{eff}$ | 3792 (2669, 9552) | 36 (25, 88) | 6.7 (5.6, 10.6) | [b]$W_1$ = 5.6 ± 0.8 $W_2$ = 11.5 ± 1.5 Ax = 54 ± 10 nm² | $W_1$ = 6.6 [Ref. 22] $W_2$ = 13.2 [Ref. 22] Ax = 30-90 nm² [Ref. 22,23,27] |

[a]Using the average molecular weight density of $A\beta_{(1-40)}$ aggregates of 0.81 kDa/nm³ [Ref. 22,68] and the molecular weight of an $A\beta_{(1-40)}$ monomer of 4.3 kDa, the smallest spherical oligomers detected in cluster (i) contained approximately 12 monomers.
[b]$W_1$ and $W_2$ refer to the widths of twisting $A\beta_{(1-40)}$ fibers when the fibers are twisted or crossing over themselves, $W_1$, or when the fibers are lying flat, $W_2$, on the TEM grid (FIG. 3).[22]

In order to estimate the excluded volume, Λ, of the protofibrils with $l_M < l_{eff}$ from the resistive pulses in cluster (ii), we made two assumptions. First, protofibrils pass through the nanopore with their long-axis aligned parallel to the electric field resulting in a relatively constant shape factor that can be approximated from the shape factor of a prolate aligned parallel to an electric field, $\gamma_\parallel$. This alignment is predicted to occur because aggregates approaching the nanopore from the bulk solution experience a strong converging electric field gradient.[49,63-65,69-71] Ai and Qian recently modeled the dynamics of nanorods (1 nm×10 nm) approaching a nanopore under very similar conditions to those reported here and demonstrated that rods will completely align with their length axis parallel to the electric field prior to entering the nanopore.[72] Furthermore, the distribution of translocation times in cluster (ii) was narrower than the distribution in cluster (i) (FIG. 9B), which is and the diameter of protofibrils with $l_M > l_{eff}$ from cluster (iii) (Table 3, $\theta_C$=4.4 nm), this analysis returned shape factors for each translocation event in cluster (ii) that ranged from $\gamma_\parallel$=1.048 to 1.2 (average $\gamma_\parallel$=1.13) and excluded volumes that ranged from 189 nm³ to 388 nm³ (Table 3).

Figure 11:
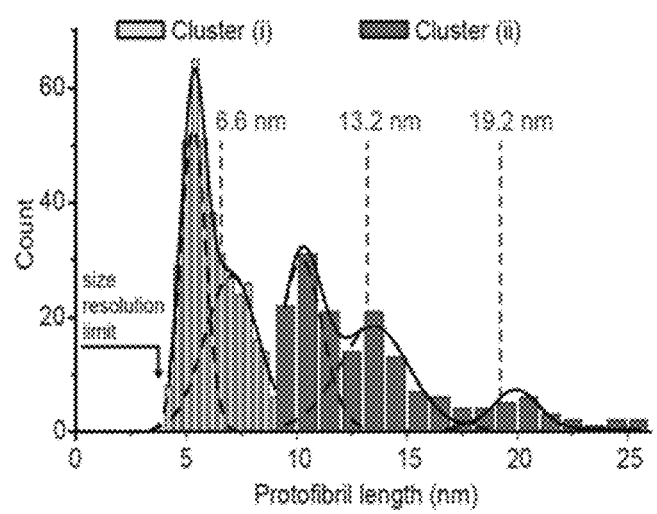

As a first attempt at examining the peaks in the distribution of $A\beta_{(1-40)}$ sizes reported by Cabriolu et al., we generated a histogram of the lengths of the protofibrils in clusters (i) and (ii) (FIG. 11) using the equations described previously and the Supporting Information S17. The dotted blue lines in FIG. 11 indicate the lengths of protofibrils at which Cabriolu et al. observed peaks in the distribution of sizes; these lengths are 6.6, 13.2, and 19.2 nm. Kellermayer et al. reported segmented growth of Aβ protofibrils generated by the 25-35 amino acid portion of $A\beta_{(1-40)}$ and leading to protofibril lengths of 6.5, 13.3, 23.2, 32.5, and 40 nm.[7,8] These reports together with the observation of several local maxima in FIG. 11 suggest that protofibrils of $A\beta_{(1-40)}$ are present in solution with certain preferred lengths corresponding to local minima in the work for fibril formation.

Figure 12:
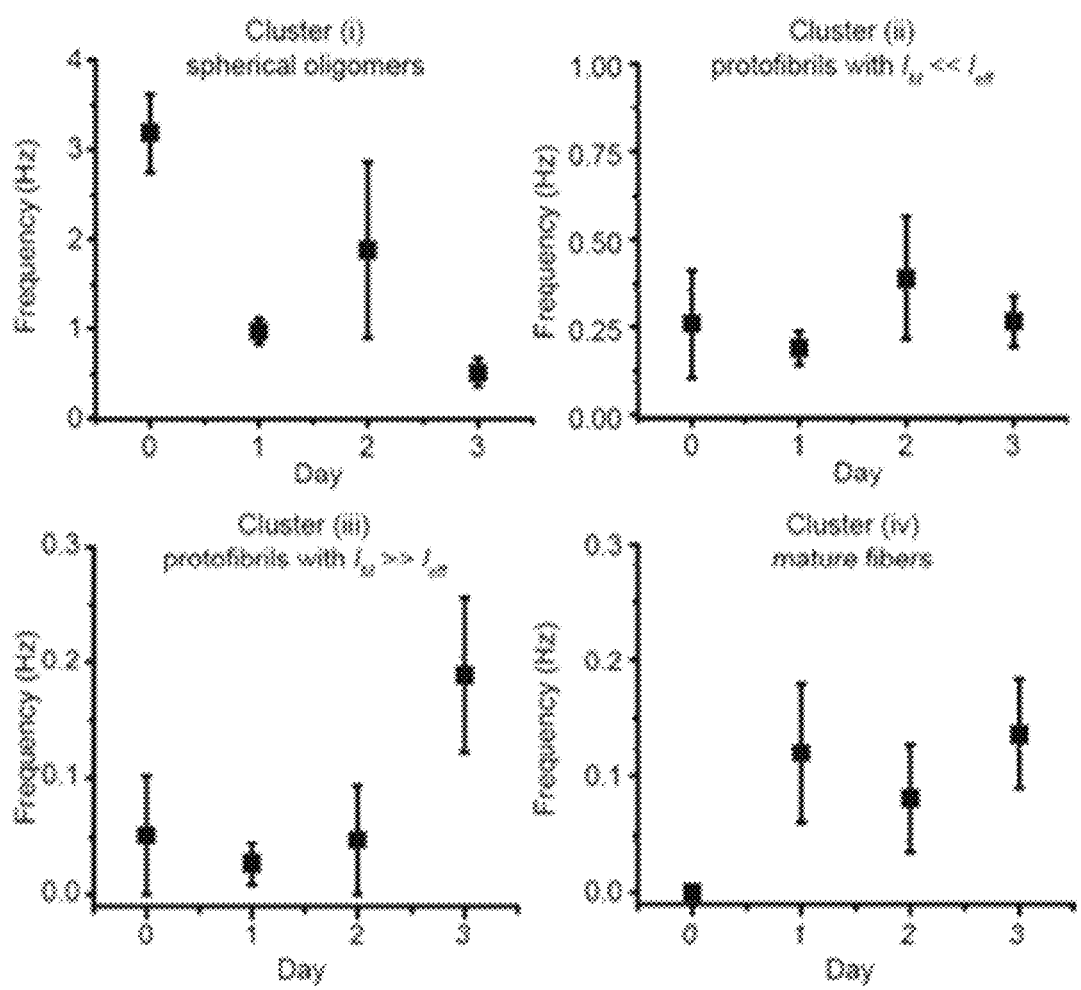

Since nanopore-based resistive pulse sensing detects single aggregates, the frequency of translocation events is proportional to the concentration and diffusion constant of the aggregate.[60,75-77] For long protofibrils and fibers, the frequency may also be affected by steric and entropic effects.[57,78,79] FIG. 12 shows the frequency of translocation events that were assigned to each cluster plotted as a function of the aggregation time. This analysis provides an indication of the changes in the concentration of aggregates within each cluster, assuming the diffusion constant and barriers to entering the nanopore are similar for aggregates within a given cluster. FIG. 12 reveals that the frequency of events due to the translocation of large, mature fibers in cluster (iv) increased over time while the frequency of events due to small spherical oligomers in cluster (i) decreased as expected for time-dependent aggregation of $A\beta$.[80] FIG. 12 also shows that the frequency of protofibril translocation in cluster (ii) remained relatively constant within the error of the measurement.

In summary, we report the use of nanopores with fluid walls for detecting and characterizing size distributions of unlabeled aggregates of $A\beta_{(1-40)}$ in situ. These distributions were obtained by measuring hundreds of single aggregates, making it possible to characterize the large range of $A\beta$ aggregate sizes and shapes. The results from this analysis agree well with those from TEM analysis of the same $A\beta$ preparations and with literature values. Several challenges remain, however, including accurately applying the shape factor, $\gamma$, to estimate the distribution of protofibril lengths in clusters (i) and (ii). To improve this analysis it would be helpful to account for possible rotation of short protofibrils with a low aspect ratio while they move through the confining pore as well as the corresponding electric field lines around the molecule.[66]

Another challenge involves the time and size resolution of the technique; currently, the smallest $A\beta$ aggregates (<dodecamers) could not be included in the analysis due to resolution limits in $\Delta I$ values and $t_d$ values. Reducing the translocation speed of $A\beta_{(1-40)}$ aggregates should improve the determination of $\Delta I$ values, reduce the $\Delta I$ threshold, and ensure that all $t_d$ values can be determined accurately. Inclusion of lipids in the bilayer coating that preferentially interact with aggregated forms of $A\beta$ such as phosphatidylserine or the ganglioside GM1[81,82] may be one strategy.

Another challenge is that the high ionic strength of the recording electrolyte accelerates the aggregation of $A\beta$ (see Supporting Information S13 and S18). Nanopores with smaller dimensions than the pore used here combined with techniques to increase translocation times may ultimately enable the use of electrolyte solutions with physiologic ionic strength in these assays.

Despite these challenges, we show that nanopore-based resistive pulse recordings made it possible to characterize the size and shape of unlabeled aggregates of disease-relevant amyloids in solution. The particular strength of nanopore sensing lies in its ability to characterize a large number of individual aggregates. This capability for single particle analysis is required to characterize $A\beta$ aggregates with a wide-ranging, dynamic heterogeneity in size and shape and as well as to proceed with attempts to correlate cytotoxicity and pathogenic mechanisms with aggregate sizes and shapes.[6]

References for Example 7
(1) Trojanowski, J. Q.; Mattson, M. P. *Neuromol. Med.* 2003, 4, 1-5.
(2) Hardy, J. *Neuron.* 2006, 52, 3-13.
(3) Schnabel, J. *Nature.* 2011, 475, S12-S14.
(4) Ding, H.; Wong, P. T.; Lee, E. L.; Gafni, A.; Steel, D. G. *Biophys. J.* 2009, 97, 912-921.
(5) Johnson, R. D.; Schauerte, J. A.; Wisser, K. C.; Gafni, A.; Steel, D. G. *PLoS One.* 2011, 6.
(6) Ono, K.; Condron, M. M.; Teplow, D. B. *Proc. Natl. Acad. Sci. U.S.A.* 2009, 106, 14745-14750.
(7) Cabriolu, R.; Kashchiev, D.; Auer, S. *Biophys. J.* 2011, 101, 2232-2241.
(8) Kellermayer, M. S. Z.; Karsai, A.; Benke, M.; Soós, K.; Penke, B. *Proc. Natl. Acad. Sci. U.S.A.* 2008, 105, 141-144.
(9) Journal of Structural BiologyGoldsbury, C. S.; Wirtz, S.; Miller, S. A.; Sunderji, S.; Wicki, P.; Aebi, U.; Frey, P. *J. Struct. Biol.* 2000, 130, 217-231.
(10) Lines, R. W. in *Particle Size Analysis* (eds Stanley-Wood, N. G.; Lines, R. W.) 352 (The Royal Society of Chemistry, 1992).
(11) Demuro, A.; Mina, E.; Kayed, R.; Milton, S. C.; Parker, I.; Glabe, C. G. *J. Biol. Chem.* 2005, 280, 17294-17300.
(12) Giuffrida, M. L.; Caraci, F.; Pignataro, B.; Cataldo, S.; De Bona, P.; Bruno, V.; Molinaro, G.; Pappalardo, G.; Messina, A.; Palmigiano, A.; Garozzo, D.; Nicoletti, F.; Rizzarelli, E.; Copani, A. *J. Neurosci.* 2009, 29, 10582-10587.
(13) Hartley, D. M.; Walsh, D. M.; Ye, C. P. P.; Diehl, T.; Vasquez, S.; Vassilev, P. M.; Teplow, D. B.; Selkoe, D. *J. Neurosci.* 1999, 19, 8876-8884.
(14) Bucciantini, M.; Giannoni, E.; Chiti, F.; Baroni, F.; Formigli, L.; Zurdo, J. S.; Taddei, N.; Ramponi, G.; Dobson, C. M.; Stefani, M. *Nature.* 2002, 416, 507-511.
(15) Hortschansky, P.; Schroeckh, V.; Christopeit, T.; Zandomeneghi, G.; Fandrich, M. *Protein Sci.* 2005, 14, 1753-1759.
(16) Zagorski, M. G.; Shao, H.; Ma, K.; Li, H.; Yang, J.; Zeng, H. *Regulatory Peptides.* 2001, 97, 31.
(17) Zagorski, M. G.; Yang, J.; Shao, H. Y.; Ma, K.; Zeng, H.; Hong, A. *Methods Enzymol.* 1999, 309, 189-204.
(18) Parihar, M. S.; Hemnani, T. *J. Clin. Neurosci.* 2004, 11, 456-467.
(19) Walsh, D. M.; Hartley, D. M.; Kusumoto, Y.; Fezoui, Y.; Condron, M. M.; Lomakin, A.; Benedek, G. B.; Selkoe, D. J.; Teplow, D. B. *J. Biol. Chem.* 1999, 274, 25945-25952.
(20) Jan, A.; Hartley, D. M.; Lashuel, H. A. *Nat. Protoc.* 2010, 5, 1186-1209.
(21) Roychaudhuri, R.; Yang, M.; Hoshi, M. M.; Teplow, D. B. *J. Biol. Chem.* 2009, 284, 4749-4753.
(22) Schmidt, M.; Sachse, C.; Richter, W.; Xu, C.; Fandrich, M.; Grigorieff, N. *Proc. Natl. Acad. Sci. U.S.A.* 2009, 106, 19813-19818.
(23) Sachse, C.; Fandrich, M.; Grigorieff, N. *Proc. Natl. Acad. Sci. U.S.A.* 2008, 105, 7462-7466.
(24) Capone, R.; Quiroz, F. G.; Prangkio, P.; Saluja, I.; Sauer, A. M.; Bautista, M. R.; Turner, R. S.; Yang, J.; Mayer, M. *Neurotox. Res.* 2009, 16, 1-13.
(25) Bitan, G.; Fradinger, E. A.; Spring, S. M.; Teplow, D. B. *Amyloid-J. Protein Fold. Disord.* 2005, 12, 88-95.
(26) Adamcik, J.; Jung, J. M.; Flakowski, J.; De Los Rios, P.; Dietler, G.; Mezzenga, R. *Nat. Nanotechnol.* 2010, 5, 423-428.
(27) Meinhardt, J.; Sachse, C.; Hortschansky, P.; Grigorieff, N.; Fandrich, M. *J. Mol. Biol.* 2009, 386, 869-877.

(28) Kremer, J. J.; Pallitto, M. M.; Sklansky, D. J.; Murphy, R. M. *Biochemistry*. 2000, 39, 10309-10318.

(29) Chou, I. H.; Benford, M.; Beier, H. T.; Cote, G. L.; Wang, M.; Jing, N.; Kameoka, J.; Good, T. A. *Nano Lett.* 2008, 8, 1729-1735.

(30) Knowles, T. P. J.; White, D. A.; Abate, A. R.; Agresti, J. J.; Cohen, S. I. A.; Sperling, R. A.; De Genst, E. J.; Dobson, C. M.; Weitz, D. A. *Proc. Natl. Acad. Sci. U.S.A.* 2011, 108, 14746-14751.

(31) Schierle, G. S. K.; van de Linde, S.; Erdelyi, M.; Esbjorner, E. K.; Klein, T.; Rees, E.; Bertoncini, C. W.; Dobson, C. M.; Sauer, M.; Kaminski, C. F. *J. Am. Chem. Soc.* 2011, 133, 12902-12905.

(32) Wang, H. Y.; Ying, Y. L.; Li, Y.; Kraatz, H. B.; Long, Y. T. *Anal. Chem.* 2011, 83, 1746-1752.

(33) Dukes, K. D.; Rodenberg, C. F.; Lammi, R. K. *Anal. Biochem.* 2008, 382, 29-34.

(34) Schauerte, J. A.; Wong, P. T.; Wisser, K. C.; Ding, H.; Steel, D. G.; Gafni, A. *Biochemistry*. 2010, 49, 3031-3039.

(35) Yusko, E. C.; Johnson, J. M.; Majd, S.; Prangkio, P.; Rollings, R. C.; Li, J.; Yang, J.; Mayer, M. *Nat. Nanotechnol.* 2011, 6, 253-260.

(36) Coulter, W. H., Means for Counting Particles Suspended in a Fluid. U.S. Pat. No. 2,656,508, Oct. 20, 1953.

(37) Dekker, C. *Nat. Nanotechnol.* 2007, 2, 209-215.

(38) Kowalczyk, S. W.; Blosser, T. R.; Dekker, C. *Trends in Biotechnology*. 2011, 29, 607-614.

(39) Howorka, S.; Siwy, Z. *Chem. Soc. Rev.* 2009, 38, 2360-2384.

(40) Majd, S.; Yusko, E. C.; Billeh, Y. N.; Macrae, M. X.; Yang, J.; Mayer, M. *Current Opinion in Biotechnology*. 2010, 21, 439-476.

(41) Yusko, E. C.; Billeh, Y. N.; Yang, J.; Mayer, M. in *Nanopores: Sensing and Fundamental Biological Interactions* (eds Iqbal, S. M.; Bashir, R.) 203-225 (Springer Publishing Co., 2011).

(42) Stanley-Wood, N. G.; Lines, R. W. *Particle Size Analysis*; The Royal Society of Chemistry: Cambridge, 1992.

(43) Branton, D.; Deamer, D. W.; Marziali, A.; Bayley, H.; Benner, S. A.; Butler, T.; Di Ventra, M.; Garaj, S.; Hibbs, A.; Huang, X. H.; Jovanovich, S. B.; Krstic, P. S.; Lindsay, S.; Ling, X. S. S.; Mastrangelo, C. H.; Meller, A.; Oliver, J. S.; Pershin, Y. V.; Ramsey, J. M.; Riehn, R.; Soni, G. V.; Tabard-Cossa, V.; Wanunu, M.; Wiggin, M.; Schloss, J. A. *Nat. Biotechnol.* 2008, 26, 1146-1153.

(44) Keyser, U. F. *J. R. Soc. Interface*. 2011, 8, 1369-1378.

(45) Ivanov, A. P.; Instuli, E.; McGilvery, C. M.; Baldwin, G.; McComb, D. W.; Albrecht, T.; Edel, J. B. *Nano Lett.* 2011, 11, 279-285.

(46) Iqbal, S. M.; Bashir, R. *Nanoelectronic-Based Detection for Biology and Medicine*; Springer-Verlag Berlin: Berlin, 2009.

(47) Grover, N. B.; Naaman, J.; Ben-sasson, S.; Doljansk, F. *Biophys. J.* 1969, 9, 1398-1414.

(48) Grover, N. B.; Naaman, J.; Ben-sasson, S.; Doljansk, F.; Nadav, E. *Biophys. J.* 1969, 9, 1415-1425.

(49) Solomentsev, Y.; Anderson, J. L. *J. Fluid Mech.* 1994, 279, 197-215.

(50) Han, A. P.; Creus, M.; Schurmann, G.; Linder, V.; Ward, T. R.; de Rooij, N. F.; Staufer, U. *Anal. Chem.* 2008, 80, 4651-4658.

(51) Sexton, L. T.; Mukaibo, H.; Katira, P.; Hess, H.; Sherrill, S. A.; Horne, L. P.; Martin, C. R. *J. Am. Chem. Soc.* 2010, 132, 6755-6763.

(52) Prangkio, P. Investigation of cytotoxicity and ion flux induced by various aggregation states of amyloid-beta peptides Ph.D. Thesis, University of Michigan, Ann Arbor, Mich., August 2011.

(53) Pedone, D.; Firnkes, M.; Rant, U. *Anal. Chem.* 2009, 81, 9689-9694.

(54) Cai, Q.; Ledden, B.; Krueger, E.; Golovchenko, J. A.; Li, J. L. *J. Appl. Phys.* 2006, 100, 024914.

(55) Li, J.; Stein, D.; McMullan, C.; Branton, D.; Aziz, M. J.; Golovchenko, J. A. *Nature*. 2001, 412, 166-169.

(56) Rousseeuw, P. J.; Kaufman, L. *Finding groups in data: an introduction to cluster analysis*; John Wiley & Sons, Inc.: New York, N.Y., 1990.

(57) Talaga, D. S.; Li, J. L. *J. Am. Chem. Soc.* 2009, 131, 9287-9297.

(58) Ito, T.; Sun, L.; Crooks, R. M. *Anal. Chem.* 2003, 75, 2399-2406.

(59) Fologea, D.; Ledden, B.; David, S. M.; Li, J. *Appl. Phys. Lett.* 2007, 91, 053901.

(60) Uram, J. D.; Ke, K.; Hunt, A. J.; Mayer, M. *Small*. 2006, 2, 967-972.

(61) Uram, J. D.; Ke, K.; Hunt, A. J.; Mayer, M. *Angew. Chem.-Int. Edit.* 2006, 45, 2281-2285.

(62) Li, J. L.; Talaga, D. S. *J. Phys.-Condes. Matter*. 2010, 22.

(63) DeBlois, R. W.; Uzgiris, E. E.; Cluxton, D. H.; Mazzone, H. M. *Anal. Biochem.* 1978, 90, 273-288.

(64) Golibersuch, D. C. *J. Appl. Phys.* 1973, 44, 2580-2584.

(65) Golibersuch, D. C. *Biophys. J.* 1973, 13, 265-280.

(66) Kozak, D.; Anderson, W.; Vogel, R.; Trau, M. *Nano Today*. 2011, 6, 531-545.

(67) Hille, B. *Ion Channels of Excitable Membranes*; Sinauer Associates, Inc.: Sunderland, 2001.

(68) Matthews, B. W. *J. Mol. Biol.* 1968, 33, 491-&.

(69) Solomentsev, Y.; Anderson, J. L. *Industrial & Engineering Chemistry Research*. 1995, 34, 3231-3238.

(70) Wanunu, M.; Morrison, W.; Rabin, Y.; Grosberg, A. Y.; Meller, A. *Nat. Nanotechnol.* 2010, 5, 160-165.

(71) Bretherton, F. P. *J. Fluid Mech.* 1962, 14, 284-304.

(72) Ai, Y.; Qian, S. *Electrophoresis*. 2011, 32, 996-1005.

(73) Berg, H. C. *Random Walks in Biology*; Princeton University Press: Princeton, N.J., 1993.

(74) Guo, M.; Gorman, P. M.; Rico, M.; Chakrabartty, A.; Laurents, D. V. *FEBS Lett.* 2005, 579, 3574-3578.

(75) An, R.; Uram, J. D.; Yusko, E. C.; Ke, K.; Mayer, M.; Hunt, A. *J. Opt. Lett.* 2008, 33, 1153-1155.

(76) Sun, L.; Crooks, R. M. *J. Am. Chem. Soc.* 2000, 122, 12340-12345.

(77) Lee, S.; Zhang, Y. H.; White, H. S.; Harrell, C. C.; Martin, C. R. *Anal. Chem.* 2004, 76, 6108-6115.

(78) Bikwemu, R.; Wolfe, A. J.; Xing, X. J.; Movileanu, L. *J. Phys.-Condes. Matter.* 2010, 22.

(79) Bacri, L.; Oukhaled, A. G.; Schiedt, B.; Patriarche, G.; Bourhis, E.; Gierak, J.; Pelta, J.; Auvray, L. *Journal of Physical Chemistry B*. 2011, 115, 2890-2898.

(80) Harper, J. D.; Lansbury, P. T. *Annu. Rev. Biochem.* 1997, 66, 385-407.

(81) Vestergaard, M.; Hamada, T.; Takagi, M. *Biotechnol. Bioeng.* 2008, 99, 753-763.

(82) Williams, T. L.; Serpell, L. C. Febs J. 2011, 278, 3905-3917.

SUPPLEMENTAL INFORMATION

| Table of Contents | |
|---|---|
| Section S1. Electrical Resistance of Electrolyte-Filled Nanopores as a Function of Bilayer Thickness | 62 |
| S1.1 Model of Electrical Resistance in Electrolyte-Filled Nanopores | 62 |
| S1.2 Dimensions of Nanopores | 63 |
| S1.3 Dimensions of Nanopores after the Formation of a Lipid Bilayer Coating | 64 |
| S1.4 Thermal Actuation of the Diameter of Bilayer-Coated Nanopores | 65 |
| Section S2. Formation of Fluid Lipid Bilayers on the Silicon Nitride Substrate and Determination of Lateral Diffusion Constants | 66 |
| Section S3. Additional Evidence for a Bilayer Coating on the Walls of the Nanopores | 68 |
| S3.1 Bilayer Coatings Prevented Physisorption of Fluorescently-Labeled Streptavidin | 68 |
| S3.2 Analysis of the Electrical Current Noise Provides Additional Evidence for the Formation of a Bilayer inside the Pore | 69 |
| Section S4. Precise Control of the Surface Chemistry | 70 |
| Section S5. Evidence for the Binding of Proteins to Lipid-Anchored Ligands in the Bilayer and for the Translocation of Lipid-Bound Proteins through Bilayer-Coated Nanopores | 71 |
| S5.1 Control Experiments with Streptavidin | 72 |
| S5.2 Excess Free Biotin in Solution Abolished Resistive Pulses due to Anti-Biotin mAb | 72 |
| S5.3 Resistive-pulses in the Absence of Biotinylated Lipids could not be Time-Resolved | 73 |
| S5.4 Comparison of Diffusion Coefficients of Lipids and Diffusion Coefficients of Proteins in the Nanopore | 75 |
| Section S6. Translocations of Non-Spherical Proteins Generate Broad Distributions of Δl | 77 |
| Section S7. Determining the Most Probable Value of $t_d$ and its Error | 80 |
| S7.1 Determining the Most Probable $t_d$ Value and its Error by Fitting Cumulative Distributions of $t_d$ Values | 80 |
| S7.2 Determining the Most Probable $t_d$ Value by Fitting Histograms of $t_d$ Values | 81 |
| Section S8. Calculating the Charge of Proteins from the Translocation Time of Lipid-Anchored Proteins | 82 |
| S8.1 Derivation of equation (3) in the main text | 82 |
| S8.2 Capillary Electrophoresis for Determining the Net Charge of Proteins | 84 |
| S8.3 Fitting Individual Distributions of $t_d$ with both z and D as Fitting Parameters | 87 |
| Section S9. Data Acquisition and Analysis of Resistive Pulses for Protein Detection | 88 |
| Section S10. Preparation of Amyloid-Beta Samples and Gel-Electrophoresis | 90 |

Figure 13A:
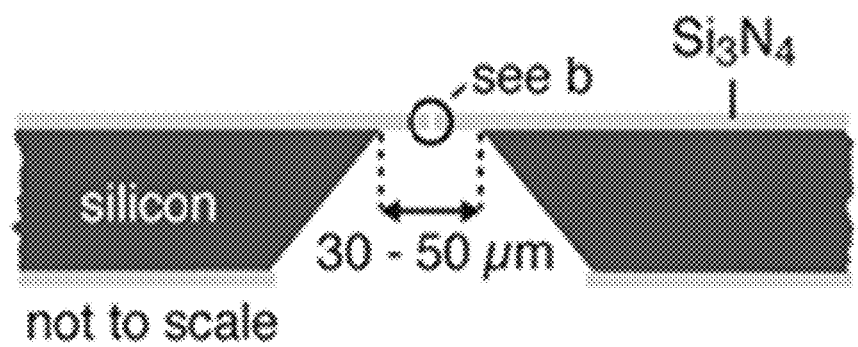

Section S1. Electrical Resistance of Electrolyte-Filled Nanopores as a Function of Bilayer Thickness
S1.1 Model of Electrical Resistance in Electrolyte-Filled Nanopores We explored the simplest possible model for the relationship between the electrical resistance and the geometry of the nanopore. Based on previous work, this model assumes that the smallest constriction of a nanopore and the resistivity of the electrolyte solution in the nanopore determine the total resistance, while the electrical resistance through the bulk electrolyte solution from the electrodes to the chip with the nanopore is negligible[1,2]. In the work presented here, the cylindrical nanopore and channel leading to the pore were the narrowest constrictions (FIG. 13).

We described the nanopore, and the channel leading to the nanopore, as cylinders, each with a radius r (m) and length l(m) that were filled with an electrolyte with resistivity, ρ (Ω×m). Due to the nanoscale diameter of the pore, the electric field lines converge from the bulk solution to the entrance of the nanopore, resulting in an additional resistive component called the access resistance, $R_A$[3]. Equation (S1) quantifies $R_A$ for one entrance to a nanopore[3].

$$R_A = \frac{\rho}{4r} \quad \text{S1}$$

Figure 13B:
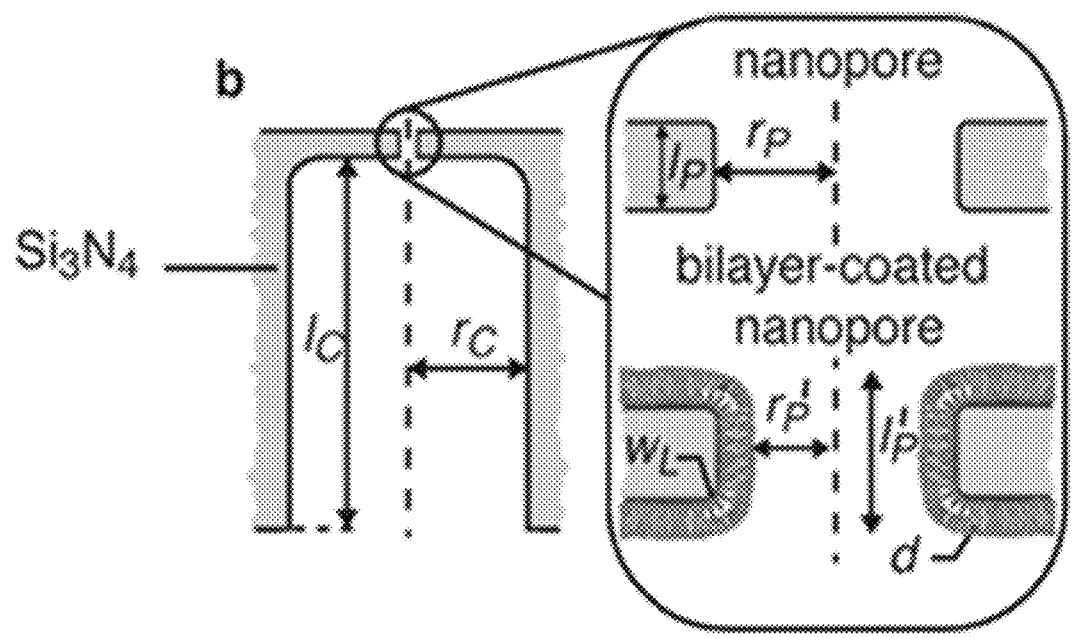

Thus, the total resistance is a function of the resistance of the nanopore, $R_P$, the access resistance at each side of the pore, $R_{AP}$, the resistance due to the channel, $R_C$, and the access resistance from the bulk solution below the chip to the channel, $R_{AC}$. We treated these resistive components as resistors in series such that equations (S2) and (S3) describe the total resistance between two electrodes on opposite sides of a nanopore:

$$R = R_P + 2R_{AP} + R_C + R_{AC}, \quad (S2)$$

$$R = \frac{\rho l_P}{\pi r_P^2} + \frac{\rho}{2r_P} + \frac{\rho l_C}{\pi r_C^2} + \frac{\rho}{4r_C}, \quad (S3)$$

where $l_P$ is the length of the nanopore, $r_P$ is the radius of the nanopore, $l_C$ is the length of the channel, and $r_C$ is the radius of the channel (FIG. 13b).
S1.2 Dimensions of Nanopores We determined the radius of the nanopores, $r_P$, and of the channels leading to these pores, $r_C$, from transmission electron microscopy images (FIG. 14). To determine the total resistance of a pore for a given electrolyte, we measured the current through a pore at various applied voltages. For these measurements, we used an electrolyte solution containing 500 mM KCl and 10 mM HEPES at pH 7.4 with a resistivity ρ of 0.1517 Ω×m (measured with a calibrated conductance meter). Finally, we determined the length of the pore, $l_P$, by solving equation (S3) with the measured value of resistance R, the values of $r_P$ and $r_C$ determined from the TEM images, and the known value for the thickness of the silicon nitride membrane (275±15 nm[4,5]). FIG. 14 shows TEM micrographs of several pores used in this work; the caption lists the dimensions of these pores and specifies for which experiments they were used.

For cases in which the cross-section through the nanopore was ellipsoid rather than circular, we calculated an "area-equivalent" radius of the pore, $<r_P>$, in such a way that the area of a perfect circle with radius $r_P$ would be equal to the area of the ellipse with x corresponding to the major axis and γ corresponding to the minor axis of the elliptical cross-section:

$$<r_P> = \sqrt{xy}. \quad (S4)$$

Similarly, we calculated an area-equivalent radius for channels, $<r_C>$, through the silicon nitride with an ellipsoid cross-section by:

$$<r_C> = \sqrt{xy}. \quad (S5)$$

Table 51 lists the dimensions of nanopores used for experiments in the main text and the corresponding experiments.

TABLE S1

Dimensions of all nanopores used for experiments and corresponding experiment and figure. All dimensions refer to the pores before bilayer coating

| Figure | Description of experiment | Pore dimensions nm | Notes |
|---|---|---|---|
| 1c | Resistance as a function of bilayer thickness | $r_p = 14$; $l_p = 12$ | TEM image in FIG. 14a |
| 1d | Resistance during a phase transition of DMPC lipids | $r_p = 13$; $l_p = 28$ | — |
| 2b, 3a, 4a | Sensing streptavidin | $<r_p> = 9.6$; $l_p = 18$ | TEM image in FIG. 14b |
| 3b, 3c, 4b, 4c, | Sensing anti-biotin Fab fragments and anti-biotin monoclonal antibodies (IgG) | $<r_p> = 16.5$; $l_p = 22$ | TEM image in FIG. 14c |
| 5 | Sensing streptavidin as a function of charge and pH | $r_p = 10.5$; $l_p = 18$ | — |
| 6 | Sensing aggregated of amyloid-beta (Aβ) peptides | $<r_p> = 48$; $l_p = 275$ | TEM image in FIG. 14d |

S1.3 Dimensions of Nanopores after the Formation of a Lipid Bilayer Coating

Figure 14A:
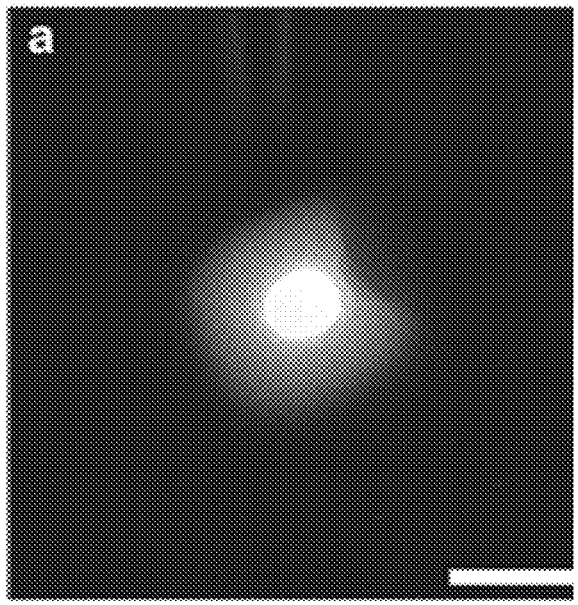
Figure 14B:
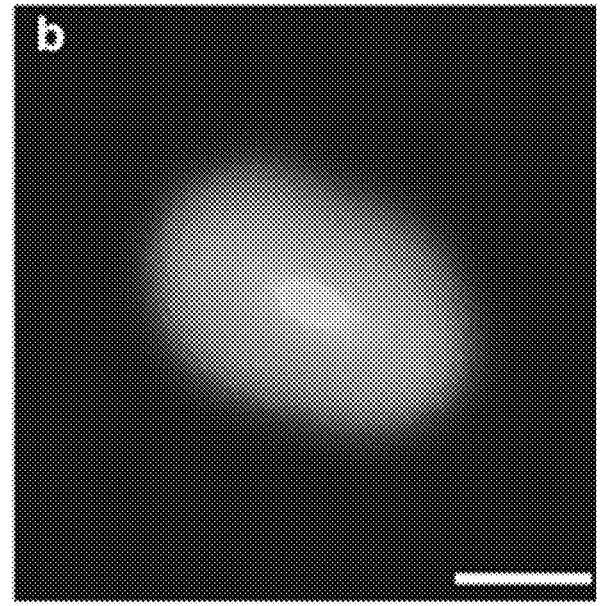
Figure 14C:
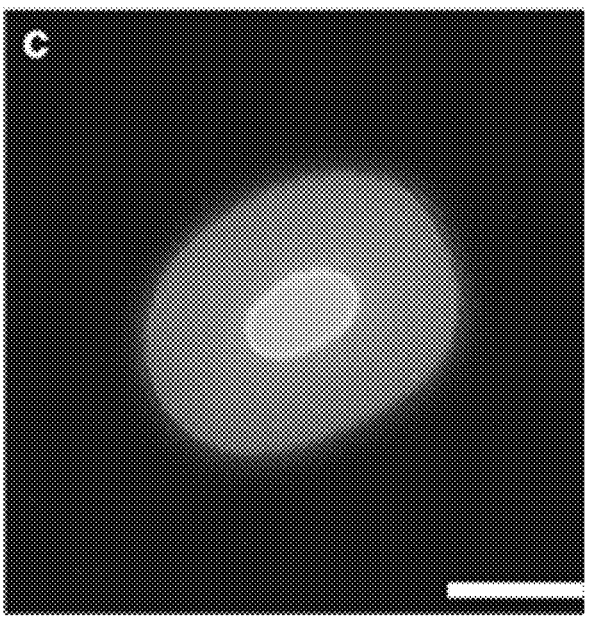
Figure 14D:
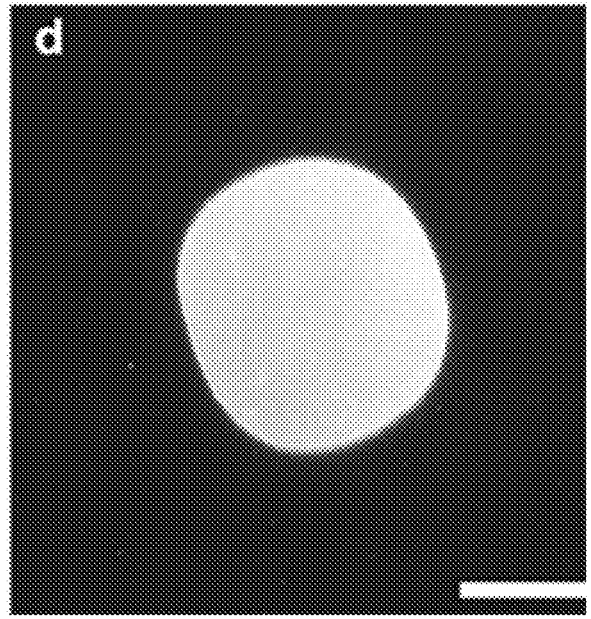

To determine the dimensions of a nanopore after forming a lipid bilayer coating, we used the cylindrical pore shown in FIG. 14a and added parameters for the thickness of the lipid bilayer, d, and for the thickness of the water layer between the silicon nitride and the lipid bilayer, $w_L$, to equation (S3) to obtain equation (S6), which is the same as equation (1) in the main text:

$$R = \frac{\rho(l_P + 2d + 2w_L)}{\pi(r_P - d - w_L)^2} + \frac{\rho}{2(r_P - d - w_L)} + \frac{\rho(l_C + 2d + 2w_L)}{\pi(r_C - d - w_L)^2} + \frac{\rho}{4(r_C - d - w_L)}. \quad (S6)$$

Equation (S6) implies that the lipid bilayer and water layer did not conduct ionic current through the nanopore. These two layers, hence, reduced the effective radius of the nanopore by $(d+w_L)$ and increased the effective length of the pore by $2\times(d+w_L)$ (FIG. 13b).

Note that we measured currents over tens of seconds in order to determine the resistance of the nanopore, R. As a result, fluctuations in the water layer or in the thickness of the supported lipid bilayer due to possible membrane undulations were averaged. We attribute the excellent agreement between the resistance of the nanopore and the thickness of the lipid bilayers (shown in FIG. 1c of the main text) to the use of the same chip and lipids with the same chemical head group (phosphatidylcholine) in these experiments. These conditions resulted in similar interactions between the bilayer, substrate, and water. In addition, we used the same cleaning procedure, same methods of preparing liposomes, and same electrolyte in each experiment.

S1.4 Thermal Actuation of the Diameter of Bilayer-Coated Nanopores

Figure 15:
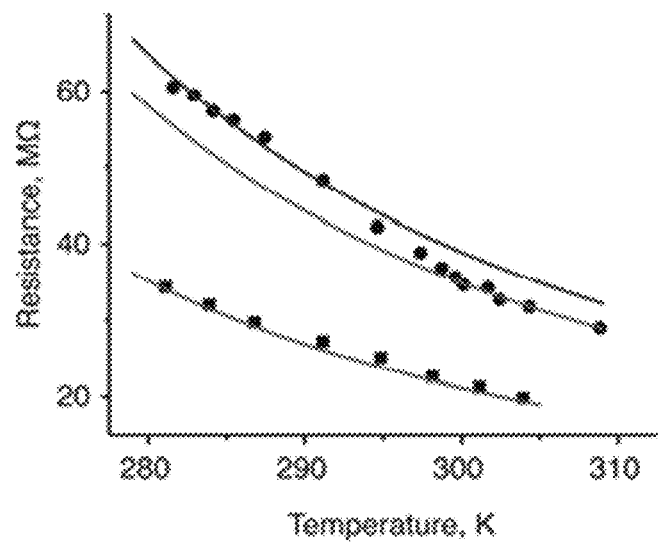

To calculate the thickness of a lipid bilayer, and hence, the effective open radius of a nanopore as a consequence of a thermal phase transition of the lipids, we described the resistivity, ρ, of the electrolyte as a function of temperature with equation (S7)[6]:

$$\rho = \frac{6\pi\eta}{CN_Ae^2\left(\frac{1}{r_+} + \frac{1}{r_-}\right)}, \quad (S7)$$

where the viscosity of water, π (Pa×s), as a function of the temperature, T (K), is given by[7]:

$$\eta = (2.414\times 10^{-5} \text{Pa}\cdot\text{s})\times 10^{\left(\frac{247.8K}{T-140K}\right)}, \quad (S8)$$

and C (mol×m$^{-3}$) is the concentration of a monovalent salt, $N_A$ is Avogadro's constant (mol$^{-1}$), e (C) is the elementary charge of an electron, $r_+$ (m) is the radius of the hydrated cation, and r (m) is the radius of the hydrated anion in the electrolyte. To validate this model, we measured the resistance of a nanopore without a bilayer coating as a function of temperature. We used an electrolyte containing 500 mM KCl and controlled the temperature of the device and electrolyte with a Peltier cooler (Warner Instruments, Hamden Conn.). FIG. 15 shows the measured resistance as a function of temperature (squares). Note that the green curve is not a fit to the data; instead it reflects the calculated resistance as a function of temperature based on equations (S3), (S7) and (S8). In equation (S8), we used values for $r_+$ of $133\times10^{-12}$ (m) for K$^+$ ions and for $r_-$ of $181\times10^{-12}$ (m) for Cl$^-$ ions[3].

To change the diameter of the nanopore, we coated the pore with a lipid bilayer of DMPC lipids (both acyl chains of DMPC are saturated and contain 14 carbons) and varied the temperature while measuring the resistance (Fig. S3, circles). We fit the data in Fig. S3 with equations (S6)-(S8) using the thickness of the bilayer, d, as the only fitting parameter. This fit in the temperature range of 300-310 K returned the red curve (N=5, R$^2$=0.97), and in the temperature range of 280-290 K, it returned the blue curve (N=5, R$^2$=0.95) (Fig. S3). To calculate the change in d as a function of the thermal phase transition of the lipid bilayer, we used Maple™ 13 to solve equations (S6)-(S8) for d, with all parameters except temperature held constant (FIG. 2c in the main text). These calculations revealed a change in bilayer thickness, Δd, between the disordered liquid crystalline phase (T>296 K) and the ordered gel phase (T<296 K) of 0.7±0.04 nm (fit in FIG. 2c in the main text). This value of Δd is similar to reported values for Δd of DMPC bilayers of 0.9-1.1 nm[8,9].

Section S2. Formation of Fluid Lipid Bilayers on the Silicon Nitride Substrate and Determination of Lateral Diffusion Constants Reimhult et al. demonstrated that liposome fusion on a silicon nitride surface forms a single supported lipid bilayer[10]. To prepare small unilamellar vesicles (SUVs), we dissolved the desired lipids in 100 μL chloroform to a lipid concentration of 10 mM. We evaporated the solvent under vacuum using a rotary evaporator to form a lipid film in a round bottom glass flask with a volume of 10 mL. We resuspended this lipid film in an aqueous solution containing 150 mM KCl and 10 mM HEPES at pH 7.5 such that the lipid concentration was 2 mM. Finally, we formed SUVs via tip sonication (Branson Sonifier 150) of the solution with a power of 3-4 W for ~10 min and stored these solutions at 4° C. for up to 4 days. We formed the supported lipid bilayer on the chips as described in the Methods Section of the main text.

Figure 16A:
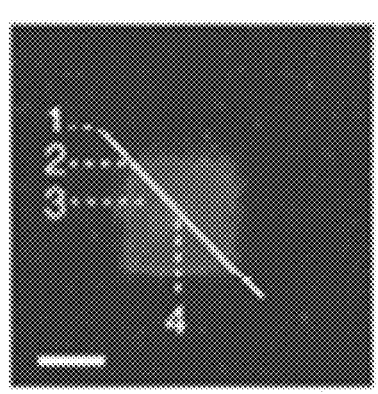
Figure 16C:
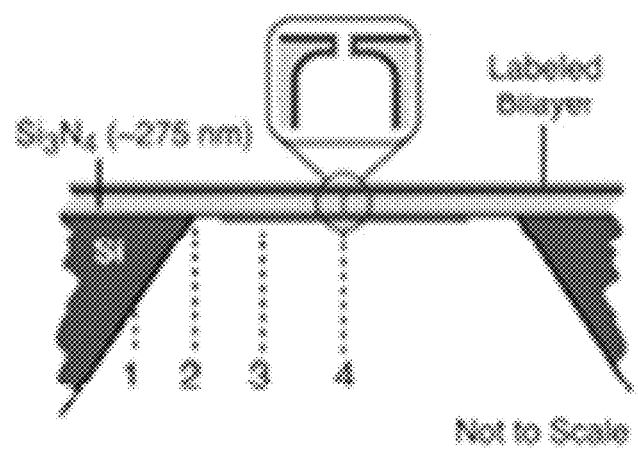
Figure 16B:
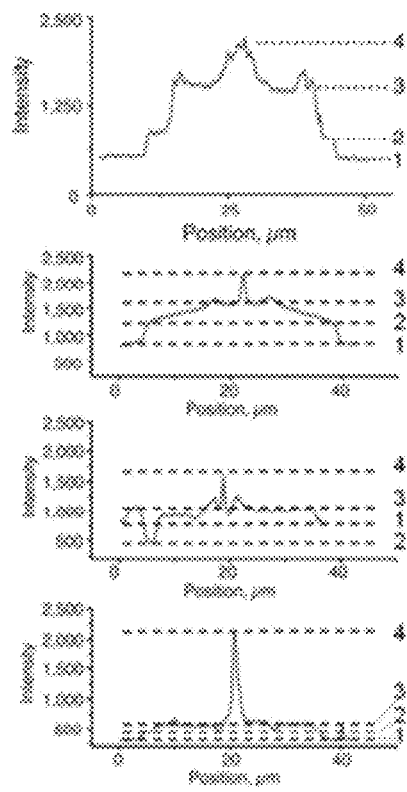

We used epifluorescence microscopy to confirm the formation of a fluid lipid bilayer for experiments with bilayer-coated nanopores. To visualize the lipid bilayer, we prepared all liposomes with 0.8 mol % of lipids labeled with the fluorophore rhodamine B (1,2-dipalmitoyl-sn-glycero-3-phosphoethanolamine-N-(lissamine rhodamine B sulfonyl)) (Rh-PE, Avanti Polar Lipids). To form the lipid bilayer, we incubated the top side of the chip in a solution containing Rh-PE labeled liposomes for 5-10 min followed by rinsing with pure water for 5-10 min. We used a Nikon E600FN upright microscope equipped with an Evolution MP (Media Cybernetics, Canada) camera and a 60× water-dipping objective (NA=1.00) to image the bilayers. FIG. 16*a* shows a fluorescent micrograph (false-colored in red) that confirmed the presence of a supported lipid bilayer on the silicon nitride substrate. The sharply defined square in the middle of the image is the free-standing silicon nitride membrane. A line scan across the silicon nitride membrane (solid white line) quantified the fluorescence intensity as a function of the position along this line (FIG. 16*a*). Interestingly, we observed four values of fluorescence intensity along this path. The lowest intensity occurred in area 1 (I=528±15); a location in which the bulk silicon chip supported the silicon nitride membrane. Moving along the line scan to an area over part of the free-standing silicon nitride membrane, indicated as area 2, we observed a slightly greater intensity (I=873±31) than in area 1. We attribute the reduced intensity in area 1 compared to area 2 to destructive interference from light reflected by the bulk silicon chip below area 1[11]. Moving further along the line scan toward the center of the free-standing, silicon nitride membrane (area 3), we observed a fluorescence intensity approximately twice the intensity (I=1,542±29) of area 2. This result indicates that area 3 contained approximately twice the amount of fluorescent Rh-PE lipids than area 2 and is consistent with a supported bilayer on both sides of the free-standing, silicon nitride membrane. Finally, area 4, in the center of the free-standing, silicon nitride membrane and at the location of the nanopore, had the greatest fluorescence intensity (I=2,222).

We attribute this high intensity to the presence of a lipid bilayer on the vertical walls of the nanopore and channel (see Fig. S1), and hence, to an increased number of Rh-PE lipids in the optical path. Fig. S4*e* shows three additional fluorescence micrographs with a spot of high intensity in the center of the free standing, silicon nitride membrane at the precise location of the nanopores. The width of these spots at $1/e^2$ of their maximum intensity, $w_{(1/e^2)}$ ranged from 0.8 μm to 1.8 μm. These values are 2-5 times larger than the theoretical diffraction-limited spot size of 0.33 μm that we calculated for this objective with equation (9)[12]:

$$w_{(1/e^2)} = \frac{2\lambda}{n\pi NA}, \quad (9)$$

where, $\lambda$, is the wavelength of light (here ~700 nm), n is the index of refraction of the medium (here 1.33), and NA is the numerical aperture of the objective (here 1.00). The larger than expected values for the size of the diffraction-limited spot could be due to reflection or refraction occurring at the interface between the aqueous solution and the transparent silicon nitride structure of the nanopore.

Figure 16E:
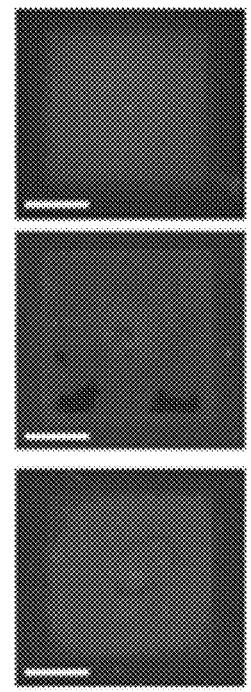

Furthermore, equation (9) predicts the size of the smallest spot that can be obtained theoretically given all of the optics were perfect—real microscopes typically cannot reach this theoretical limit. Regardless of deviations from the theoretically expected spot size, the images in FIG. 16*e* confirm the observations in FIG. 16*a, b* with regard to the fluorescence intensity from bilayers on the chips. These results, in combination with the well-defined shrinkage of the pore diameter by bilayer coatings of various lipids (FIG. 1*c*) and the results from FIGS. 3 and 4, suggest that a supported lipid bilayer formed on the silicon nitride, on the inner walls of the nanopore and channel, and on the underside of the free-standing, silicon nitride membrane.

Figure 17A:
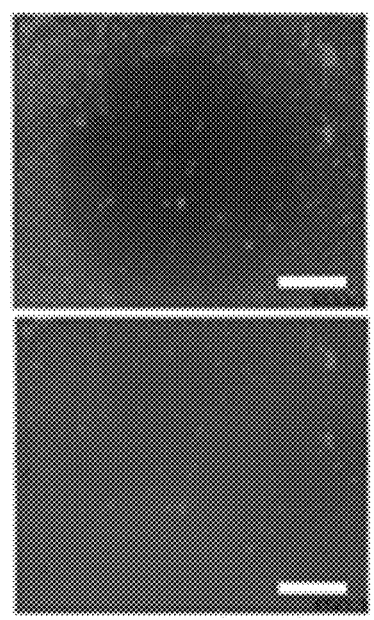

To confirm the fluidity of the supported lipid bilayers and to determine lateral diffusion constants of the lipids, we preformed fluorescence recovery after photobleaching (FRAP) experiments (FIGS. 16*a* and *b*) on the bilayer at a location outside, but near, the free-standing, silicon nitride membrane (i.e., in area 1 of FIG. 16*a*)[13]. We analyzed these images by calculating the difference between the mean fluorescence intensity of the photobleached spot and a second spot on the same bilayer that was not photobleached. We normalized to the maximum difference between these two intensities and determined the diffusion coefficients by the equation, $D_L$ (nm$^2$×μs$^{-1}$)=0.224×ω$^2$ (nm)$^2$/t$_{1/2}$ (μs), where ω is the radius of the bleached spot and t$_{1/2}$ is the half time of the fluorescence recoveryl[4,15]. We obtained the value of t$_{1/2}$ from an exponential curve fit through the data (FIG. 17*b*). On the chip used in FIG. 17 and shown in FIG. 14*b*, the diffusion coefficient for bilayers containing POPC lipids was 1.13±0.13 nm$^2$×μs$^{-1}$ and for bilayers containing DΔPPC lipids it was 1.56±0.16 nm$^2$×μs$^{-1}$. These values are close to reported values of diffusion coefficients of supported bilayers, which range from 2 nm$^2$×μs$^{-1}$ to 5 nm$^2$×μs$^{-1}$ and are typically obtained on glass or SiO$_2$ surfaces instead of Si$_3$N$_4$ surfaces[16,17].

Figure 18B:
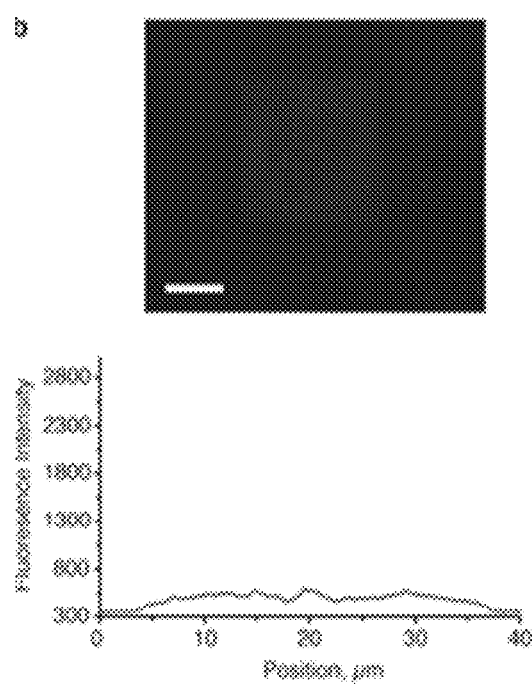
Figure 19A:
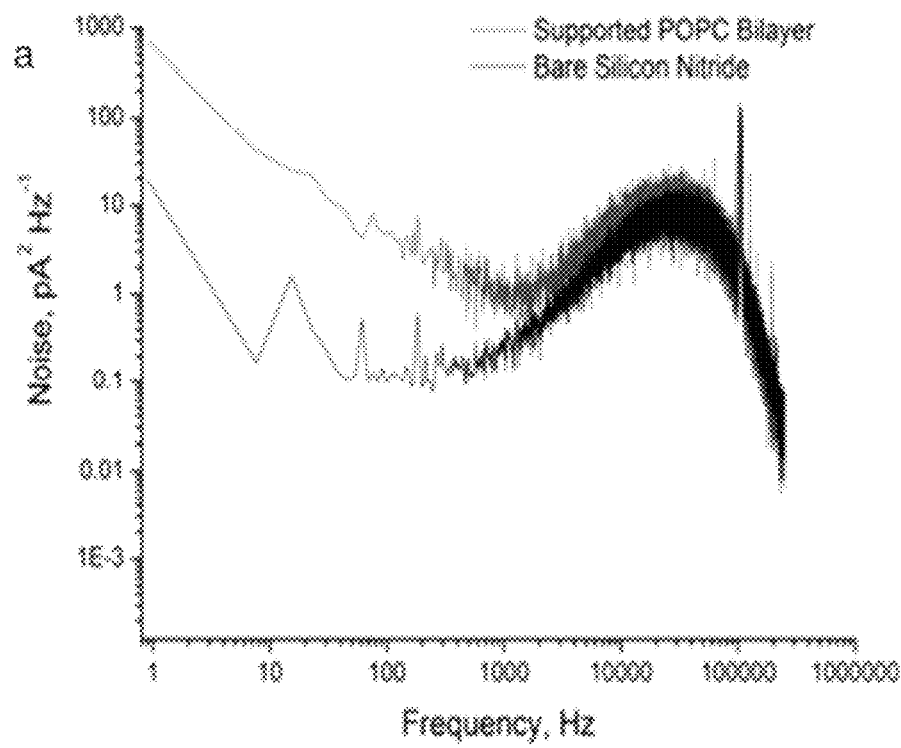
Figure 19B:
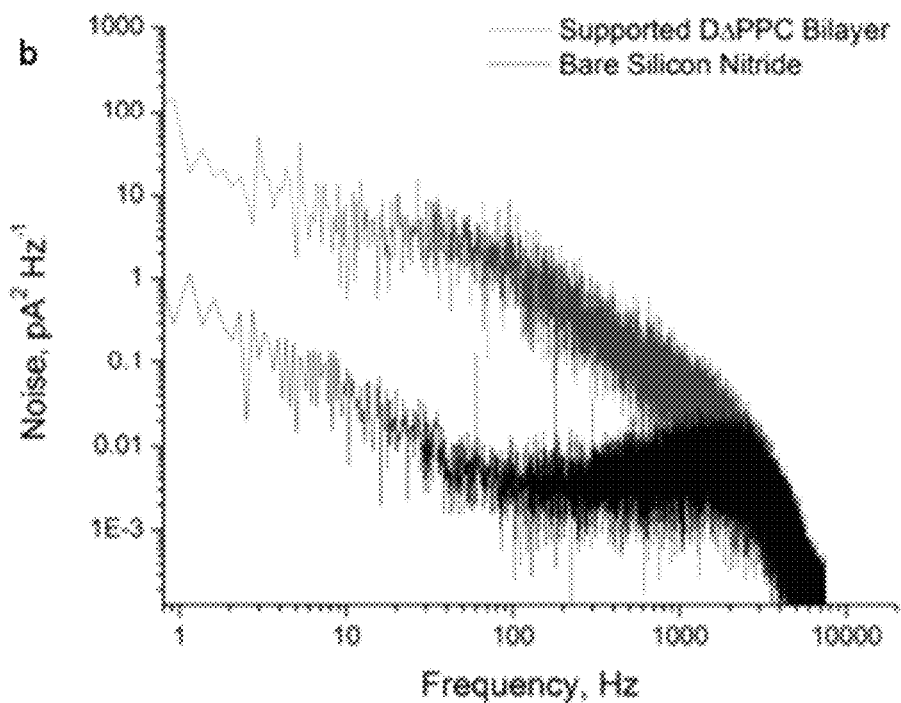
Figure 19C:
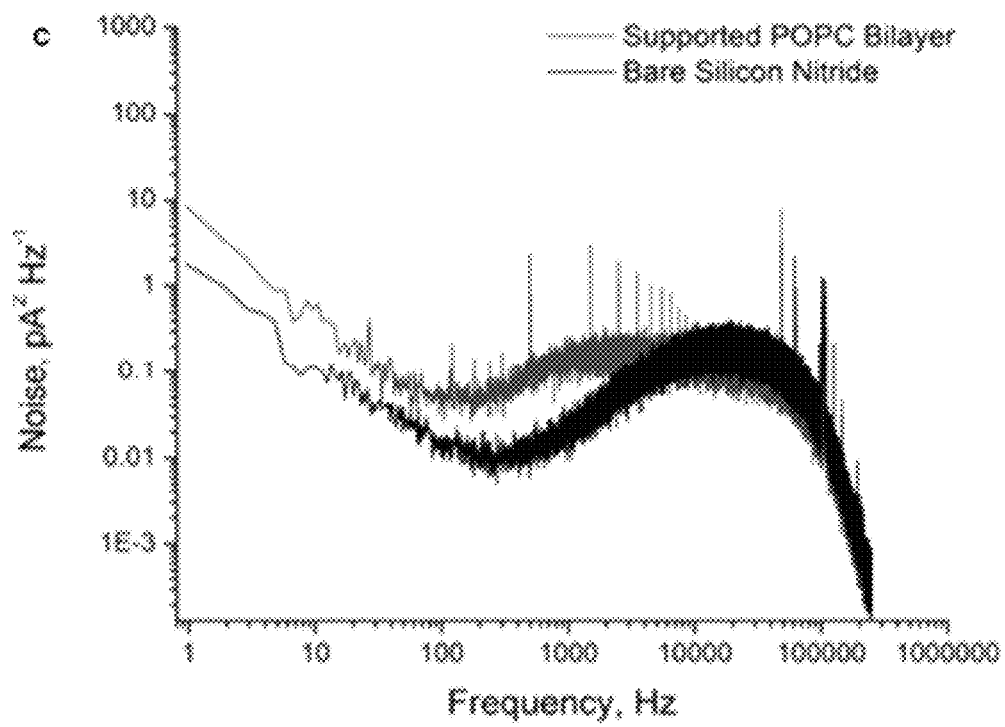
Figure 19D:
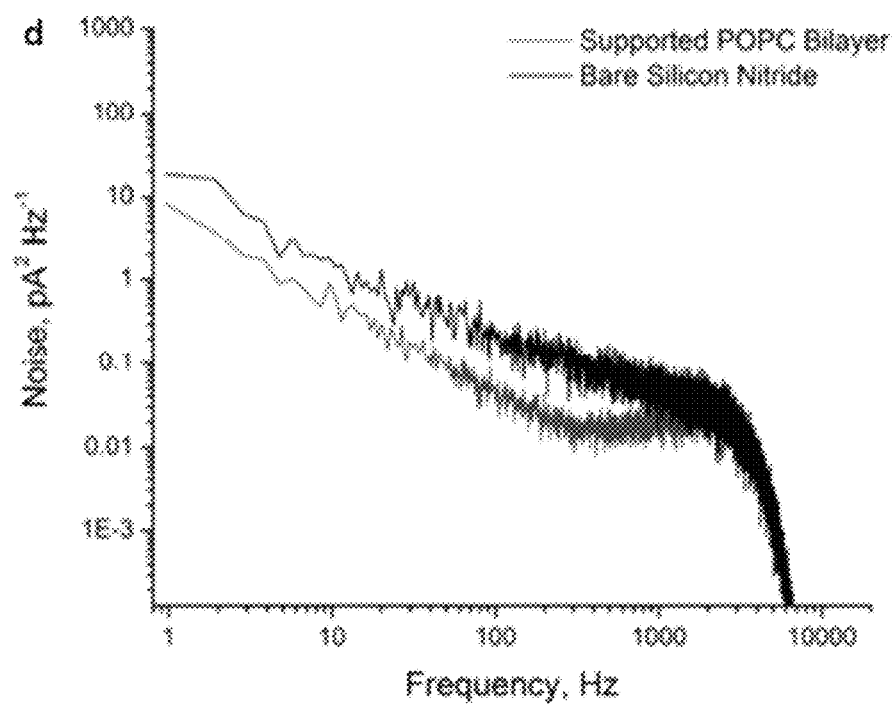

Section S3. Additional Evidence for a Bilayer Coating on the Walls of the Nanopores S3.1 Bilayer Coatings Prevented Physisorption of Fluorescently-Labeled Streptavidin To provide additional evidence that a supported lipid bilayer formed on the walls inside the nanopores, we incubated a chip containing a nanopore with rhodamine-labeled streptavidin (SA-TRITC). We incubated the same piranha-cleaned chip with SA-TRITC in one experiment after forming a supported lipid bilayer on the chip (and in the pore) and in the other experiment before forming the bilayer. FIG. 18*a* shows that in the absence of a bilayer coating, SA-TRITC physisorbed to the silicon nitride surface including in the center of the silicon nitride window where a bright spot of fluorescence indicates that SA-TRITC also physisorbed onto the walls inside the uncoated nanopore. Similar to the line scans shown in FIG. 16, the width of the diffusion limited high intensity spot in FIG. 18*a* was 0.9 μm. In contrast, FIG. 18*b* shows that the same chip, after being cleaned and subsequently coated with a lipid bilayer, did not physisorb a detectable amount of rhodamine-labeled streptavidin. Additionally, at the center of the silicon nitride window and the location of the nanopore, we did not detect an increase in the intensity of fluorescence. This result suggests that the vertical walls inside the nanopore were also coated with a lipid bilayer that prevented the physisorption of SA-TRITC.

S3.2 Analysis of the Electrical Current Noise Provides Additional Evidence for the Formation of a Bilayer Inside the Pore Since supported lipid bilayers are fluid sheets, lipid molecules within the bilayer are in dynamic motion. In addition, the water layer between the lipid bilayer and the silicon nitride substrate fluctuates around an average value. We hypothesized that the resulting bilayer undulations may influence the electrical noise in current recordings. FIG. 19, b compare the power spectra of the noise as a function of frequency for two chips with nanopores before and after generating a supported lipid bilayer. As expected, when the pore was coated with a fluid lipid bilayer, the noise increased at low frequencies (<2 kHz) compared to the uncoated pore. Since this increased noise was likely due to dynamic motions consistent with a supported lipid bilayer inside the nanopores, it provides additional evidence for the formation of a lipid bilayer on the walls inside the nanopores. To test this hypothesis, we obtained power spectra of the noise with a chip that contained a very small nanopore with area-equivalent diameter of 9 nm. The diameter of this nanopore was too small for a supported lipid bilayer to form on the interior walls of the pore. In this case, spreading of fluorescently-labeled liposomes on the top side of the chip coated only this top side while no increased fluorescence could be detected at the location of the pore and no doubled fluorescence intensity could be detected from creeping of fluorescent bilayers through the pore to the other side of the silicon nitride window. FIG. 19, d shows that in this case, the electrical noise in the system remained relatively unchanged compared to the nanopores with a diameter large enough to accommodate a bilayer coating inside the pore. In both experiments, we confirmed by FRAP experiments that the bilayer near the pore was fluid. Together these results provide additional evidence for the formation of a fluid lipid bilayer on the walls inside the nanopore.

Section S4. Precise Control of the Surface Chemistry

Figure 20:
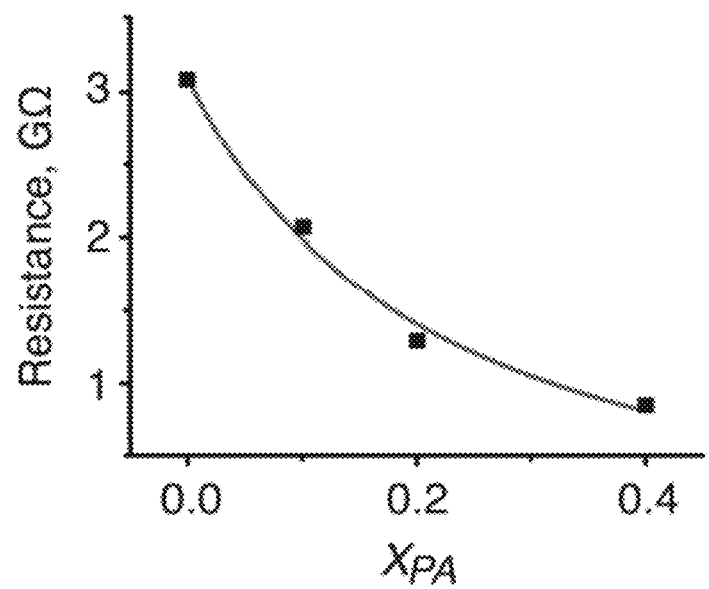

The surface chemistry of bilayer-coated nanopores can be precisely controlled by the nature of the polar head groups of the lipids used in the bilayer coating. To demonstrate this capability, we formed several liposome preparations from POPC lipids that contained different mole fractions of 1,2-dioleoyl-sn-glycero-3-phosphate (DOPA), a lipid with a negatively charged head group. After vesicle fusion of these liposomes onto S1/S13N4 chips with a nanopore to generate the bilayer coating, we measured the electrical resistance through the nanopore. Since under conditions of low ionic strength, positively charged ions accumulate near the surface of a negatively charged bilayer, we expected to observe a decrease in the resistance of the pore with increasing mole fractions of DOPA.[18] FIG. 20 confirms that the resistance of the bilayer coated nanopore decreased with increasing mole fractions of DOPA lipids inside the nanopore walls.

Figure 21:
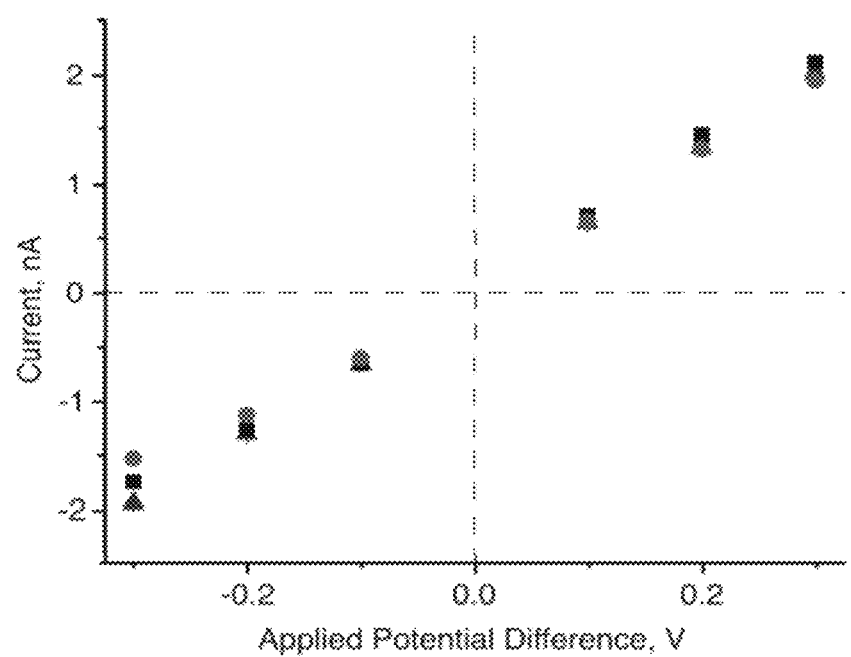

To demonstrate that this decrease in the resistance was a nanoscopic effect, as predicted by the Gouy-Chapman theory, we compared the resistance of a conical pore (tip diameter 500 nm) whose walls were coated by an electrically neutral bilayer (~99 mol % POPC) to the resistance of the same pore with a negatively charged bilayer coating (~40 mol % DOPA and ~59 mol % POPC). Using the same electrolyte as in FIG. 20, the resistance of this large pore remained independent of the presence of a neutral or negatively charged bilayer coating (FIG. 21). This result confirms that the observations in FIG. 20 were due to nanoscopic phenomena in pores with diameters that are significantly smaller than 500 nm; it also provides additional evidence for the formation of a negatively charged bilayer on the walls inside the nanopore.

Section S5. Evidence for the Binding of Proteins to Lipid-Anchored Ligands in the Bilayer and for the Translocation of Lipid-Bound Proteins Through Bilayer-Coated Nanopores We used the amplitude of resistive pulses, $\Delta I$, to distinguish the translocation of streptavidin (SA), monoclonal anti-biotin antibody (mAb), and anti-biotin Fab fragments (Fab) through nanopores. These pores were coated with a bilayer that contained biotinylated lipids (biotin-PE) at the specified mole fractions. To confirm that resistive pulses were due to proteins that were bound to biotin-PE, we performed several control experiments that entailed: 1) replacing the electrolyte in the top compartment with a solution that did not contain SA to investigate if the frequency of events would be reduced (as expected for unbound SA) or remain the same (as expected for lipid-anchored SA); 2) presenting an excess of soluble biotin in solution in the presence of mAb on a chip that contained a bilayer-coated nanopore with biotin-PE lipids; and 3) detecting the translocation of SA, mAb, and Fab with bilayer-coated nanopores that did not contain biotin-PE lipids. We describe these experiments in detail in the following paragraphs, but briefly, when the protein could bind to biotin-PE in the bilayer coating, we observed 20-500 times more frequent translocation events than under conditions in which the protein could not bind to biotin-PE. Furthermore, we observed significantly prolonged translocation times when proteins could bind to biotin-PE; these increased $t_d$ values permitted time-resolved measurements of $\Delta I$ (and therefore quantitative estimation of protein volume). Finally, the viscosity of the bilayer coating influenced the translocation time of proteins passing through the nanopore only when proteins could bind to biotin-PE. We show that the diffusion coefficients of the proteins in the nanopore under these conditions were similar to the diffusion coefficients of the lipids in the bilayer coating, and we present a simple model for predicting the translocation times for proteins through a nanopore. We conclude from these results that bilayer-coated nanopores with biotin-PE lipids detected specifically proteins that bound to these lipid anchored biotin groups. Moreover, resistive pulses were due to the translocation of protein-(biotin-PE) complexes through the nanopore because biotin-PE remained mobile within the fluid bilayer coating of the nanopore. The unique ability of bilayer-coated nanopores to exploit the viscosity of a fluid bilayer coating in order to reduce the translocation speed of proteins made it possible to determine the volume of proteins accurately and, consequently, to distinguish anti-biotin Fab fragments from anti-biotin mAbs.

S5.1 Control Experiments with Streptavidin

Figure 22A:
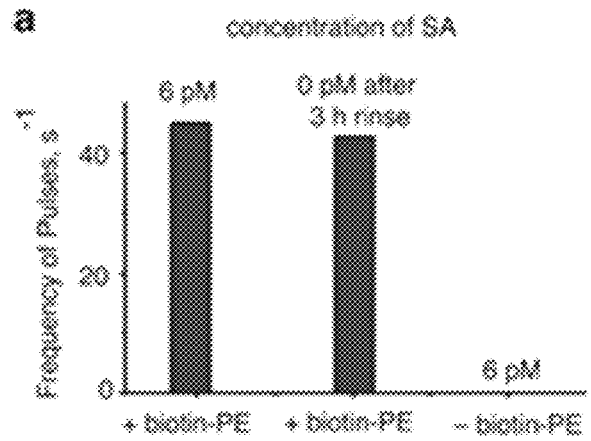

We hypothesized that SA would remain bound to biotin-PE for extended periods of time due to the very slow off-rate of the SA to biotin interaction ($k_{off}$~$10^{-6}$ s$^{-1}$)[19]. Consequently, after washing the liquid compartments to remove unbound SA from solution, we expected to observe a continuation of frequent resistive pulses with a nanopore coated with a bilayer containing biotin-PE. To start this experiment, we generated a bilayer-coated nanopore that contained 0.15 mol % biotin-PE lipids. After adding 6 pM SA to the electrolyte on top of the fluidic setup, we applied a voltage of −0.1 V and observed resistive pulses at a frequency of ~45 s⁻¹ (FIG. 22a). Consistent with resistive pulses due to proteins with a net negative charge, we observed a 28-fold decrease in the frequency of resistive pulses after changing the polarity of the applied voltage to +0.1 V (frequency of ~1.6 s⁻¹). After rinsing the fluidic channels periodically for 3 h, we again applied a voltage of −0.1 V and observed resistive pulses at a frequency similar to the frequency before washing (41 s⁻¹ versus 45 s⁻¹, FIG. 22a). When we repeated this experiment with a bilayer-coated nanopore that did not contain biotin-PE lipids, we observed almost no resistive pulses (frequency of ~0.09 s⁻¹, FIG. 2b and FIG. 22a). Together these results confirm that the observed resistive pulses were due to translocation of SA bound to lipid-anchored biotin through the nanopore while biotin-PE remained mobile within the fluid bilayer coating.

Figure 22B:
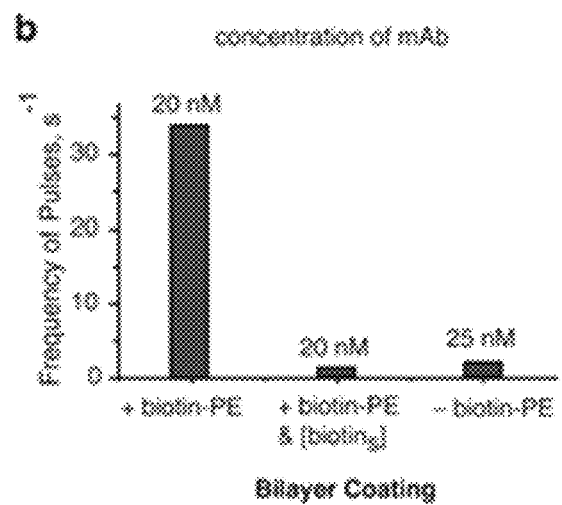
Figure 23A:
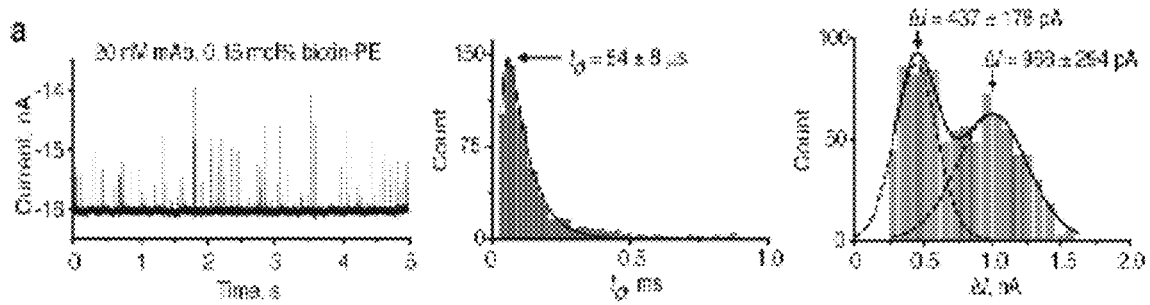
Figure 23B:
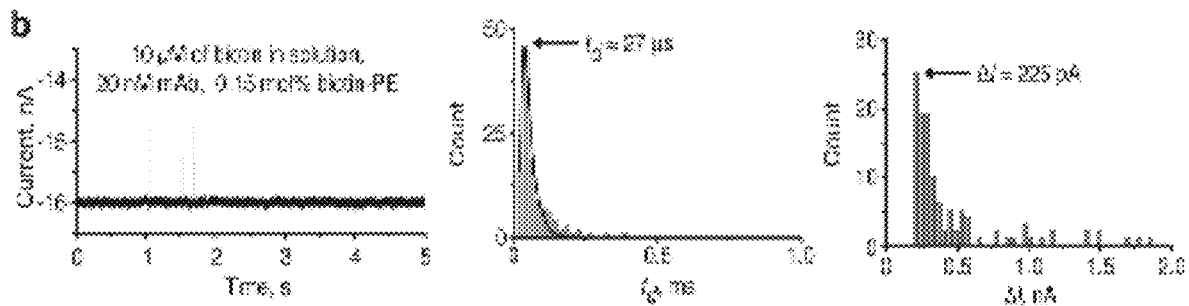

S5.2 Excess Free Biotin in Solution Abolished Resistive Pulses Due to Anti-Biotin Ab To provide additional evidence for the specificity of detection of proteins that were targeted by lipid-anchored biotin (i.e. streptavidin, anti-biotin mAb, or anti-biotin Fab fragments) with bilayer-coated nanopores, we performed a control experiment by adding a high concentration of soluble biotin (10 μM) to an ongoing experiment with a bilayer-coated nanopore that contained biotin-PE. We hypothesized that the excess biotin in solution would compete for biotin binding sites on these proteins, and consequently, the frequency of resistive pulses after the addition of biotin would decrease. To start this experiment, we coated a nanopore with a bilayer that contained biotin-PE lipids. After adding 20 nM anti-biotin mAb to the solution in the top fluid compartment, we observed resistive pulses at a frequency of 34 s⁻¹ (FIGS. 22b and 23a). After adding 10 μM soluble biotin to the solution, we observed significantly fewer resistive pulses (frequency of 1.3 s⁻¹) demonstrating that approximately 96% of the resistive pulses in Fig. S11a were due to mAb that was bound to biotin-PE (FIG. 22b and FIG. 23b). This result indicates that the detection of the proteins (i.e. streptavidin, mAb, or Fab) required binding of the proteins to biotin-PE lipids and that the proteins moved through the nanopore while bound to mobile biotin-PE lipids in the fluid, lipid bilayer coating.

We hypothesized that in this control experiment, the excess biotin in solution would occupy the majority of the binding sites of anti-biotin mAb and would therefore prevent the mAb from binding to biotin-PE lipids. Consequently, we expected the translocation of mAb through the nanopore to occur faster than before the addition of excess biotin (i.e. when the mAb moved through the nanopore as a lipid-anchored mAb-biotin-PE complex). The histograms of $t_d$ and ΔI values in FIGS. 23a and 23b confirmed this expectation by illustrating that the most frequently observed translocation time decreased from 54±8 μs to ~27 μs after adding excess biotin in solution. This result indicates that the viscosity of the bilayer coating reduced the translocation speed (i.e. increased the value of $t_d$) of mAbs that were bound to biotin-PE lipids in the bilayer by at least a factor of two compared to translocation of unbound mAbs. Furthermore, in contrast to the translocation times for mAb that was bound to biotin-PE ($t_d$=54±8 μs), translocation times for unbound mAb ($t_d$ 27 μs) were shorter than the bandwidth of the recording setup (Supplementary Section S9), and consequently, the values for ΔI were attenuated because they were not time resolved (FIG. 23b).

Figure 22C:
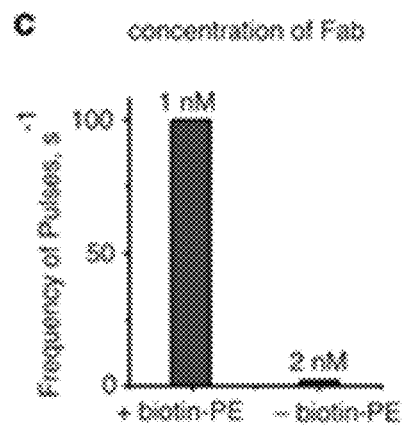

S5.3 Resistive-Pulses in the Absence of Biotinylated Lipids could not be Time-Resolved To confirm that time-resolved detection of streptavidin, anti-biotin mAb, and anti-biotin Fab fragments with bilayer-coated nanopores required biotin-PE lipids in the bilayer coating, we generated bilayer-coated nanopores that did not contain biotin-PE and added SA, mAb, or Fab fragments. We analyzed the current recordings to determine the frequency of resistive pulses, the values of $t_d$, and the magnitudes of ΔI. FIG. 22 shows that bilayers without biotin-PE resulted in resistive pulses at 20-500-fold lower frequencies than bilayers with biotin-PE (see also FIGS. 23 and 24a for original current traces). These results suggest that biotin-PE in the supported lipid bilayer concentrated the proteins from solution onto the surface of the fluid bilayer via protein-ligand binding and that these surface bound proteins translocated through the pores at a higher frequency than proteins from the bulk electrolyte. Furthermore, it suggests that the resistive pulses we observed with bilayer-coated nanopores containing biotin-PE were mostly (>90%) due to the movement of protein-biotin-PE complexes within the bilayer coating of the nanopore.

Figure 23C:
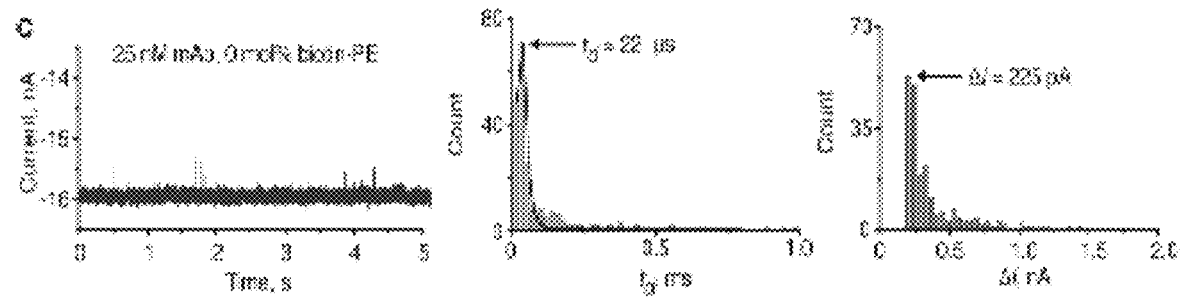
Figure 24A:
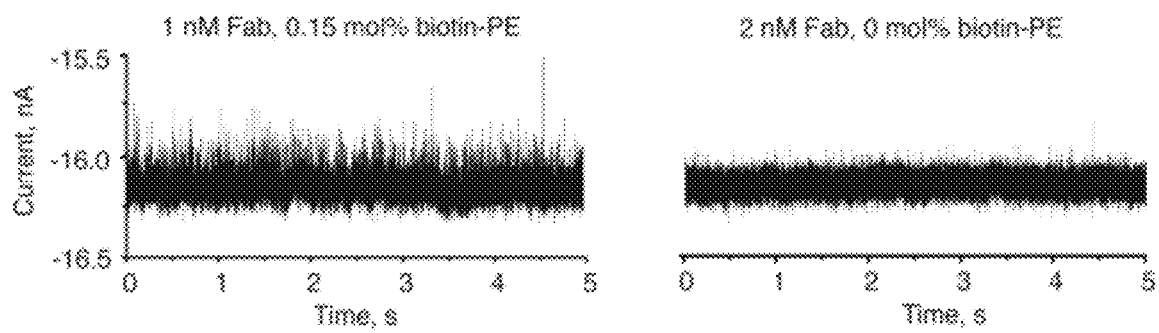

In the absence of biotin-PE in the bilayer coating, we expected the translocation of proteins through the pore to occur faster than in pores that were coated with a bilayer containing biotin-PE since in the latter case the viscosity of the bilayer can reduce the translocation speed of proteins bound to lipids. As a result, we expected to observe reduced values of $t_d$ and attenuated values of ΔI compared when biotin-PE was not used in the bilayer coating. Due to the non-Gaussian distributions of $t_d$, we compared the values of translocation times, $t_d$, that we observed most frequently in each distribution of $t_d$ values (i.e. the most probable value). For instance, the translocation of anti-biotin mAb through a bilayer-coated pore without biotin-PE lipids was significantly faster ($t_d$ 22 μs) than the translocation through the same pore with a bilayer coating that contained biotin-PE ($t_d$=54±8 μs) (FIG. 23). The translocation time of 22 μs was below the lower limit of accurate quantification of $t_d$, and consequently, we obtained reduced values of ΔI when the bilayer coating did not contain biotin-PE (Fig. S11c). Thus, we did not resolve a complete distribution of ΔI, and we observed few values of ΔI (<10%) larger than 500 pA (FIG. 23c).

Figure 24B:
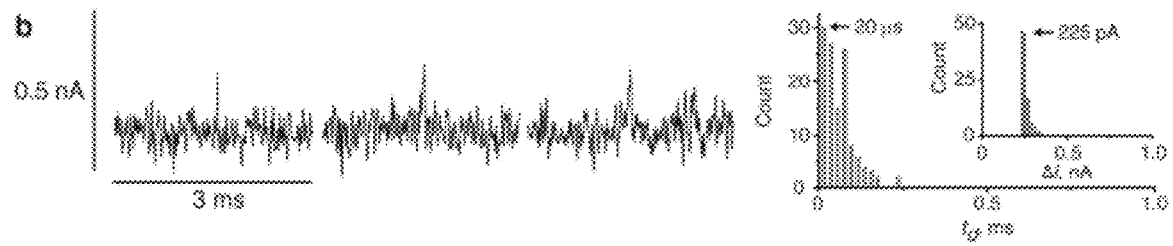
Figure 24C:
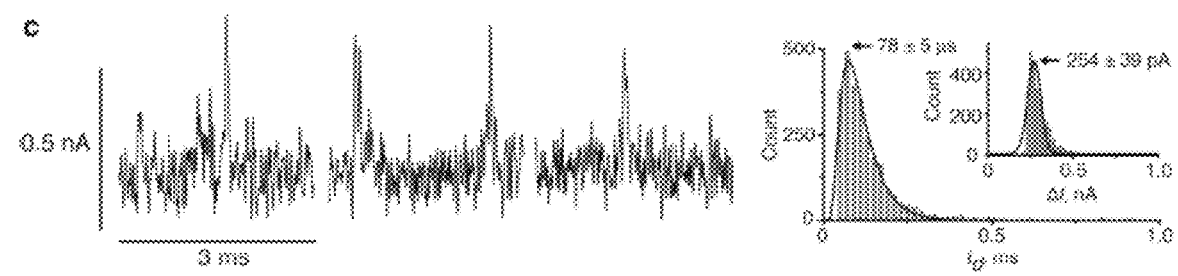

We obtained similar results from analyzing resistive pulses due to the translocation of Fab fragments; the translocation of Fab fragments through a bilayer-coated pore without biotin-PE lipids was faster ($t_d$ 20 μs, FIG. 24b) than the translocation through the same pore with a bilayer coating that contained biotin-PE ($t_d$=78±5 μs, FIG. 24c). Again, we observed reduced values of ΔI and an incomplete distribution of ΔI (FIG. 24b) when the bilayer did not contain biotin-PE lipids. In contrast, when the bilayer coating contained biotin-PE, the increased translocation time of Fab through the nanopore resulted in a fully resolved distribution of ΔI with an average value of 254±39 pA (FIG. 24c). Using equation (2) from the main text, we estimated a volume of 172±31 nm³ for the Fab fragments; the expected volume from literature is ~140 nm³ [20]. Together, these results provide evidence that the local viscosity of the bilayer coating in combination with lipids presenting ligands provides an effective novel strategy for increasing the translocation time of specific proteins that are bound to lipid-anchored ligands.

To further increase the translocation time of Fab fragments, we generated a bilayer coated nanopore that contained biotin-PE and cholesterol. The presence of cholesterol in a lipid bilayer can increase its viscosity significantly[13]. We hypothesized that the translocation of Fab through this bilayer-coated nanopore would be slower than with a bilayer coating of purely POPC and biotin-PE. For these experiments, we formed the bilayer coating from liposomes prepared with 0.15 mol % biotin-PE, 0.8 mol % Rh-PE, 49.5 mol % POPC, and 49.5 mol % cholesterol. As expected, in the presence of anti-biotin Fab fragments, we observed translocation times ($t_d$=175±4 μs, FIG. 24$d$) approximately twice as long as with bilayers that did not contain cholesterol ($t_d$=78±5 μs, FIG. 24$c$). We obtained a value of ΔI of 275±29 pA, which corresponds to a volume of 178±19 nm$^3$ (Fig. S12$d$). Given that the reported volume of Fab fragments are ~140 nm$^3$, these results suggest, once again, that a bilayer coating with increased viscosity made it possible to resolve translocation events of individual proteins completely in time and that this capability makes it possible to determine the volume of Fab fragments accurately.

S5.4 Comparison of Diffusion Coefficients of Lipids and Diffusion Coefficients of Proteins in the Nanopore.

We expected the diffusion coefficient of the lipids in the bilayer, $D_L$, and the diffusion coefficient of the proteins in the nanopore, $D_P$, to have similar values since diffusion coefficients of lipid-anchored proteins are determined by the diffusion coefficients of their lipid anchor in a lipid bilayer[21-23]. Table 2 in main text compares $D_L$ to $D_P$ using equation 3 from the main text to calculate $D_P$ based on measured $t_d$ values. For this comparison, we used the most probable value of $t_d$ and the known charge of the protein to calculate the diffusion coefficient, $D_P$. Recent work by Talaga and Li enables an additional method for determination of $D_P$ by fitting individual distributions of $t_d$ values to a biased diffusion first passage time model developed by these authors[24]. Here, we compare diffusion coefficients obtained by these fits to the entire distribution of $t_d$ values with diffusion coefficients of the lipids, $D_L$, determined by FRAP.

The model developed by Talaga and Li is shown in equation (S10); this function describes the distribution of values of $t_d$ that result from the translocation of charged proteins through a nanopore in the presence of an electric field[24]:

$$P(t_d) = \frac{(vt_d + l_P) \times e^{\frac{-(l_P - vt_d)^2}{4Dt_d}}}{t_d \times \sqrt{4Dt_d\pi}}. \quad (S10)$$

Here, v (m×s$^{-1}$) is the electrophoretic drift velocity and D (m$^2$×s$^{-1}$) is the diffusion coefficient of the protein within the nanopore. Briefly, this equation assumes that a particle (or protein) moves in one dimension with an electrophoretic mobility u$_e$ (m$^2$×V$^{-1}$×s$^{-1}$) and that its motion is driven by a linear electric field, s (V×m$^{-1}$), which results in the electrophoretic drift velocity, v=ε×u$_e$. It also assumes that the protein moves from a starting point (signified in time by the beginning of the resistive pulse) to an infinite sink that is a distance l$_p$ away (signified in time by the end of the resistive pulse). Further details on the derivation can be found in the article by Talaga and Li[24-26].

Since the values of $t_d$ result from the translocation of a protein, a best-fit analysis of the distribution of $t_d$ values from protein translocation experiments with equation (S10) provides the diffusion coefficient of the proteins in the nanopore (i.e. D=$D_P$). As shown in Table S2, the values of $D_P$ were similar to values of $D_L$ when the bilayer coating contained biotin-PE lipids and when the proteins were able to bind to the lipid-anchored biotin moiety. Typically we observed values of $D_P$ that were within ±31% of the value for $D_L$, with a maximum deviation of +117%. When the bilayer coating did not contain biotin-PE or when the protein did not bind to the lipid-anchored biotin moiety (i.e., in the presence of excess biotin free in solution), this analysis determined values of $D_P$ that were at least 3-fold greater than the value of $D_L$. Although these $D_P$ values were only semi-quantitative due to the incomplete distribution of such short $t_d$ values, they indicate that the diffusion coefficient of unbound proteins through the nanopore did not depend on the viscosity of the bilayer coating. Moreover, the agreement between $D_P$ of proteins bound to a lipid-anchored ligand and $D_L$ supports the hypothesis that the fluidity of the bilayer coating determined the translocation time of lipid-anchored proteins through the nanopores. These results provide further evidence for the formation of a fluid, bilayer coating within the nanopore.

TABLE S2

Comparison of diffusion coefficients of lipid-anchored proteins within the nanopore, $D_P$, determined by equation (S10) with diffusion coefficients of lipids in the bilayer coating, $D_L$.

| Protein | Lipid Bilayer | $D_L{}^a$ (nm$^2$ μs$^{-1}$) | $D_P{}^b$ (nm$^2$ μs$^{-1}$) | $\Delta_D{}^c$ % |
|---|---|---|---|---|
| SA$^d$ | POPC + biotin-PE | 1.13 ± 0.13 | 1.4 ± 0.1 | +24 |
| SA$^d$ | DAPPC + biotin-PE | 1.56 ± 0.16 | 1.7 ± 0.1 | +9 |
| mAb$^e$ | POPC + biotin-PE | 1.29 ± 0.13 | 2.8 ± 0.2 | +117 |
| Fab$^e$ | POPC + biotin-PE | 1.27 ± 0.13 | 1.7 ± 0.1 | +31 |
| Fab$^e$ | 50 mol % POPC and 50 mol % cholesterol + biotin-PE | 0.31 ± 0.03 | 0.6 ± 0.05 | +100 |

$^a$$D_L$ was calculated based from the FRAP method as described in Supplementary Section S2.
$^b$Diffusion coefficient of the protein, $D_P$, in the nanopore as obtained from the best-fit of the cumulative distributions of $t_d$ values (see section S7.1) to equation (S13), which is the integrated form of equation (S10).
$^c$Delta ($\Delta_D$) was calculated by: 100 × ($D_P$ − $D_L$)/$D_L$
$^d$Experiments were performed with the nanopore shown in Supplementary FIG. S2b.
$^e$Experiments were performed with the nanopore shown in Supplementary FIG. S2c.

Section S6. Translocations of Non-Spherical Proteins Generate Broad Distributions of ΔI FIG. 4 in the main text shows that the distributions of ΔI values for streptavidin and Fab fragments were significantly narrower than the distribution for the IgG antibodies. On first sight, the two maxima in FIG. 4$c$ might be attributed to a contamination by other proteins in the solution of anti-biotin IgG antibodies. Closer inspection of the data reveals, however, that these contaminants would have to bind specifically to biotin, since neither of the two peaks in FIG. 4$c$ were present in control experiments with pores that were coated with the same bilayer but without biotinylated lipids (FIG. 23). The broad distribution in FIG. 4$c$ was, however, not caused by a contamination of anti-biotin Fab fragments in the solution of anti-biotin IgG antibodies because Fab fragments would result in a narrow peak in the distribution with a most frequently observed ΔI value ~0.25 nA (FIG. 4$b$), while the two maxima in FIG. 4$c$ were located at ΔI values of ~0.4 nA and ~1.0 nA. Therefore, we attribute the broad distribution of ΔI values in FIG. 4$b$ primarily to the complex molecular shape of IgG antibodies (γ≠1.5) compared to the approximately spherical shape (γ≈1.5) of streptavidin and Fab fragments. In order to provide an estimate for the shape factor of IgG antibodies, we considered their thickness of 2.4 nm and volume of 347 nm$^3$ [27] and approximated their shape by an oblate spheroid (i.e., by a lentil-shaped particle) with a volume equal to IgG antibodies and a pole-to-pole diameter, A, equal to the thickness of IgG antibodies (A=2.4 nm). This approximation yields an oblate spheroid with an equatorial diameter, B, of 16.6 nm. The shape factor, γ, of an oblate spheroid with diameters A and B depends on the orientation in which it translocates through the pore[2]. FIG. 25 illustrates this orientation dependence of γ graphically. For the two extremes of translocation with the pole-to-pole axis of the spheroid oriented perpendicular to the length axis of the pore, Grover et al predicted γ=1.1 and for translocation with the equatorial axis oriented perpendicular to the length axis of the pore, they predicted γ≈5.0². The two dashed red lines in FIG. 4c in the main text indicate ΔI values for these two values of γ as predicted theoretically by equation (2) in the main text for oblate spheroids with diameters A and B and a volume of 347 nm³. Since these two values of ΔI represent the extremes with regard to the orientation during translocation, the majority of the experimentally observed values of ΔI would be expected to lie between these extremes. FIG. 4c confirms this expectation and provides the first experimental support that resistive pulse analysis may yield information about the shape (based on the distribution of ΔI values) and orientation (based on the individual ΔI value) of proteins with known volumes during their translocation, as predicted theoretically by Grover et al in 1969[2]. Previously, Mathe et al. observed orientation dependent translocation in nanopore-based DNA experiments through α-hemolysin pores' and Akeson et al. observed large variations in ΔI for the same population of nucleic acids due to various physical processes[29].

As mentioned before, the two orientations in FIG. 25 represent the two extremes, realistically a lipid-anchored protein will probably not move through the pore in only one orientation but in many orientations as it rotates around its lipid anchor. To examine the possibility of rotation, we estimated the time it would take an antibody to rotate 2π radians (360°) around one axis based on equations (S11) and (S12)[31]:

$$<\theta^2> = 2D_r t, \quad (11)$$

where θ (rad) is the degrees of rotation, $D_r$ (rad² s⁻¹) is the rotational diffusion coefficient and, t is (s) the time. Using the effective radius of an IgG antibody determined from diffusion coefficient measurements[32] ($R_{eff}$=5.5 nm), we estimated $D_r$ for an IgG antibody from equation S12[31]:

$$D_r = \frac{k_B T}{f_r} = \frac{k_B T}{8\pi\eta R^3}, \quad (12)$$

where $k_B$ (J K⁻¹) is the Boltzmann constant, T (K) is the temperature, and $f_r$ is the rotational friction coefficient. Based on these calculations, which were derived for spherical particles, we estimated that the average time for an antibody to complete one rotation would be ~18 μs. We also calculated the time for one rotation of a disk with a similar size to an IgG antibody and obtained a value of ~26 μs[31]. These times are approximately one third of the translocation time of the antibody through the nanopore (FIG. 3c in the main text). Consequently, the rotation of the antibody while inside the nanopore may result in a value of γ that is the average of the two extreme values, which would yield <γ>=3.1. This hypothesis is consistent with the peak at ΔI~1.0 nA in the distribution of ΔI values for the mAb as indicated by the red dashed line in FIG. 4c of the main text. The additional peak in FIG. 4c at ΔI~0.4 nA might be due to factors that are not considered in equations (S11) and (S12). For instance, the rotational diffusion coefficient predicted by equation (S12) assumes a spherical protein that is free in solution. Here, the protein was not spherical and attached to a surface inside the confined volume of a nanopore. All three effects likely increase the average time it takes for the antibody to complete a full rotation. This increased time in combination with steric effects inside the confined volume of the nanopore may result in a preferred orientation of the antibody in the nanopore (i.e. FIG. 25a) that is maintained throughout most of the translocation time. Another possibility is the alignment of the antibody within the electric field due to a dipole moment within the molecule. Due to the shape of the IgG antibody, such an alignment would be most likely along its length axis and result in the orientation of the mAb shown in FIG. 25a and a peak in the ΔI distributions at a value of γ of approximately 1.1. In addition, hydrodynamic effects as a result of rotation may drive antibodies towards the wall of the pore, which would also favor the orientation shown in FIG. 25a.

Figure 26A:
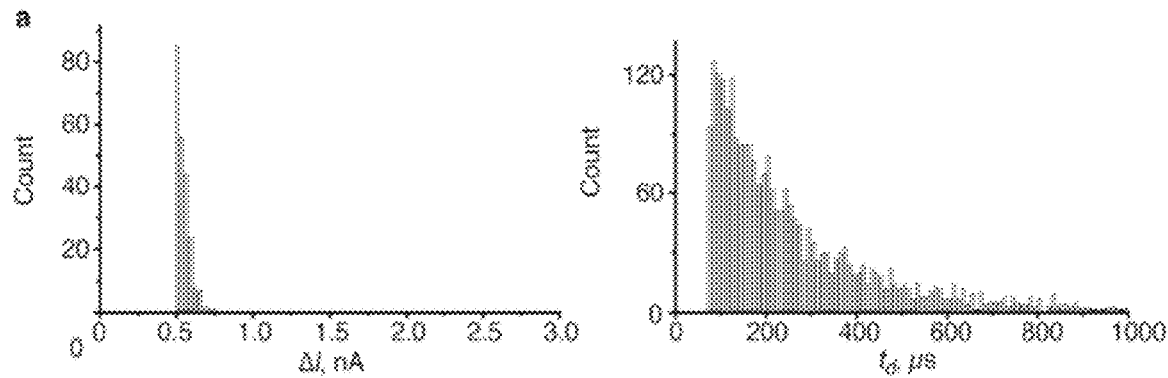
Figure 26B:
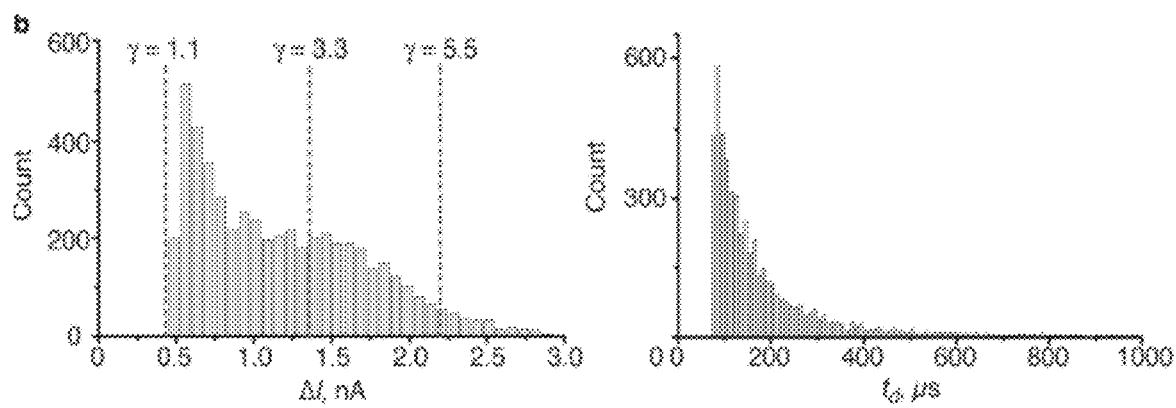

To provide a second example of a broad distribution of ΔI obtained with a non-spherical protein, we employed a bilayer coated nanopore containing biotin-PE lipids in the bilayer coating, streptavidin, and a biotinylated IgG antibody (anti-catalase antibody, AbCam®). In this experiment, streptavidin bound to the biotin-PE lipids and translocated through the pore resulting in resistive pulses with small values of ΔI (FIG. 26a). Subsequent addition of the biotinylated-IgG antibody and the translocation of the lipid-anchored, streptavidin-IgG complex returned large values of ΔI and an even broader distribution of values for ΔI (FIG. 26b) than those from the translocation of the anti-biotin mAb (FIG. 23a and FIG. 4c from the main text). We expected this result since the shape of the streptavidin-IgG complex deviates even further from a spherical shape than an IgG antibody. We approximated the streptavidin-IgG complex as an oblate spheroid with a pole-to-pole diameter of 2.4 nm and an equatorial diameter of 18.8 nm; the shape factor of such an oblate spheroid would be γ=1.1 when the pole-to-pole axis is oriented perpendicular to the length axis of the pore and γ=5.5 when the equatorial axis is oriented perpendicular to the length axis of the pore. FIG. 26b shows that approximately 95% of the values for ΔI were between the expected ΔI for the protein complex given the molecular volume of the complex and these values for γ.

Section S7. Determining the Most Probable Value of $t_d$ and its Error

S7.1 Determining the Most Probable $t_d$ Value and its Error by Fitting Cumulative Distributions of $t_d$ Values In the main text, we report the most frequently observed value of $t_d$, located at the absolute maximum of each distribution of measured $t_d$ values. We quantified these most probable values of $t_d$ by generating cumulative distributions of measured $t_d$ values. To generate cumulative distributions we summed the relative number of observations that occurred at or below a specified $t_d$ value (x-axis), thereby effectively integrating the data[33]. Cumulative distributions are advantageous compared to the histograms shown in FIG. 3 in the main text because they are generated from all $t_d$ values without binning the data[33]. To fit these cumulative distributions we integrated equation (S10) to obtain equation (S13) and fit the cumulative $t_d$ data to this equation:

$$A(t_d) = \frac{1}{2}\text{erfc}\left[\frac{(l_p - vt_d)}{2\sqrt{Dt_d}}\right] \quad (S13)$$

Figure 27:
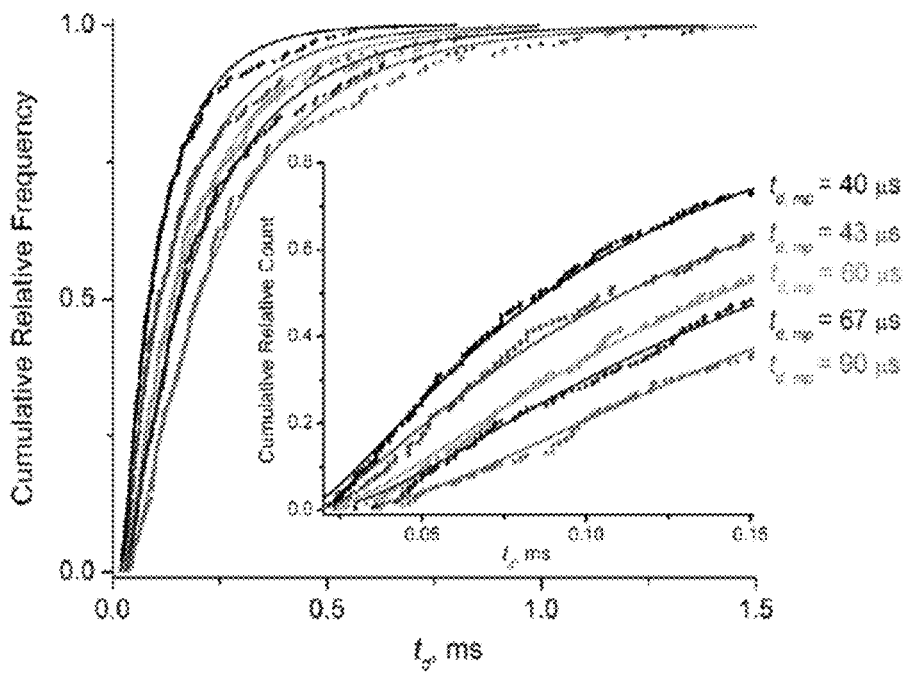

To determine the most probable $t_d$ value for a given distribution, we set the second derivative of the fitted equation (S13) equal to 0 and solved for $t_d$. The most probable $t_d$ values determined from the cumulative distributions shown in FIG. 27 are plotted in FIG. 28 in Section S8.1. To report an error for each most probable $t_d$ value, we varied the fitting parameters, including the length of the nanopore ($l_P$) and the diffusion coefficient ($D_L$), by their measured error and reported the maximum deviation in $t_d$. The maximum error in $l_P$, as estimated from the data in FIG. 1C in main text, was ±1 nm while the maximum error of diffusion coefficients of lipids in supported lipid bilayers as determined by FRAP was ±10%[13]. This method resulted in most probable $t_d$ values with errors that ranged from ±2% to ±23% of the most probable value of $t_d$.

FIG. 27 shows that cumulative distributions whose most probable $t_d$ values differed by only 3 μs could be resolved (see the black and red data) if the experiment was performed on the same chip, with the same bilayer, and under the same experimental conditions. This high resolution is likely to result from errors in $l_P$ that are expected to have nearly the same systematic error for all recordings and would therefore be expected to be significantly smaller than ±1 nm. The errors of up to ±23% of the most probable $t_d$ values reported above refer to separate experiments, possibly with different chips, when the chips were cleaned and fresh bilayers were formed between each experiment.

S7.2 Determining the Most Probable $t_d$ Value by Fitting Histograms of $t_d$ Values In the experiments for determining the most probable values of $t_d$ for the translocation of streptavidin at different pH values of the electrolyte (FIG. 5 in the main text), we found that a few of the cumulative $t_d$ distributions could not be fit very well with equation (S13). Therefore we determined the most probable value of $t_d$ from these distributions with fits of equation (S14) to $t_d$ histograms, which returned the location of the maximum in the histograms:

$$y = y_o + Ae^{\left(-e^{-\frac{(x-x_c)}{w}} - \frac{(x-x_c)}{w} + 1\right)}. \tag{S14}$$

Figure 28A:
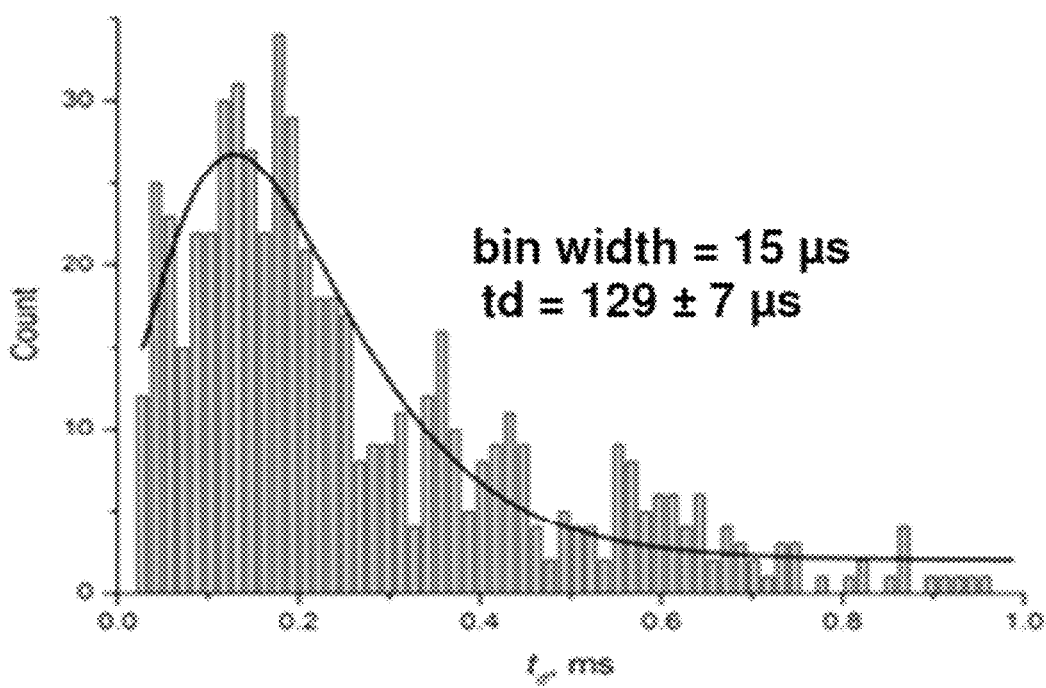
Figure 28B:
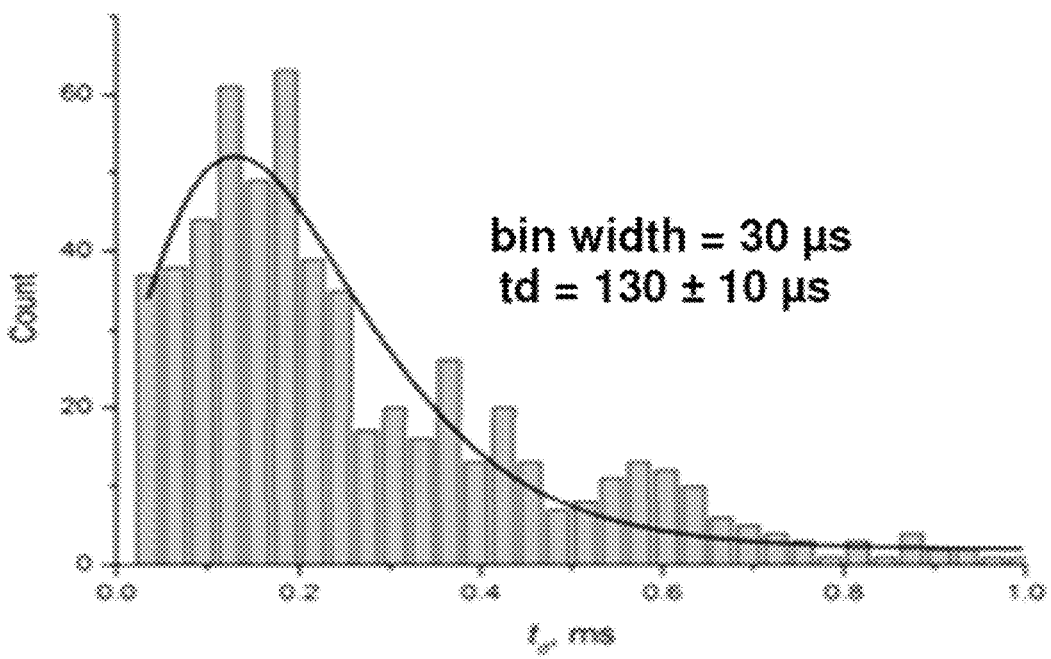
Figure 28C:
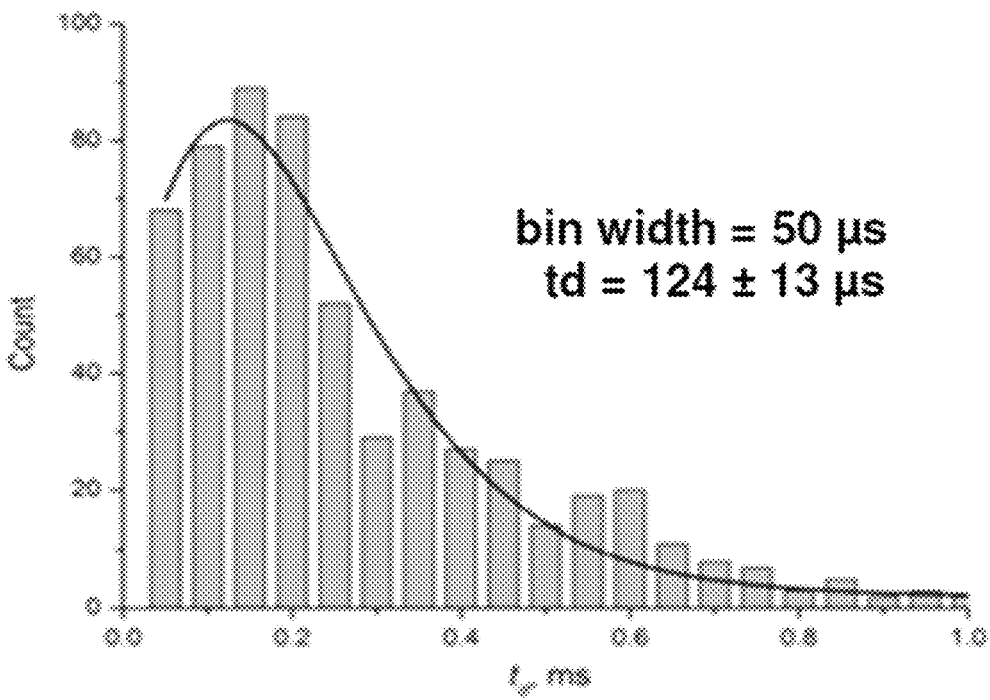

In this equation $y_o$ is the baseline, A is the amplitude of the peak, $x_c$ is the x-value at the center of the peak (i.e. the most probable value of $t_d$), and w is the width of the distributions. Based on the results of this fit to the distributions of $t_d$, we reported the value of $x_c$ and its error from the fit as the most probable $t_d$ value with its associated error. To determine if the value of $x_c$ was sensitive to the size of the bins in the $t_d$ histograms, we generated histograms with different bin-widths from $t_d$ values obtained streptavidin. In all cases the first bin began at 25 μs since this value represents the lower limit for accurate detection and quantification of $t_d$ (See Supplementary Section S9). FIG. 28 shows the resulting histograms from bin widths of 15 μs, 30 μs, and 50 μs. In all three cases, the most probable $t_d$ values (i.e. the value of $x_c$) determined by the best curve fits of equation (S14) to $t_d$ histograms were within error of each other (with maximum deviations of 6 μs), demonstrating that this method of fitting distributions of $t_d$ values for determining the most probable $t_d$ value was not sensitive to the binning method in a range of bin widths from 15 to 50·s.

One of the advantages of using the most probable value of $t_d$ for quantitative analysis compared to using, for instance, the average value of $t_d$, is that the absolute maximum in each distribution can be determined with high accuracy and small errors (smaller than 23% of the most probable value of $t_d$) from fits to histograms of $t_d$. This approach of determining the location of the absolute maximum is not sensitive to the possible presence of small sub-peaks in $t_d$ histograms such as those present in some $t_d$ distributions in FIG. 3 in the main text.

Section S8. Calculating the Charge of Proteins from the Translocation Time of Lipid-Anchored Proteins S8.1 Derivation of Equation (3) in the Main Text Based on recent work by Sexton et al, we developed the simplest possible model that yields a relationship between $t_d$, the lateral diffusion coefficient of the lipids in the bilayer coating, $D_L$, and the net charge of a protein, $|z| \times e$, where z (unitless) is the net valency of the charge on the protein and e (C) is the elementary charge of an electron[34].

This model assumed that the only driving force, f (N), acting on a charged, translocating protein is exerted by the electric field that drops inside the pore; it also assumed that inside of cylindrical nanopores the voltage $V_P$ (V) drops linearly along the length of the pore, $l_p$ (m):

$$f = |z|e\frac{V_p}{l_p}. \tag{S15}$$

Note that $V_p$ refers only to the part of the total applied voltage, $V_a$, that drops inside the pore, and it can be calculated by $V_p = V_a \times R_p/R_{total}$ (see Supplementary Equations (S3) and (S6)). Based on these assumptions, the charged protein experiences a constant force opposed by a viscous drag inside the pore, leading to a constant net electrophoretic drift velocity, v (m s$^{-1}$):

$$v = \frac{l_p}{t_d} = \frac{f}{\zeta}, \tag{S16}$$

where $\zeta$ (kg s$^{-1}$) represents the viscous friction coefficient. Assuming that, for lipid-anchored proteins, $\zeta$ is dominated by the lipid anchor in the bilayer[21-23], it can be expressed by the Stokes-Einstein relationship:

$$\zeta = \frac{k_B T}{D_L}, \tag{S17}$$

where $k_B$ (J K$^{-1}$) is the Boltzmann constant, T (K) is temperature, and $D_L$ (m$^2$ s$^{-1}$) represents the lateral diffusion coefficient of lipids in the bilayer. Combining equations (S15)-(S17) yields the desired functional relationship between $t_d$, the diffusion coefficients of the lipids in the bilayer coating, and the net charge of a translocating protein:

$$t_d = \frac{l_p^2 k_B T}{|z|eV_p D_L}. \tag{S18}$$

This equation is the same as equation (3) in the main text.

In order to validate this model and the resulting equation (S18), we analyzed translocation events of streptavidin molecules through bilayer-coated pores with biotin-PE lipids while employing electrolyte solutions of various pH to vary the value of |z| according to Sivasankar et al[35]. FIG. 5 of the main text shows that equation (S18) accurately predicted $t_d$ as a function of |z| and could be used to determine parameters such as $D_L$, $l_P$, or |z|.

Figure 29:
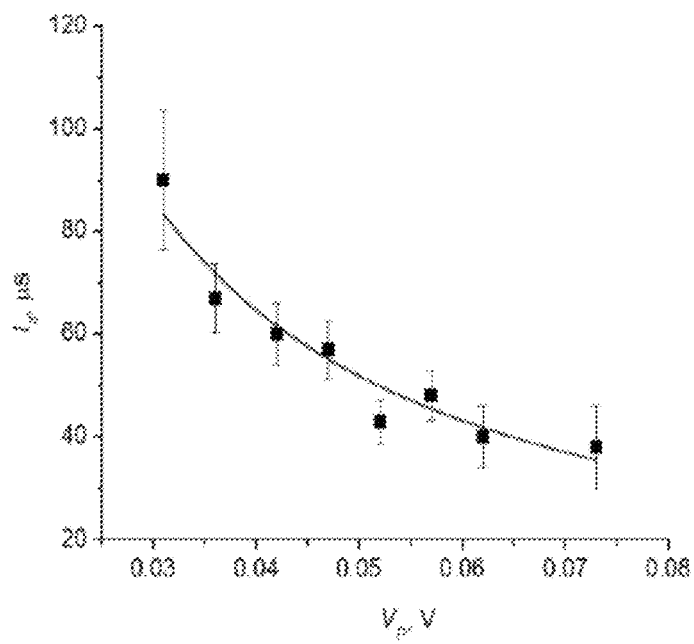

We further validated equation (S18), which is equation (3) in the main text, by determining the most probable $t_d$ values from translocation events of the IgG antibody as a function of the voltage drop inside the nanopore, $V_p$. FIG. 29 illustrates that $t_d$ was indeed inversely proportional to $V_p$ as predicted by equation (S18). Moreover, fitting equation (S18) to the data in FIG. 29 revealed a net charge of the antibody of $z=-4.2\pm0.5$ with z as the only fitting parameter. This value compares well to the value of $z=-3.6\pm2.3$ determined by capillary electrophoresis (Section S8.2). We also used equation S18 to calculate a net average charge for the Fab fragment of $-5.4\pm0.6$ based on the most frequently observed $t_d$ value in FIG. 3b of the main text. This value is comparable to the charge that we determined by capillary electrophoresis ($z=-4.3\pm0.4$) or by fits to the distributions of $t_d$ ($z=-2.9\pm0.6$) (see Sections S8.2 and 8.3). As a result, we reported a range for the values of z in the main text.

Note that in all experiments, we assumed that the pH value inside the nanopore was the same as the pH value in the bulk electrolyte solution. Since we carried out all protein translocation experiments in nanopores that were coated with electrically neutral phosphatidylcholine bilayers and since the KCl concentration of the electrolyte in these experiments was 2.0 M, we did not expect significant differences between the pH value inside the pore and the value in the bulk solution.

S8.2 Capillary Electrophoresis for Determining the Net Charge of Proteins

Figure 30A:
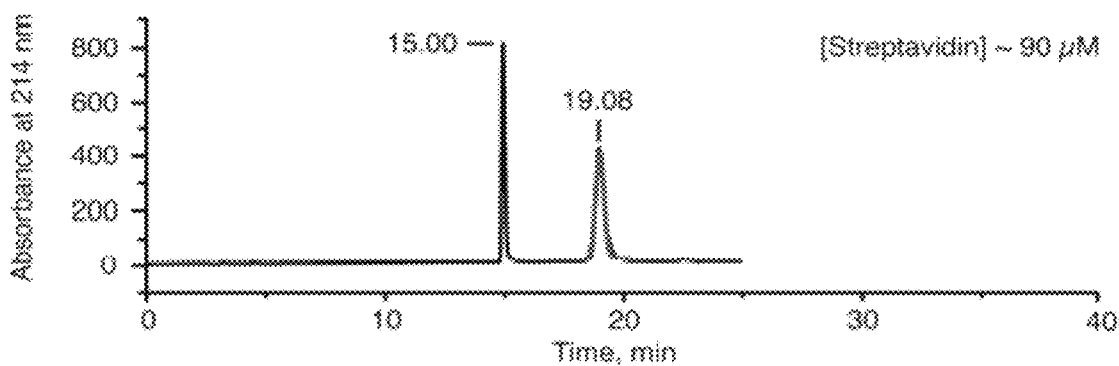
Figure 30B:
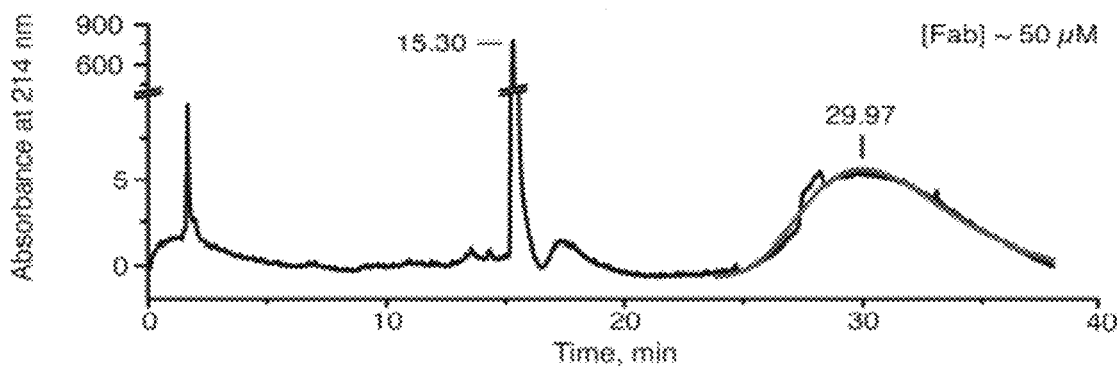

To provide independent evidence that values of $t_d$ can be used to calculate the net charge of proteins used in this work, we determined the net charge of streptavidin (SA), anti-biotin antibody Fab fragments, and monoclonal anti-biotin IgG antibodies (mAb) from capillary electrophoresis (CE) experiments. FIG. 30a, b shows electropherograms for SA and Fab that we obtained using a CE instrument from Hewlett-Packard equipped with a UV absorbance detector. In each electropherogram, two peaks were present due to a transient increase in the absorbance within the light-path of the detector near the end of the capillary. The first peak was due to the so-called neutral marker (a small molecule with a net charge of zero), 4-methoxybenzyl alcohol, and the second peak was attributed to the protein. The difference between the elution time for the neutral marker, $t_{NM}$ (s), and the elution time, $t_A$ (s), for a spherical protein is given by equation (S19)[36]:

$$z = \frac{L_T L_D 6\pi\eta R\left(\dfrac{1}{t_A} - \dfrac{1}{t_{NM}}\right)}{V_A e}, \quad (S19)$$

where $L_T$ (m) is the total length of the capillary, $L_D$ (m) is the length of the capillary to the detector, $\eta$ (Pa×s) is the viscosity of the electrolyte (calculated in this work from equation (S8)), R (m) is the effective radius of the protein, $V_A$ (V) is the applied potential difference across the capillary, and e (C) is the elementary charge of an electron. Based on the volume of the proteins, we estimated an effective radius for SA of 2.9 nm (corresponding to 105 nm$^3$) and for Fab of 3.2 nm (corresponding to 140 nm$^3$). For the mAb, we used an effective radius of 5.5 nm that Jossang et al. determined from the diffusion coefficient of IgG antibodies[32]. Table S3 lists the calculated charge of SA and Fab that we determined from these CE experiments and compares these values to the ones determined from fits to the distributions of $t_d$ values obtained during the nanopore translocation experiments.

Based on CE experiments, we measured slightly different values for the charge of SA than those reported by Sivisankar et al; these deviations increased as the pH decreased. These discrepancies are likely due to the difference in the charge of SA in solution compared the charge of SA bound to a surface by a biotin anchor. The reported pI of SA in solution is 6.3[35] while Sivasankar et al. reported a pI of SA bound to biotinylated lipids of 5-5.5 and Vlassiouk et al. reported a pI of SA bound to immobilized biotin on a surface of ~5.5[35,37]. Since, the experimental conditions used by Sivasankar et al. were very similar to those used here (i.e. SA bound to biotinylated lipids in a lipid bilayer composed of lipids with a head group of phosphatidylcholine), we plotted $t_d$ values in FIG. 5 of the main text versus the values reported by Sivasankar et al.

TABLE S3

Net valence, |z|, of the charge of proteins, diffusion coefficients of proteins within the nanopore, $D_P$, and diffusion coefficients of lipids in the bilayer coating, $D_L$.

| Protein | Lipid Bilayer[a] | pH of electrolyte | $z_{LITERATURE}$ 35 | $z_{CE}$[b] | $z_{Td}$[c] | $D_L$[d] (nm² μs⁻¹) | $D_P$[c] (nm² μs⁻¹) | $\Delta_D$ % |
|---|---|---|---|---|---|---|---|---|
| SA | POPC | 7.4 | −1.9 ± 0.4 | −1.8 ± 0.1 | −0.8 ± 0.2 | 1.13 ± 0.13 | 1.4 ± 0.1 | +24 |
| SA | DΔPPC | 7.4 | −1.9 ± 0.4 | −1.8 ± 0.1 | −1.1 ± 0.2 | 1.56 ± 0.16 | 1.7 ± 0.1 | +9 |
| SA | POPC | 8.0 | −2.4 ± 0.4 | −2.8 ± 0.3 | −2.3 ± 0.2[f] | 1.65 ± 0.17 | 1.8 ± 0.1[f] | +6 |
| SA | POPC | 7.1 | −1.7 ± 0.4 | −0.9 ± 0.2 | −1.6 ± 0.1[f] | 1.65 ± 0.17 | 1.7 ± 0.1[f] | +6 |
| SA | POPC | 6.6 | −1.2 ± 0.4 | −0.7 ± 0.2 | −1.0 ± 0.1[f] | 1.65 ± 0.17 | 1.4 ± 0.1[f] | −15 |
| SA | POPC | 6.1 | −0.8 ± 0.4 | −0.3 ± 0.1 | −0.9 ± 0.1[f] | 1.65 ± 0.17 | 1.0 ± 0.1[f] | −39 |
| SA | POPC | 5.7 | −0.5 ± 0.4 | — | −0.9 ± 0.1[f] | 1.65 ± 0.17 | 1.2 ± 0.1[f] | −21 |
| Fab | POPC | 7.4 | — | −4.3 ± 0.4 | −2.9 ± 0.6 | 1.27 ± 0.13 | 1.7 ± 0.1 | +31 |
| mAb | POPC | 7.4 | — | Peak 1: −0.3 ± 0.3 Peak 2: −3.6 ± 2.3 | −4.2 ± 0.5[e] | 1.29 ± 0.13 | 1.8 ± 0.5 | +38 |

[a]All lipid bilayers also contained 0.15-0.4 mol % of Biotin-PE.
[b]Value of $z_{CE}$ determined by capillary electrophoresis from equation (S19).
[c]Value of $z_{Td}$ and $D_P$ determined by fitting the cumulative distributions of $t_d$ with equation (S13), in which v was described by equation (S20), with both $z_{Td}$ and $D_P$ as fitting parameters.
[d]Values for $D_L$ determined by FRAP as described in Supplementary Section S2.
[e]Value of z determined from the fit in FIG. S17.
[f]Values were determined by fitting equation S21 to histograms.

Figure 30C:
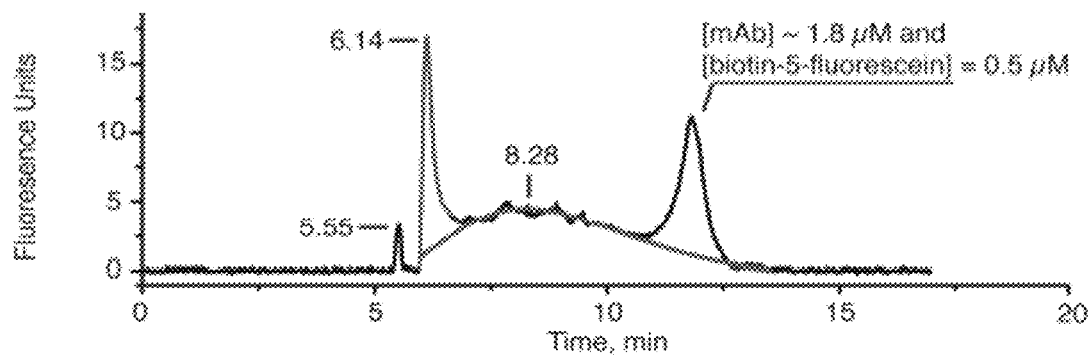

We performed a second set of CE experiments with a CE instrument from Beckman equipped with fluorescence detection. To detect proteins with this instrument, we incubated the anti-biotin IgG antibody with biotin-5-fluorescein prior to performing the CE experiment. FIG. 30c shows the resulting electropherogram, which we used to calculate the net charge of the mAb. Since biotin-5-fluorescein presumably has a net charge of approximately −1 at pH 7.4, we subtracted 1 charge from the value of z determined with equation (S19) to calculate a net charge of the mAb. We observed two peaks in the presence of mAb, both of which grew in size with increasing concentrations of biotin-5-fluorescein. These two peaks did not overlap with the peak of unbound biotin-5-fluorescein and could therefore both represent the antibody-ligand complex. These two peaks after the neutral marker in FIG. 30c correspond to z values of −0.3±0.3 and −3.6±2.3 (Table S3).

S8.3 Fitting Individual Distributions of $t_d$ with Both z and D as Fitting Parameters To determine if parameters such as |z| and $D_L$ could be extracted from distributions of $t_d$ such as those shown in FIG. 3 in the main text, we incorporated the net valence of the charge, |z|, of a protein into equation (S10) by combining it with equation (S20), which describes the electrophoretic drift velocity, v, based on equations (S15)-(S17):

$$v = \frac{|z|eV_P D}{l_P k_B T}. \quad (S20)$$

Substituting equation (S20) into equation (S10) resulted in equation (S21), which permitted the determination of the diffusion coefficient of lipid anchored proteins, $D_P$, and the net valence of the charge of the proteins, |z|, in the nanopore based on best curve fits to individual distributions of $t_d$.

$$P(t_d) = \frac{\left[\left(\frac{|z|eV_P D}{l_P k_B T}\right)t_d + l_P\right] \times e^{-\frac{\left[l_P - \left(\frac{|z|eV_P D}{l_P k_B T}\right)t_d\right]^2}{4Dt_d}}}{t_d \times \sqrt{4Dt_d \pi}}. \quad (S21)$$

Table S3 compares the values of |z| obtained with this method to the literature values of |z| for SA, the values of |z| obtained with CE, the values of $D_P$, and the values of $D_L$ for SA, mAb, and Fab. For Fab, values of |z| and $D_P$ determined with equation (S21) from nanopore-based $t_d$ distributions were in good agreement (±39%) with the expected values as obtained from CE and from FRAP experiments.

For streptavidin, values of |z| determined by Sivasankar et al. agreed well with the values determined by fitting $t_d$ distributions from translocation experiments with SA with equation (S21). The only exception was the experiment with streptavidin in an electrolyte with a pH of 5.7. The difference in the value of |z| of Δz=0.4 in the electrolyte with a pH of 5.7, is likely due to the reduced charge of SA at this pH (|z|=0.5±0.2)[35]. This charge, which is close to neutral, presumably led to a shift from an electrophoretically dominated movement through the nanopore to a diffusion-dominated movement of SA. Consequently, a fraction of the recorded resistive pulses may have been due to partial translocation events (i.e. diffusion of SA into and out of the same side of the nanopore). Such events could be associated with shorter than expected values for $t_d$.

For the mAb, we observed two peaks in the CE data which corresponded to two different charges for the mAb. One of the peaks corresponds to a z=−3.6±2.3, which agrees well with the value of z=−4.2±0.5 determined from the fit in FIG. 29. The second peak in the CE data corresponds to a z=−0.3±0.3. If the charge of the mAb would indeed be −0.3±0.3, then some proteins may only partially move through the nanopore (as discussed for SA at pH 5.7), which may result in shorter than expected values for $t_d$. Consequently, the predictions of the charge of the mAb based on $t_d$ values would calculate values for z that are larger than the true value. However, based on the results in FIG. 29, the charge of the mAb is likely to be z=−3.6 rather than −0.3.

Section S9. Data Acquisition and Analysis of Resistive Pulses for Protein Detection We used Ag/AgCl pellet electrodes (Warner Instruments) to monitor ionic currents through electrolyte-filled nanopores with a patch-clamp amplifier (Axopatch 200B, Molecular Devices Inc.) in voltage clamp mode (i.e., at constant applied voltage). We set the analog low-pass filter of the amplifier to a cutoff frequency of 100 kHz. We used a digitizer (Digidata 1322) with a sampling frequency of 500 kHz in combination with a program written in Lab View to acquire and store data.

To detect resistive pulses caused by the translocation of proteins through the nanopore, we applied a potential difference of ±0.1 V across the nanopore. The polarity refers to the top fluid compartment that contained the protein while the other fluid compartment was always connected to ground. We recorded the resulting current with the maximum bandwidth of the recording setup (cut-off frequency, $f_c$~50 kHz)[38] and with a sampling frequency of 500 kHz using a custom program written in LabVIEW. To distinguish resistive pulses reliably from the electrical noise, we used the software PClamp (Molecular Devices Inc.) to determine the baseline of the current and to filter current recordings with a digital, Gaussian low-pass filter ($f_c$=15 kHz).

Using PClamp software, we performed a threshold-search for resistive pulses within the current recordings. We defined the start of a resistive pulse by a resistive decrease in the magnitude of the current past a threshold value that we set to 5× the standard deviation of the noise of the baseline current. Based on this definition, typical threshold values ranged from 150 to 250 pA depending on the nanopore dimensions and the bilayer coating. The subsequent return of the current past a second threshold, which we set to one standard deviation of the noise in the baseline current, and toward the baseline value, marked the end of the resistive pulse. We confirmed that for the analysis of translocation events from streptavidin and Fab, this procedure returned the same $t_d$ values as a method based on half-widths of resistive pulse recently reported by Talaga and Li[24]. Due to the large magnitude and magnitude variability of resistive pulses in the antibody experiments, we determined $t_d$ values based on the half-width of resistive pulses from antibodies in a method similar to the approach described by Talaga and Li[24]. We defined ΔI as the maximum deviation from the baseline current within the time, $t_d$.

Figure 31A:
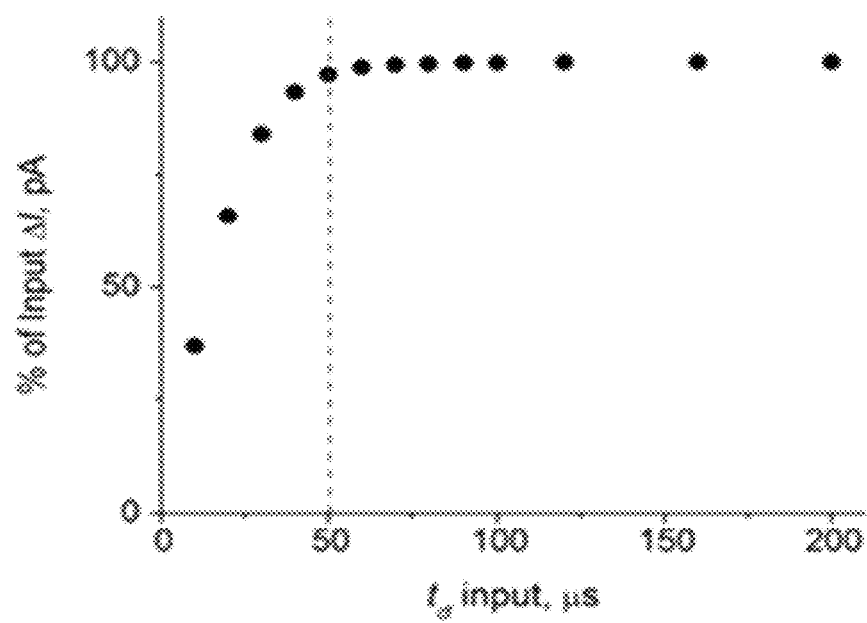
Figure 31B:
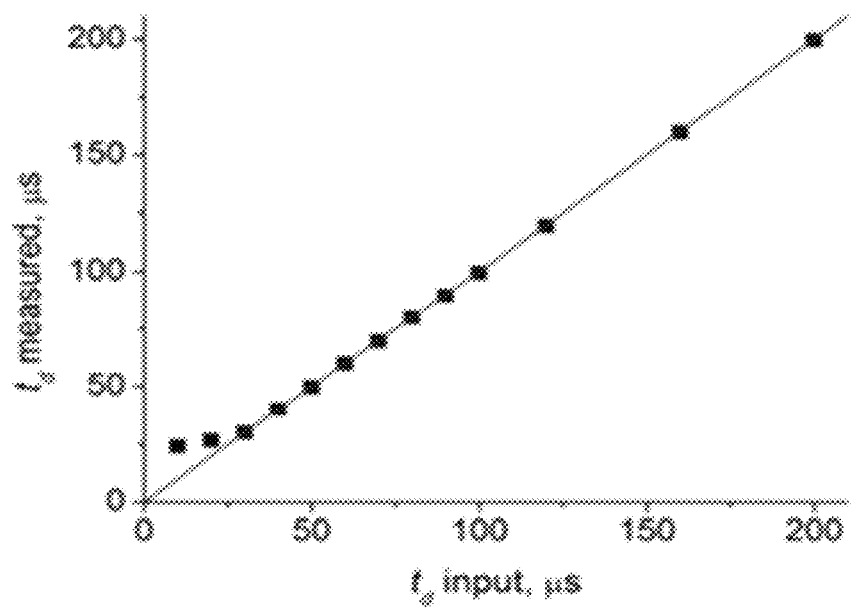

To determine the time-response of the recording and analysis methods experimentally, we used a waveform generator (Agilent 33220A) to input current pulses in a method similar to Talaga and Li[24]. These current pulses had a ΔI of 650 pA with a rise time of 5 ns and durations ranging from 10 μs to 200 μs. Analyzing the data based on the half-width of the current pulses, FIG. 31a shows that we could accurately measure the magnitude (ΔI) of resistive pulses if these pulses had $t_d$ values larger than 50 μs and FIG. 31b shows that we could accurately determine $t_d$ values that were larger than 25 μs. In all quantitative analyses of resistive pulses reported in this work, we constructed $t_d$ histograms only from translocation events that lasted at least 25 μs and M histograms only from translocation events that lasted at least 50 μs (typically 70 μs).

Figure 32:
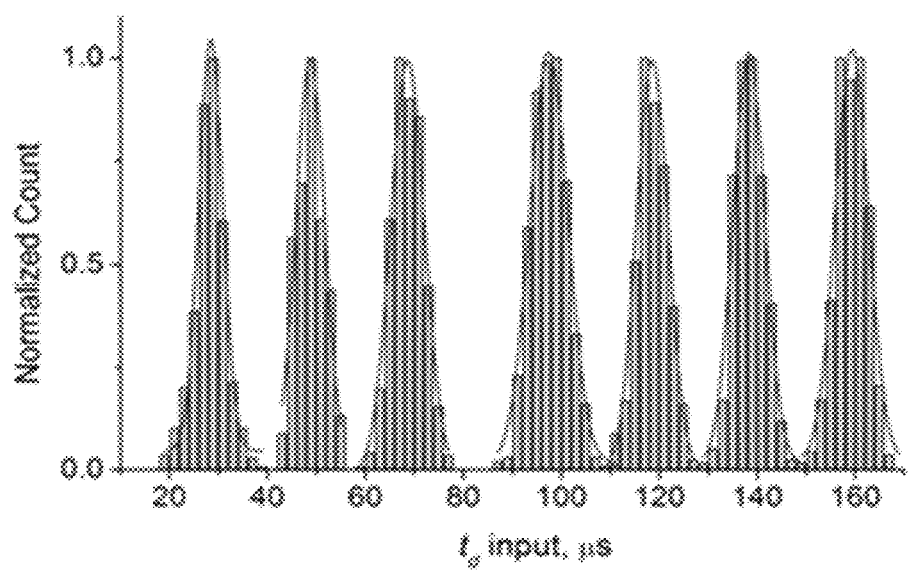

To characterize the inherent measurement error of $t_d$, $\sigma_t$, of the recording and analysis methods, we added a current trace containing experimentally recorded electrical noise from a resistive-pulse experiment to current traces containing current pulses generated by a waveform generator. Thus, these current traces contained current pulses with a precisely defined duration and contained a realistic representation of the electrical noise in a resistive pulses experiment. Using the resulting current traces we determined $t_d$ based on the half-width of the current pulses as described above. For current pulses with a precisely defined duration, we measured a range of $t_d$ values and FIG. 32 plots these values in histograms. We fit these histograms with Gaussian distributions, and from the fit we determined that the inherent measurement error of $t_d$ ranged from 2 to 4 μs and was not affected by the magnitude of $t_d$.

Section S10. Preparation of Amyloid-Beta Samples and Gel-Electrophoresis

We received Aβ peptides (residues 1-40, Aβ 1-40) in powder form from GL *Biochem* (Shanghai) Ltd with a purity above 98%. To remove aggregates of Aβ 1-40, we dissolved the powder in hexafluoroisopropanol (HFIP) to a concentration of 1 mM of Aβ 1-40. After 24 h incubation in HFIP, we diluted this solution with cold (4° C.) deionized water at a 2:1 (v/v) ratio ($H_2O$:HFIP). We then rapidly aliquoted the solution, immediately froze it in a $CO_2$/acetone bath, and lyophilized the frozen aliquots for two days to remove HFIP[39]. To start the aggregation process of Aβ 1-40 peptides, we dissolved the lyophilized powder in deionized water to a concentration of 1 mg×mL$^{-1}$. We incubated these samples in siliconized plastic microcentrifuge tubes on a temperature-controlled shaker at a temperature of 22° C. To detect aggregates of Aβ 1-40, we formed a supported lipid bilayer of POPC lipids on a chip containing a nanopore with a diameter of 96 nm and a length of ~275 nm (dimensions are before the lipid bilayer coating). We added solutions containing Aβ 1-40 to the top solution compartment of the fluidic setup such that the final concentration of Aβ 1-40 ranged from 0.1 to 0.2 mg×mL$^{-1}$. We used a recording buffer containing 70 mM KCl and 10 mM HEPES with a pH of 7.4±0.1 and recorded resistive pulses at an applied potential difference of +0.2 V.

Figure 33:
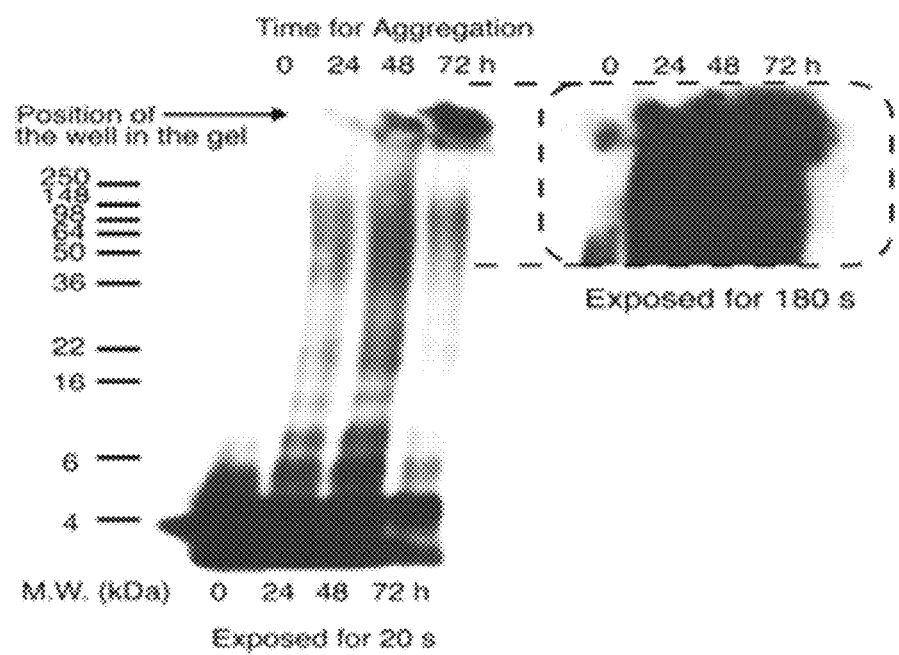

To confirm the presence of large aggregates of A☐ peptides in these samples independently, we performed a Western blot with solutions containing Aβ(1-40) that were allowed to aggregate for 0, 24, 48, and 72 h. Prior to performing the electrophoresis, we followed a standard protocol[40] and cross-linked Aβ(1-40) samples (1 mg mL$^{-1}$) with 0.04% glutaraldehyde for 20 min at room temperature and stopped the reaction by adding 200 mM of Tris. We diluted the cross-linked samples to 0.01 μg μL$^{-1}$ in native sample buffer (Bio-Rad), containing 10% (v/v) sodium dodecyl sulfate. To resolve aggregates of Aβ(1-40) of different molecular weights we used a polyacrylamide gel: 18% Tris-HCl Ready Gel (Bio-Rad) in Tris-Glycine buffer. After running the gel, we transferred proteins to a polyvinylidene fluoride (PVDF) membrane (PerkinElmer Life Science) and blocked the membrane for 1 h with TBS buffer containing 5% (w/v) nonfat dry milk and 0.0625% (w/v) Tween20. We incubated the membrane with a primary antibody against Aβ(1-40) (6E10 from Covance) for 1.5 h. An IgG anti-goat antibody served as the secondary antibody and was incubated with the membrane for 1 h. We developed the membrane onto film using enhanced chemiluminescence (ECL, PerkinElmer Life Sciences). FIG. 33 shows the resulting Western blot and the increasing molecular weights of Aβ(1-40) aggregates with increasing incubation time. Note the presence of fibrillar aggregates with molecular weights greater than 250 kDa that remained in the wells of the polyacrylamide gel. Also note that the amount of these fibrillar Aβ(1-40) aggregates in the wells of the gel increased with increasing time of aggregation.

References for the Supplemental Information Sections S1-S10

1 Grover, N. B., Naaman, J., Ben-sasson, S., Doljansk, F. & Nadav, E. Electrical sizing of particles in suspensions. 2. Experiments with rigid spheres. *Biophys. J.* 9, 1415-1425 (1969).

2 Grover, N. B., Naaman, J., Ben-sasson, S. & Doljansk, F. Electrical sizing of particles in suspensions. I. Theory. *Biophys. J.* 9, 1398-1414 (1969).

3 Hille, B. *Ion Channels of Excitable Membranes*. (Sinauer Associates, Inc., Sunderland, 2001).

4 Cai, Q., Ledden, B., Krueger, E., Golovchenko, J. A. & Li, J. L. Nanopore sculpting with noble gas ions. *J. Appl. Phys.* 100, 024914 (2006).

5 Li, J. et al. Ion-beam sculpting at nanometre length scales. *Nature* 412, 166-169 (2001).

6 Hamann, C. H., Hamnett, A. & Vielstich, W. *Electrochemistry*. (Wiley-VCH, New York, 1998).

7 Fox, R. W., McDonald, A. T. & Pritchard, P. J. *Introduction to Fluid Mechanics 6th Edition*. (Wiley, New York, N.Y., 2004).

8 Schuy, S. & Janshoff, A. Thermal expansion of microstructured DMPC bilayers quantified by temperature-controlled atomic force microscopy. *ChemPhysChem* 7, 1207-1210 (2006).

9 Tokumasu, F., Jin, A. J. & Dvorak, J. A. Lipid membrane phase behaviour elucidated in real time by controlled environment atomic force microscopy. *J. Electron Microsc.* 51, 1-9 (2002).

10 Reimhult, E., Hook, F. & Kasemo, B. Intact vesicle adsorption and supported biomembrane formation from vesicles in solution: Influence of surface chemistry, vesicle size, temperature, and osmotic pressure. *Langmuir* 19, 1681-1691 (2003).

11 Lambacher, A. & Fromherz, P. Fluorescence interference-contrast microscopy on oxidized silicon using a monomolecular dye layer. *Appl. Phys. A-Mater. Sci. Process.* 63, 207-216 (1996).

12 Saleh, B. E. A. & Teich, M. C. pg. 80 (John Wiley & Sons, Inc., 2007).

13 Majd, S. & Mayer, M. Hydrogel stamping of arrays of supported lipid bilayers with various lipid compositions for the screening of drug-membrane and protein-membrane interactions. *Angew. Chem.-Int. Edit.* 44, 6697-6700 (2005).

14 Axelrod, D., Koppel, D. E., Schlessinger, J., Elson, E. & Webb, W. W. Mobility Measurement by Analysis of Fluorescence Photobleaching Recovery Kinetics. *Biophys. J.* 16, 1055-1069 (1976).

15 Soumpasis, D. M. Theoretical-Analysis of Fluorescence Photobleaching Recovery Experiments. *Biophys. J.* 41, 95-97 (1983).

16 Kalb, E., Frey, S. & Tamm, L. K. Formation of Supported Planar Bilayers by Fusion of Vesicles to Supported Phospholipid Monolayers. *Biochimica Et Biophysica Acta* 1103, 307-316 (1992).

17 Stan, T. E. & Thompson, N. L. Formation and characterization of planar phospholipid bilayers supported on TiO2 and SrTiO3 single crystals. *Langmuir* 16, 10301-10308 (2000).

18 Majd, S., Yusko, E. C., MacBriar, A. D., Yang, J. & Mayer, M. Gramicidin pores report the activity of membrane-active enzymes. *J. Am. Chem. Soc.* 131, 16119-16126 (2009).

19 Hamblen, K. J. et al. A streptavidin-biotin binding system that minimizes blocking by endogenous biotin. *Bioconjugate Chem.* 13, 588-598 (2002).

20 Janeway, C. A. *Immunobiology: the immune system in health and disease.* 5th edn, (Garland Publishing, New York, 2001).

21 Fein, M. et al. Lateral mobility of lipid analogs and GPI-anchored proteins in supported bilayers determined by fluorescent bead tracking. *J. Membr. Biol.* 135, 83-92 (1993).

22 Knight, J. D. & Falke, J. J. Single-molecule fluorescence studies of a pH domain: New insights into the membrane docking reaction. *Biophys. J.* 96, 566-582 (2009).

23 Gambin, Y. et al. Lateral mobility of proteins in liquid membranes revisited. *Proc. Natl. Acad. Sci. U.S.A.* 103, 2098-2102 (2006).

24 Talaga, D. S. & Li, J. L. Single-molecule protein unfolding in solid state nanopores. *J. Am. Chem. Soc.* 131, 9287-9297 (2009).

25 Redner, S. *A Guide to First-Passage Processes.* pp. 87-89 (Cambridge University Press, New York, 2001).

26 Wasan, M. T. *First Passage Time Distribution of Brownian Motion with Positive Drift.* pp. 6 and 15 (Queen's University, 1969).

27 Schneider, S M., Larmer, J., Henderson, R. M. & Oberleithner, H. Molecular weights of individual proteins correlate with molecular volumes measured by atomic force microscopy. *Pflugers Arch.* 435, 362-367 (1998).

28 Mathe, J., Aksimentiev, A., Nelson, D. R., Schulten, K. & Meller, A. Orientation discrimination of single-stranded DNA inside the alpha-hemolysin membrane channel *Proc. Natl. Acad. Sci. U.S.A.* 102, 12377-12382 (2005).

29 Akeson, M., Branton, D., Kasianowicz, J. J., Brandin, E. & Deamer, D. W. Microsecond Time-Scale Discrimination Among Polycytidylic Acid, Polyadenylic Acid, and Polyuridylic Acid as Homopolymers or as Segments Within Single RNA Molecules. *Biophys. J.* 77, 3227-3233 (1999).

30 Yang, J., Mayer, M., Kriebel, J. K., Garstecki, P. & Whitesides, G. M. Self-assembled aggregates of IgGs as templates for the growth of clusters of gold nanoparticles. *Angew. Chem.-Int. Edit.* 43, 1555-1558 (2004).

31 Berg, H. C. *Random Walks in Biology.* 81-84 (Princeton University Press, Princeton, N.J., 1993).

32 Jossang, T., Feder, J. & Rosenqvist, E. Photon-Correlation Spectroscopy of Human-IgG. *J. Protein Chem.* 7, 165-171 (1988).

33 Whitlock, M. C. & Schluter, D. *The Analysis of Biological Data.* 1 edn, 33-34 (Roberts and Company, Greenwood Village, Colo., 2009).

34 Sexton, L. T. et al. An adsorption-based model for pulse duration in resistive-pulse protein sensing. *J. Am. Chem. Soc.* 132, 6755-6763 (2010).

35 Sivasankar, S., Subramaniam, S. & Leckband, D. Direct molecular level measurements of the electrostatic properties of a protein surface. *Proc. Natl. Acad. Sci. U.S.A.* 95, 12961-12966 (1998).

36 Gitlin, I., Carbeck, J. D. & Whitesides, G. M. Why are proteins charged? Networks of charge-charge interactions in proteins measured by charge ladders and capillary electrophoresis. *Angew. Chem.-Int. Edit.* 45, 3022-3060 (2006).

37 Vlassiouk, I., Kozel, T. R. & Siwy, Z. S. Biosensing with Nanofluidic Diodes. *J. Am. Chem. Soc.* 131, 8211-8220 (2009).

38 Uram, J. D., Ke, K. & Mayer, M. Noise and bandwidth of current recordings from submicrometer pores and nanopores. *ACS Nano* 2, 857-872 (2008).

39 Capone, R. et al. Amyloid-beta-induced ion flux in artificial lipid bilayers and neuronal cells: Resolving a controversy. *Neurotox. Res.* 16, 1-13 (2009).

40 Stine, W. B., Dahlgren, K. N., Krafft, G. A. & LaDu, M. J. In vitro characterization of conditions for amyloid-beta peptide oligomerization and fibrillogenesis. *J. Biol. Chem.* 278, 11612-11622 (2003).

Supporting Information

Single Particle Characterization of AD Oligomers in Solution.

S11. Nanopores without a Fluid Lipid Coating Clog Due to Adsorption of Aβ

Figure 34:
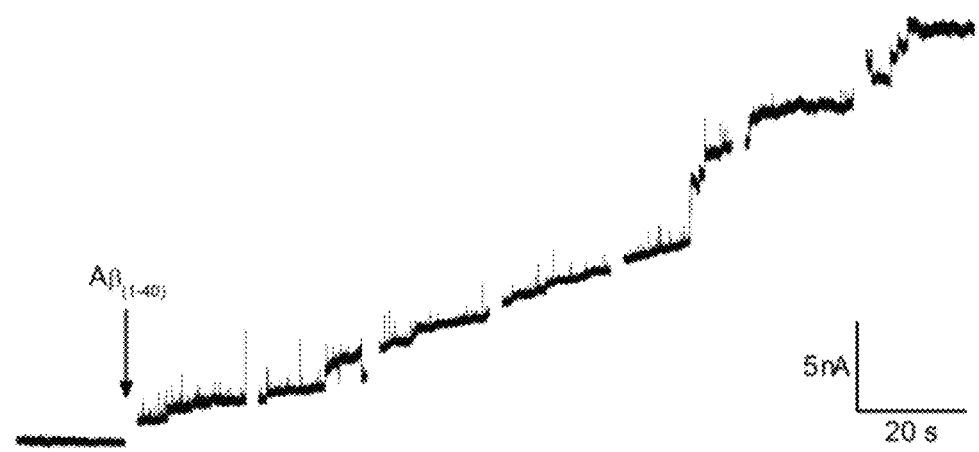
Figure 35:
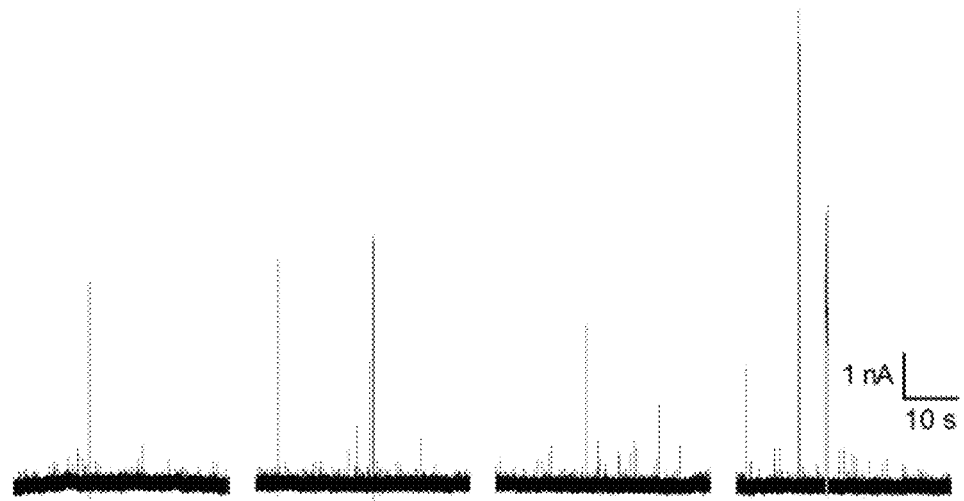

See FIGS. 34 and 35.

S12. Preparation of Aβ Aggregates and Nanopore-Based Sensing Experiments

We received $A\beta_{(1-40)}$ peptides in powder form from GL Biochem (Shanghai) Ltd with a purity above 98%. To remove aggregates of $A\beta_{(1-40)}$, we dissolved the powder in hexafluoroisopropanol (HFIP) to a concentration of 1 mM of $A\beta_{(1-40)}$.[2] After 24 h incubation in HFIP, we diluted this solution with cold (4° C.) deionized water at a 2:1 (v/v) ratio ($H_2O$:HFIP). We then rapidly aliquoted the solution, immediately froze it in a liquid nitrogen bath, and lyophilized the frozen aliquots for two days to remove HFIP. To start the aggregation process of $A\beta_{(1-40)}$ peptides, we dissolved the lyophilized powder in deionized water to a concentration of 1 mg×mL$^{-1}$. We incubated these samples in 0.5 mL closed siliconized plastic microcentrifuge tubes on a temperature-controlled shaker (Thermocycler, Eppendorf) set to 750 rpm at a temperature of 22° C. for zero, one, two and three days.

To detect aggregates of $A\beta_{(1-40)}$, we first formed a supported lipid bilayer of 1-palmitoyl-2-oleoyl-sn-glycero-3-phosphocholine (POPC) lipids (Avanti Polar Lipids, Inc.) on a nanopore that was 28 nm in diameter and had a length of 18 nm, resulting in a coated diameter of approximately 18 nm and coated length of 28 nm.[1] We described details of the bilayer formation in Yusko et al.[1] We added solutions containing $A\beta_{(1-40)}$ to the top solution compartment of the fluidic setup (2 M KCl with 10 mM HEPES pH 7.4) such that the final concentration of $A\beta_{(1-40)}$ ranged from 0.07 to 0.025 mg×mL$^{-1}$. We recorded resistive pulses at an applied potential difference of −0.2 V with the polarity referring to the top fluid compartment relative to the bottom fluid compartment, which was connected to ground. Recordings were completed within 10 to 15 minutes of adding $A\beta_{(1-40)}$.

We used Ag/AgCl pellet electrodes (Warner Instruments) to monitor ionic currents through electrolyte-filled nanopores with a patch-clamp amplifier (Axopatch 200B, Molecular Devices Inc.) in voltage-clamp mode (i.e., at constant applied voltage). We set the analog low-pass filter of the amplifier to a cutoff frequency of 100 kHz. We used a digitizer (Digidata 1322) with a sampling frequency of 500 kHz in combination with a program written in LabView to acquire and store data.[3] To distinguish resistive pulses reliably from the electrical noise, we first filtered the data digitally with a Gaussian low-pass filter ($f_c$=15 kHz) in MATLAB and then used a modified form of the custom written MATLAB routine described in Pedone et al.[4] We modified the MATLAB routine to calculate the translocation time, $t_d$, as the width of individual resistive-pulse at half of their peak amplitude, also known as the full-width-half-maximum value.[1,5] From this analysis we obtained the ΔI and $t_d$ values for each resistive pulse.

S13. Gel Electrophoresis Experiments

Figure 36A:
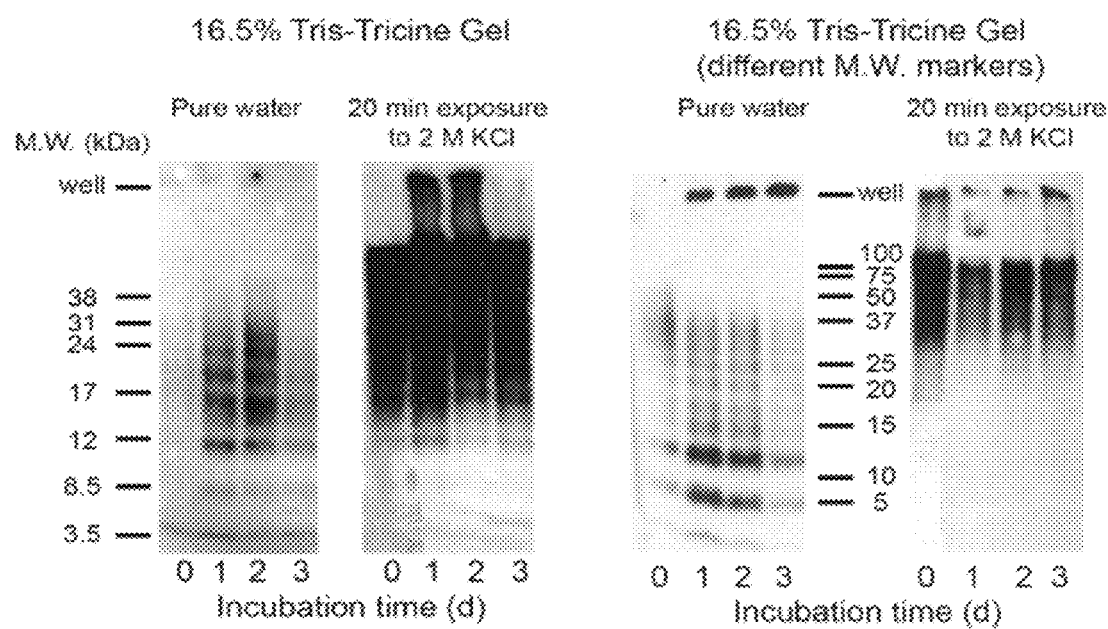
FIG. 36A and FIG. 36B show gel electrophoresis results showing $A\beta_{(1-40)}$ aggregates after zero, one, two, and three days of aggregation time.

To confirm the presence of aggregates of Aβ peptides in the samples, we performed a Western blot with solutions containing $Aβ_{(1-40)}$ that were allowed to aggregate under the same conditions for zero to three days.[1] Prior to performing the electrophoresis, we aliquoted 0.5 μL of 1 mg×mL$^{-1}$ $Aβ_{(1-40)}$ (in pure water) into 38 μL of pure water or into 38 μl of 2 M KCl, resulting in a concentration of $Aβ_{(1-40)}$ of 0.0129 mg mL$^{-1}$—roughly the same concentration used in the nanopore-based characterization. We immediately cross-linked these $Aβ_{(1-40)}$ samples by adding 4 μL of 0.6875% (v/v) glutaraldehyde in water. After 10-20 min at room temperature, we stopped the cross-linking reaction by adding 44.7 μL of 200 mM Tris buffer. We aliquoted 10 μL of these samples into 20 μL of Native Sample Buffer (Bio-Rad: 62.5 mM Tris-HCl pH 6.8, 40% glycerol, 0.01% Bromophenol Blue), which we modified to also contain 10% (v/v) sodium dodecyl sulfate (SDS) and 0.02 M β-mercaptoethanol. To resolve aggregates of $Aβ_{(1-40)}$ of different molecular weights, we used a polyacrylamide gel: 16.5% Tris-Tricine Ready Gel (Bio-Rad) in Tris-Tricine buffer or a 7.5% Tris-HCl Ready Gel (Bio-Rad) in Tris-Glycine Buffer following standard electrophoresis protocols.[6] After running the gels, we transferred proteins to a polyvinylidene fluoride (PVDF) membrane (PerkinElmer Life Science) and blocked the membrane for 1 h with TBS buffer containing 5% (w/v) nonfat dry milk and 0.0625% (w/v) Tween-20. We incubated the membrane with a primary antibody against $Aβ_{(1-40)}$ (6E10 from Covance) for 1.5 h. An IgG anti-goat antibody conjugated to horseradish peroxidase served as the secondary antibody and was incubated with the membrane for 1 h. We developed the membrane onto film using enhanced chemiluminescence (ECL, PerkinElmer Life Sciences). FIG. 36 shows the results of these gel electrophoresis experiments.

Figure 36B:
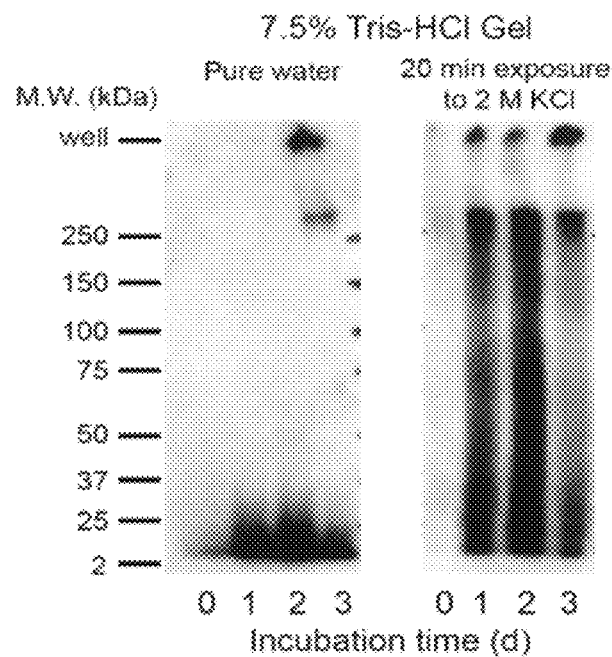

FIG. 36 confirms that the procedure described above generates aqueous solutions containing mostly pentameric $Aβ_{(1-40)}$ aggregates or smaller aggregates on day zero and increasingly larger aggregates after one, two, or three days of aggregation time. FIG. 36 also shows the accelerated aggregation of $Aβ_{(1-40)}$ in the presence of 2 M KCl for ~20 min (the shortest possible time for the gel electrophoresis procedure). Regardless of this accelerated aggregation, time-dependent aggregation to higher molecular weight aggregates is apparent by the increasingly darker bands in the wells, where fibers are retained, over time. Additionally, FIG. 36B highlights that in the 50-250 kDa aggregates increasingly larger aggregates develop between 1 and 3 days of aggregation, eventually resulting in a relatively darker, larger band in the well on Day 3 compared to Days 1 and 2. This result is important since 50 kDa is approximately the minimum molecular weight of protofibrils and marks the beginning of the transition from spherical oligomers into cylindrical protofibrils.[7] We confirmed by TEM analysis that the increased aggregation rate due to the high ionic strength did not affect the morphology of the fibrils (see Supporting Information S18).

S14. Additional Comparison of Aβ Aggregates Sizes Determined by Nanopore-Based Characterization and TEM.

To cross-examine our assumptions and results from the cluster analysis, we applied equation (2) to ΔI values from cluster (i) to estimate a cross-sectional area of aggregates in this cluster, and we applied equation (1) to ΔI values from clusters (iii) and (iv) to estimate the excluded volumes of these aggregates; this analysis ignores the requirement for $l_M < L_{eff}$ for equation (1) and $l_M > L_{eff}$ for equation (2). Finally, we searched the TEM images (FIG. 3 in the main text and Supporting Information S8) for aggregates with the sizes predicted by this analysis and did not find aggregates in the TEM images with these sizes or shapes. For instance, if we incorrectly apply equation (2) to the data in cluster (i) (i.e. if we enforce that aggregates in cluster (i) have $l_M > l_{eff}$), we obtain cylindrical diameters of 1.9 nm. We did not observe elongated aggregates of $Aβ_{(1-40)}$ with diameters this small in the TEM images, suggesting that aggregates classified in cluster (i) should indeed be approximated as spherical oligomers with equation (1) in the main text in agreement with the approach that we used. Similarly, if we incorrectly assume that the requirement of $l_M < l_P$ for equation (1) was satisfied by the molecules represented in clusters (iii) and (iv), we obtained spherical diameters of 9.4 nm and 12.6 nm, respectively. We typically did not observe spherical aggregates of $Aβ_{(1-40)}$ with diameters greater than 9 nm in the TEM images (i.e. only 10 out of 347 observed aggregates had spherical diameters of 9 nm or larger), suggesting that the aggregates represented in cluster (iii) are indeed protofibrils and that the aggregates represented in cluster (iv) are indeed fibers longer than the effective length of the nanopore, again in agreement with the approach we used in the main text.

These results show that the cluster assignment of translocation events by statistical cluster analysis of M and $t_d$ values of each event yielded diameter and lengths of Aβ aggregates that are consistent with observations by TEM.

S15. Distributions of to Values in Clusters (i) and (ii)

Figure 37:
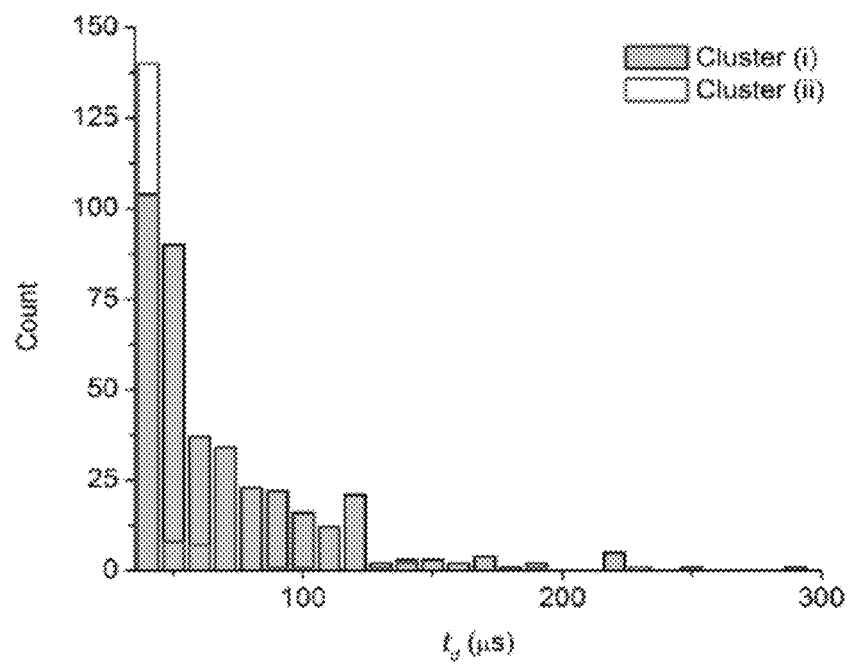
FIG. 37 is a histogram of translocation times of $A\beta$ aggregates that were classified into clusters (i) and (ii). The width of the bins in the histogram is 10 µs, and the first bin starts at 35 µs since that was the minimum translocation time that could be determined accurately.[4] As a result, the complete distribution of translocation times could not be obtained.

Discussion about the Results in FIG. 37:

The observation that almost all translocation events in cluster (ii) had a $t_d$ value between 35 μs and 45 μs compared to the more distributed $t_d$ values in cluster (i) suggests that the aggregates in cluster (ii) had increased electrophoretic mobility.[5,8] The resulting shorter time for translocation through the pore minimized time-dependent diffusional spreading and, therefore, led to a narrower distribution of $t_d$ values compared to events in cluster (i). The reasons for this increased electrophoretic mobility of events in cluster (ii) could be decreased interactions with the lipid bilayer coating[1] or an orientation of the aggregate in the nanopore that reduces viscous drag, such as a prolate or cylinder moving with its long axis parallel to the direction of movement.[9] As a third possibility, this result could be due to an increasing charge per aggregate at a constant charge per monomer addition, if electrostatic effects are neglected and we assume spherical aggregates. With the latter two assumptions, the mathematical relationship between the most-probable translocation time, diffusion constant, charge, and molecular weight involves equations (S1)-(S3):

$$|z| = \left|\frac{-3}{4.3 kDa}\right| \times N, \tag{S1}$$

-continued $$D = \frac{k_B T}{6\pi\eta \left(\frac{3M.W.}{4\pi A_v \rho}\right)^{1/3}},$$ (S2)[9]

and $$t_d = \frac{l_P^2 k_B T}{|z|eV_P D}$$ (S3)[1]

where, z is the net charge valence of the aggregate, N is the number of monomers in the aggregate, D (m² s⁻¹) is the diffusion constant of the aggregate, M. W. (kDa) is the molecular weight of the aggregate (i.e. here 4.3 kDa×N), $k_B$ (J K⁻¹) is Boltzmann's constant, T (K) is the temperature, η (Pa s) is the viscosity of the solution, $A_v$ is Avagadro's number, ρ (kDa m⁻³) is the molecular weight density of amino acids in a protein, $l_P$ (nm) is the length of the nanopore, e (C) is the elementary charge of an electron, and $V_P$ (V) is the voltage drop across the nanopore. The factor of −3/4.3 kDa in equation (1) is included to account for the expected net charge per Aβ(1-40) monomer of −3 and the molecular weight of a monomer of 4.3 kDa.[10,11] By combining equations (S1)-(S3), we solved for $t_d$ as a function of the number of monomers in the aggregate, $V_P$, and a constant c to yield equation (S4):

$$t_d = \frac{c}{N^{2/3} V_P}$$ (S4)

FIG. 38 shows a plot of equation (S4) and illustrates the trend in most-probable translocation times for aggregates with increasing molecular weight, assuming a constant charge to mass ratio, a constant applied voltage, a spherical aggregate, and an aggregate with a length less than the length of the nanopore. This analysis shows that increasing the number of monomers in a low-molecular weight aggregate could conceivably increase the electrophoretic force more than the viscous drag force, resulting in decreased translocation times that are more narrowly distributed[5,8] as the aggregates molecular weight, and hence charge, increases. This analysis does not apply to aggregates in clusters (iii) or (iv), since those aggregates have lengths longer than the length of the nanopore.

S16. Protofibril Diameters as a Function of their Length Determined by TEM Analysis.

See FIG. 39.

S17. Estimation of Protofibril Lengths

To generate histograms of the lengths of aggregates in clusters (i) and (ii) of the main text (FIG. 3), we expected that these aggregates were protofibrils elongating with a constant diameter[12] and hence had an area-equivalent cylindrical diameter, 8c, of 4.4 nm (Table 1 in the main text). We also expected that protofibrils were oriented with their length, $l_M$, parallel to the length of the nanopore and hence electric field.[13-15] We defined the excluded volume of an aggregate and the shape factor of an aggregate as a function of its length and solved a system of equations for γ and $l_M$ based on the ΔI value of each translocation event.

Since TEM analysis (Supporting Information S16) and data in the literature[12] show that the diameter of protofibrils is relatively constant and independent of length, we defined their excluded volume as the volume of a perfect cylinder:

$$\Lambda = \frac{1}{4}\pi \theta_c l_M,$$ (S5)

Substituting equation S5 into equation (1) of the main text yields ΔI as a function of γ and $l_M$:

$$\Delta I(\gamma, l_M) = \frac{\gamma V_A \pi \theta_c l_M}{4\rho(l_P + 1.6 r_P)^2} \text{ for } l_M < l_{\text{eff}}.$$ (S6)

To estimate a shape factor for this analysis, we used equations derived by Fricke[16,17] that describe the shape factor of spheroidal prolate particles. A prolate can be described by three dimensions of lengths, a, b, and c. For a perfectly ellipsoidal (spheroidal) prolate, b=c, and in Cartesian coordinates it is described by x²/c²+y²/b²+z²/a²=1. Equations yielding the same shape factor, but through a different derivation processes that can be extended to non-symmetirc spheroids, can be found in reports by Goliber-such, Deblois et al., and Osborn.[18-21] According to Fricke, when the longest axis, a, is parallel to the electric field, the shape factor, $\gamma_\parallel$, is:

$$\gamma_\parallel = \left[\frac{m^2}{m^2-1} - \frac{m\cosh^{-1}(m)}{(m^2-1)^{3/2}}\right]^{-1},$$ (S7)

where m=a/b=a/c and is greater than 1. Since we define the diameter of the aggregates in this section as θc=4.4 nm, we set m=$l_M$/θc and rewrite equation S7:

$$\gamma_\parallel = \left[\frac{(l_M/\theta_c)^2}{(l_M/\theta_c)^2-1} - \frac{(l_M/\theta_c)\cosh^{-1}(l_M/\theta_c)}{((l_M/\theta_c)^2-1)^{3/2}}\right]^{-1}.$$ (S8)

Finally, we solved equations S6 and S8 using MATLAB to obtain values of γ and 1M for each aggregate based on its ΔI value. The lengths obtained for the aggregates are shown in a histogram in FIG. 3 of the main text. The values for γ in cluster (i) ranged from 1.5 to 1.2 with an average of 1.35, and in cluster (ii) γ ranged from 1.048 to 1.2 with an average of 1.13.

While the analysis above provides a good first approximation for the lengths of aggregates in clusters (i) and (ii), we would like to point out two important limitations of this method. First, since the aggregates in cluster (i) are significantly shorter than the length of the nanopore, it is possible that the shortest ones among them rotate within the nanopore and thus do not have a constant shape factor. We can estimate an average shape factor if we consider the shape factor of a prolate with its axis a perpendicular to the electric field:

$$\gamma_\perp = \frac{2\gamma_\parallel}{2\gamma_\parallel - 1},$$ (S9)

The average shape factor for a prolate free to rotate about all axes is[20]:

$$\gamma_{AVG} = \tfrac{1}{3}\gamma_\parallel + \tfrac{2}{3}\gamma_\perp.$$ (S10)

Using the average shape factor relationship in equation (S10) for the aggregates in cluster (i) and MATLAB to solve equations (S6) and (S8)-(S10) yields the lengths shown in Figure S8A and a shape factor that ranged from 1.50-1.52. This value is nearly identical to the shape factor of 1.5 commonly used for spherical objects (i.e. the shape factor we used to calculate the excluded volume for cluster (i) in Table 1 of the main text). We should highlight, however, that even a spheroidal prolate that is slightly elongated, will not be free to rotate horizontally (i.e. with axis a perpendicular to the electric field) through the entire nanopore due to steric hindrances. FIG. 40B approximates the fraction of pore area (cross-sectional area) that a cylinder of length $l_M$ could occupy while in a horizontal orientation. Thus, it is likely that aggregates in cluster (i) and cluster (ii) will be aligned in the nanopore due to the converging electric field as well as steric effects. In reality the smallest aggregates in cluster (i) may rotate while the longest aggregates are aligned in the electric field. This effect would close the mathematically created gap between the distributions of lengths for the aggregates in clusters (i) and (ii) (Figure S8A).

The second concern with the analysis at the beginning of this sections stems from defining the geometry of aggregates in clusters (i) and (ii) as cylindrical (since TEM images revealed that the diameter of many aggregates remained constant independent of length, Supporting Section S16) while applying the shape factor for a prolate. An alternative approach is to define the shapes of the aggregates as spheroidal prolates rather than cylinders. The excluded volume of a perfect spheroidal prolate is:

$$\Lambda = 4/3 \pi bca$$

or using the parameter symbols in this work $$\Lambda = \tfrac{1}{6}\pi \theta_c^2 l_M \qquad (S11).$$

Solving the system of equations described above with equation (S11) replacing (S5) yields the distribution of lengths shown in FIG. 41. As before, we assumed that all aggregates were aligned with their length axis parallel to the length of the nanopore and the electric field. The shape factor for the aggregates in cluster (i) ranged from 1.10-1.25 with an average value of 1.17, and for the aggregates in cluster (ii) γ ranged from 1.02 to 1.10 with an average value of 1.07. If we assume that the aggregates in cluster (i) can rotate in three dimensions, as in the previous paragraph, then the average shape factor for the aggregates in cluster (i) is 1.55, and the distribution of lengths is slightly narrower than those shown in FIG. 41. Note that the lengths in this distribution are ~1.5 times the lengths shown in FIG. 3 of the main text. This result is a consequence of the fact that for a prolate and cylinder with the same volume, the prolate will have a length 1.5 times that of the length of the cylinder. Again, the best method probably lies between estimating the volumes of aggregates based on the shape of a cylinder and the shape of a prolate.

To summarize this section, we estimated the lengths of aggregates in clusters (i) and (ii) by solving a system of equations including $\gamma(l_M)$ and $4/(\gamma, l_M)$. The resulting lengths and shape factors were dependent on whether the volume of the aggregate was constrained to a cylindrical shape or a prolate spheroid shape. Regardless, the resulting distributions of lengths suggest that local maxima occur in the distributions of protofibril lengths as predicted by Cabriolu et al.[22]

S18. Preparation of Transmission Electron Microcopy Samples

We prepared samples for transmission electron microscopy (TEM) analysis using a negative staining method and glow-discharged, carbon-coated copper grids (Electron Microscopy Sciences, Cat no: FCF-200-Cu). We applied 5 μL of each Aβ sample (1 mg×mL⁻¹), which had been permitted to aggregate in pure water for zero, one, two, or three days, to the glow-discharged carbon coated copper grid. After 2 min, we wicked off the fluid on the grids with filter paper and washed the grids with a 5 μL drop of deionized water for 1 min. After wicking off the fluid again, we applied a 5-4, drop of 2% uranyl acetate for 1 min, wicked off the excess fluid on the grids, and allowed the grids to dry.

To examine the morphology of aggregates formed in 2 M KCl, we performed a slightly different procedure. We diluted the 1 mg×mL⁻¹ sample of $A\beta_{(1-40)}$ to a concentration of 0.05 mg/mL in 2 M KCl. We immediately mixed this solution using a vortex shaker and applied 5 μL of the sample to the glow-discharged carbon coated grids. After 10 min, we wicked off the fluid on the grids with filter paper and washed the grids three times with 5 μL deionized water (1 min each time). After wicking off the fluid again, we applied a 5-μL drop of 2% uranyl acetate for 1 min, wicked off the excess fluid on the grids, and allowed the grids to dry. We examined the images of negatively stained Aβ structures using a JEOL 3011 high resolution electron microscope (Jeol Ltd., Tokyo, Japan).

FIG. 42A shows several TEM images of $A\beta_{(1-40)}$ aggregates that were first prepared in pure water like all samples in this work and then exposed to 2 M KCl for 10 min. We analyzed the dimensions of the aggregates in the same manner as FIG. 3 in the main text. For all parameters, the morphology of aggregates that were exposed to 2 M KCl for 10 min, as in the resistive-pulse sensing experiment, was the same as the morphology of aggregates prepared only in pure water (FIG. 3 main text). Table S1. summarizes the characterized parameters. For instance, the diameter of protofibrils and fibers were nearly identical between the two preparations. The range of lengths of the protofibrils were similar between the two treatment methods; however, the probability of observing long protofibrils was slightly higher in samples exposed to 2 M KCl (i.e. $P(l_M>45$ nm) on Day 1-2 of ~0.3-0.4) compared to the samples that were not exposed to KCl (i.e. $P(l_M>45$ nm) on Day 1-2 of ~0.15-0.2) (FIG. 3C inset in the main text and Figure S9C inset). This suggests that brief incubation in solutions with high ionic strengths accelerates the time-dependent aggregation of Aβ such that the number of Aβ aggregates increases, which enables the formation of protofibrils with longer lengths than those produced in solutions in low ionic strengths.

TABLE S1

Morphology of $A\beta_{(1-40)}$ aggregates exposed only to pure water and aggregates that were exposed to 2M KCl for 10 min. Errors are standard deviations from the mean value.

| Treatment | Spherical θ nm | Protofibril θ nm | Fiber x-over θ nm | Fiber flat θ nm² | Distance between x-overs nm |
|---|---|---|---|---|---|
| Pure Water | 6.2 ± 1.2 N = 18 | 6.3 ± 1.5 N = 117 | 5.6 ± 0.8 N = 27 | 11.5 ± 1.5 N = 27 | 97 ± 27 N = 27 |
| 10 min exposure to 2M KCl | 7.2 ± 1.5 N = 32 | 6.5 ± 1.1 N = 178 | 5.4 ± 1.0 N = 7 | 12.7 ± 2.3 N = 7 | 80 ± 9 N = 6 |

References for Sections S11-S19
(1) Yusko, E. C.; Johnson, J. M.; Majd, S.; Prangkio, P.; Rollings, R. C.; Li, J.; Yang, J. Mayer, M. *Nat. Nanotechnol.* 2011, 6, 253-260.
(2) Capone, R.; Quiroz, F. G.; Prangkio, P.; Saluja, I.; Sauer, A. M.; Bautista, M. R.; Turner, R. S.; Yang, J. Mayer, M. *Neurotox. Res.* 2009, 16, 1-13.

(3) Uram, J. D.; Ke, K. Mayer, M. *ACS Nano.* 2008, 2, 857-872.
(4) Pedone, D.; Firnkes, M. Rant, U. *Anal. Chem.* 2009, 81, 9689-9694.
(5) Talaga, D. S. Li, J. L. *J. Am. Chem. Soc.* 2009, 131, 9287-9297.
(6) Stine, W. B.; Dahlgren, K. N.; Krafft, G. A. LaDu, M. *J. Biol. Chem.* 2003, 278, 11612-11622.
(7) Jan, A.; Hartley, D. M. Lashuel, H. A. *Nat. Protoc.* 2010, 5, 1186-1209.
(8) Li, J. L. Talaga, D. S. *J. Phys.-Condes. Matter.* 2010, 22.
(9) Berg, H. C. *Random Walks in Biology*; Princeton University Press: Princeton, N.J., 1993.
(10) Guo, M.; Gorman, P. M.; Rico, M.; Chakrabartty, A. Laurents, D. V. *FEBS Lett.* 2005, 579, 3574-3578.
(11) Hortschansky, P.; Schroeckh, V.; Christopeit, T.; Zandomeneghi, G. Fandrich, M. *Protein Sci.* 2005, 14, 1753-1759.
(12) Kellermayer, M. S. Z.; Karsai, A.; Benke, M.; Soós, K. Penke, B. *Proc. Natl. Acad. Sci. U.S.A.* 2008, 105, 141-144.
(13) Solomentsev, Y. Anderson, J. L. *Industrial & Engineering Chemistry Research.* 1995, 34, 3231-3238.
(14) Solomentsev, Y. Anderson, J. L. *J. Fluid Mech.* 1994, 279, 197-215.
(15) Ai, Y. Qian, S. *Electrophoresis.* 2011, 32, 996-1005.
(16) Fricke, H. *J. Appl. Phys.* 1953, 24, 644-646.
(17) Grover, N. B.; Naaman, J.; Ben-sasson, S. Doljansk, F. *Biophys. J.* 1969, 9, 1398-1414.
(18) DeBlois, R. W.; Uzgiris, E. E.; Cluxton, D. H. Mazzone, H. M. *Anal. Biochem.* 1978, 90, 273-288.
(19) Golibers. Dc *J. Appl. Phys.* 1973, 44, 2580-2584.
(20) Golibersuch, D. C. *Biophys. J.* 1973, 13, 265-280.
(21) Osborn, J. A. *Physical Review.* 1945, 67, 351-357.
(22) Cabriolu, R.; Kashchiev, D. Auer, S. *Biophys. J.* 2011, 101, 2232-2241.
(23) Schmidt, M.; Sachse, C.; Richter, W.; Xu, C.; Fandrich, M. Grigorieff, N. *Proc. Natl. Acad. Sci. U.S.A.* 2009, 106, 19813-19818.

What is claimed is:

1. A method of detecting, quantifying, or characterizing a biomolecule, collection of biomolecules, or particles, comprising:
providing a transit path for biomolecules or particles to pass through a nanopore from a first liquid compartment to a second liquid compartment, wherein the first and second liquid compartments contain electrodes disposed to measure voltage difference, current flow, or resistance between the first and second liquid compartments; and
measuring voltage difference, current flow, or resistance between the first and second liquid compartments over time as individual biomolecules pass through the nanopore;
wherein the nanopore is a passageway through a substrate, the passageway being lined with a fluid wall, wherein the fluid wall comprises a monolayer or a bilayer, the monolayer or the bilayer comprising a lipid anchored ligand and an amphipathic molecule, a surfactant, or a detergent.

2. The method according to claim 1, wherein the monolayer or the bilayer comprises the amphipathic molecule.

3. The method according to claim 1, wherein the fluid wall comprises the bilayer.

4. The method according to claim 1, wherein the monolayer or the bilayer comprises the surfactant or the detergent.

5. The method according to claim 1, wherein the nanopore is characterized by a nominal width perpendicular to the transit path that is about 1.5 to about 50 times the dimension of the biomolecule or particle and wherein the length of the nanopore parallel to the transit path is one to five times its nominal width.

6. The method according to claim 1, wherein the fluid wall comprises the monolayer.

7. The method according to claim 1, wherein the lipid anchored ligand comprises an antibody.

8. The method according to claim 1, wherein the nanopore has a nominal width of 10 to 200 nanometers.

9. The method according to claim 1, wherein the nanopore has a nominal width of 20 to 30 nanometers.

10. The method according to claim 1, wherein the biomolecule comprises a protein or protein aggregate.

11. The method according to claim 1, wherein the biomolecule comprises a nucleic acid.

12. The method according to claim 1, wherein the biomolecule comprises an antibody.

13. The method according to claim 10, wherein the protein is an amyloid $\beta$ protein.

14. The method according to claim 1, wherein the lipid anchored ligand comprises a lipid molecule comprising a ligand, wherein the lipid molecule is bound within the monolayer or the bilayer and the ligand is biotin, cholesterol, sulfonamide, nickel, an antibody, or a non-antibody protein.

15. The method according to claim 13, wherein the ligand is a non-antibody protein comprising a thiol group, a maleimide group, or a N-hydroxysuccimide (NHS) ester group.

16. The method according to claim 1, wherein the monolayer or the bilayer comprises the amphipathic molecule, the amphipathic molecule being a phospholipid or a sphingolipid.

17. A method of measuring a translocation time, ligand affinity, charge, volume, shape, size, or other characteristic of a biomolecule, the method comprising:
detecting and measuring a change in conductivity, resistivity, resistance, conductance, current flow, voltage, or other electrical parameter measured between two liquid compartments separated by and fluidically coupled through a synthetic nanopore upon translocation of the biomolecule from one liquid compartment through the synthetic nanopore to the other liquid compartment; and
deriving the biomolecule characteristic from the measured electrical parameter,
wherein the synthetic nanopore comprises a passageway lined with a fluid wall, wherein the fluid wall comprises a monolayer or a bilayer, the monolayer or the bilayer comprising a lipid anchored ligand and an amphipathic molecule, a surfactant, or a detergent.

18. A device for measuring a parameter of a biomolecule using the Coulter principle, the device comprising:
a first liquid compartment and a second liquid compartment;
a synthetic nanopore disposed between and providing a fluid path between the first liquid compartment and second liquid compartment, and defining a fluid flow direction from the first liquid compartment to the second liquid compartment;
a first electrode in the first liquid compartment and a second electrode in the second liquid compartment; and
means for controlling the first electrode and second electrode to measure resistance, voltage difference, or current flow between the first and second electrodes, wherein the synthetic nanopore is a passageway between the first liquid compartment and second liquid compartment lined with a fluid wall, and wherein the passageway lined with the fluid wall provides a transit path for the biomolecule to pass from the first liquid compartment to the second liquid compartment, wherein the fluid wall comprises a monolayer or a bilayer, the monolayer or the bilayer comprising a lipid achnored ligand and an amphipathic molecule, a surfactant, or a detergent.

19. The device according to claim 18, wherein a dimension of the synthetic nanopore perpendicular to the fluid flow direction is 10 to 100 nanometers.

20. The device according to claim 18, wherein the synthetic nanopore has a length in the fluid flow direction of 10 to 100 nanometers.

\* \* \* \* \*